(12) United States Patent
Cohen et al.

(10) Patent No.: US 6,900,367 B2
(45) Date of Patent: May 31, 2005

(54) **TRANSGENIC *DROSOPHILA MELANOGASTER* EXPRESSING A β42 IN THE EYE**

(75) Inventors: Dalia Cohen, Livingston, NJ (US); Uwe Jochen Dengler, Loerrach (DE); Alyce Lynn Finelli, Parsippany, NJ (US); Felix Freuler, Riehen (CH); Mary Konsolaki, Westfield, NJ (US); Mischa Werner Henri Marie Reinhardt, Bantzenheim (FR); Susan Zusman, Sudbury, MA (US)

(73) Assignee: Novartis, East Hanover, NJ (US)

( * ) Notice: Subject to any disclaimer, the term of this patent is extended or adjusted under 35 U.S.C. 154(b) by 242 days.

(21) Appl. No.: 09/964,899

(22) Filed: Sep. 27, 2001

(65) Prior Publication Data

US 2002/0174446 A1 Nov. 21, 2002

Related U.S. Application Data

(60) Provisional application No. 60/298,309, filed on Jun. 14, 2001, and provisional application No. 60/236,893, filed on Sep. 29, 2000.

(51) Int. Cl.$^7$ .................... A01K 67/00; A01K 67/033; G01N 33/00
(52) U.S. Cl. ................ 800/13; 800/12; 800/3
(58) Field of Search ............... 800/13, 12, 3, 800/18

(56) References Cited

U.S. PATENT DOCUMENTS

| | | | |
|---|---|---|---|
| 5,795,963 A | 8/1998 | Mullan | 530/350 |
| 5,811,633 A | 9/1998 | Wadsworth et al. | 800/12 |
| 5,840,540 A | 11/1998 | St. George-Hyslop et al. | 435/69.1 |
| 5,891,991 A | 4/1999 | Wasco et al. | 530/300 |
| 5,986,054 A | 11/1999 | St. George-Hyslop et al. | 530/350 |

FOREIGN PATENT DOCUMENTS

| | | |
|---|---|---|
| WO | WO 94/00569 | 1/1994 |
| WO | WO 98/54300 | 12/1998 |
| WO | WO 01/85912 A2 | 11/2001 |

OTHER PUBLICATIONS

Siman, 2000, Journal of Neuroscience, vol. 20, pp. 8717–8726.*
Niemann, 1997, Transg. Res. vol. 7, pp. 73–75.*
Overbeek, 1994, "Factors affecting transgenic animal production," Transgenic animal technology, pp. 96–98.*
Wall, 1996, Theriogenology, vol. 45, pp. 57–68.*
Houdebine, 1994, J. Biotech. vol. 34, pp. 269–287.*
Kellum, 1991, Cell, vol. 64, pp. 941–950.*
Wall, 1996, Theriogenology, vol. 45, pp. 57–68.
Abrams et al., "Programmed cell death during Drosophila embryogenesis," Development, vol. 117, pp. 29–43 (1993).

Abstract, Finelli et al., "Alzheimer's Abeta peptide induces rough eye phenotype in Drosophila," 42nd Annual Drosophila Research Conference, Mar. 2001.
Abstract, Finelli et al., "Beta–Amyloid Induced Neurodegeneration in the Drosophila Eye," Neurobiology of Drosophila, CSHL Oct. 2001.
Abstract, Finelli et al., "Genetic analysis of Alzheimer's–related pathways in Drosophila," Therapeutic Opportunities in Neurodegenerative Diseases, CSHL 2000.
Abstract, Lanoue et al., "Dominant phenotypes caused by overexpression of human amyloid precursor protein (APP) in flies," 41st Annual Drosophila Research Conference, Mar. 2000.
Abstract, Lanoue, et al., "Dominant phenotypes caused by overexpression of human amyloid precursor protein (APP) in flies," World Alzheimer Congress 2000.
Anderton et al., Does dysregulation of the Notch and wingless/Wnt pathways underlie the pathogenesis of Alzheimer's disease? Molecular Medicine Today, vol. 6, pp. 54–59 (2000).
Behl et al., "Amyloid beta peptide induces necrosis rather than apoptosis," Brain Research, vol. 645, pp. 253–264 (1994).
Behl, C., "Apoptosis and Alzheimer's Disease," J. Neural Transm, vol. 107, pp. 1325–1344 (2000).
Benzer, S., "Behavioral Mutants of Drosophila Isolated by Countercurrent Distribution," PNAS, vol. 58, pp. 1112–1119 (1967).
Bertram et al., "Evidence for Genetic Linkage of Alzheimer's Disease to Chromosome 10q," Science, vol. 290, pp. 2302–2303 (2000).
Blochlinger et al., "Primary structure and expression of a product from cut, a locus involved in specifying sensory organ identity in Drosophila," Nature, vol. 333, pp. 629–635, (1988).
Boulianne et al., "Cloning and characterization of the Drosophila presenilin homologue," Molecular Neuroscience, vol. 8, pp. 1025–1029 (1997).
Brand et al., "Targeted gene expression as a means of altering cell fates and generating dominant phenotypes," Development, vol. 118, p. 401–415 (1993).

(Continued)

*Primary Examiner*—Joseph Woitach
*Assistant Examiner*—Valarie Bertoglio
(74) *Attorney, Agent, or Firm*—Regina Bautista

(57) ABSTRACT

Transgenic flies displaying altered phenotypes due to expression of the Abeta and C99 portions of the human APP gene are disclosed. Use of these flies in a method to identify *Drosophila* genes and the human homologs of these *Drosophila* genes, that are potentially involved in Alzheimer's Disease, is also disclosed. The use of said human homologs as drug targets for the development of therapeutics to treat Alzheimer's Disease and other conditions associated with defects in the APP pathway, as well as pharmaceutical compositions comprising substances directed to these genes, are also disclosed.

5 Claims, No Drawings

OTHER PUBLICATIONS

Brewer et al., "Age–related Toxicity to Lactate, Glutamate, and Beta–Amyloid in Cultured Adult Neurons," Neurobiology of Aging, vol. 19(6), pp. 561–568 (1998).

Cagan et al., "The Emergence of Order in the Drosophila Pupal Retina," Developmental Biology, vol. 136, pp. 346–362 (1989).

Cao et al., "A Transcriptively Active Complex of APP with Fe65 and Histone Acetyltransferase Tip60," Science, vol. 293, pp. 115–120 (2001).

Cescato et al., "Increased Generation of Alternatively Cleaved Beta–Amyloid Peptides in Cells Expressing Mutants of the Amyloid Precursor Protein Defective in Endocytosis," Journal of Neurochemistry, pp. 1131–1139 (2000).

Chan et al., "Presenilin–1 Mutations Increase Levels of Ryanodine Receptors and Calcium Release in PC12 Cells and Cortical Neurons," Journal of Biological Chemistry, vol. 275(24), pp.18195–18200 (2000).

Chen et al., "Where do Alzheimer's Plaques and Tangles come from? Aging–induced Protein Degradation Inefficiency," Frontiers in Bioscience, vol. 6, E1–11 (2001).

Citron et al., "Excessive production of amyloid beta–protein by peripheral cells of symptomatic and presymptomatic patients carrying the Swedish familial Alzheimer disease mutation," Proc. Natl. Acad. Sci., vol. 91, pp. 11993–11997 (1994).

Citron et al., "Generation of Amyloid Beta Protein from Its Precursor Is Sequence Specific," Neuron, vol. 14, pp. 661–670 (1995).

Citron et al., "Mutant presenilins of Alzheimer's disease increase production of 42–residue amyloid beta–protein in both transfected cells and transgenic mice," Nature Medicine, vol. 3(1), pp. 67–72 (1997).

Cook et al., "Alzheimer's Abeta(1–42) is generated in the endoplasmic reticulum/intermediate compartment of NT2N cells," Nature Medicine, vol. 3(9), pp. 1021–1023 (1997).

Cotman et al., "A Potential Role for Apoptosis in Neurodegeneration and Alzheimer's Disease," Molecular Neurobiology, vol. 10, pp. 19–45 (1995).

Coughlan et al., "Factors influencing the processing and function of the amyloid beta precursor protein—a potential therapeutic target in Alzheimer's disease?" Pharmacology & Therapeutics, vol. 86, pp. 111–144 (2000).

Czech et al., "APP/Preseninlin interaction: The amino–terminus of presenilin 2 is able to interact with Abeta42 in vitro," Society for Neurscience, vol. 25, 641.1999.

Dawson, V.L., "Of Flies and Mice," Science, vol. 288, pp. 631–632 (2000).

De Strooper et al., "A presenilin–1–dependent gamma–secretase–like protease mediates release of Notch intracellular domain," Nature, vol. 398, pp. 518–522 (1999).

Deveraux et al., "lAP family proteins—suppressors of apoptosis," Genes. Dev., vol. 13, pp. 239–252 (1999).

Diaz–Benjumea et al., "Interaction between Dorsal and Ventral Cells in the lmaginal Disc Directs Wing Development in Drosophila," Cell, vol. 75, pp. 741–752 (1993).

Dyrks et al., "Generation of betaA4 from the amyloid protein precursor and fragments thereof," FEBS Lett., vol. 335(1), pp. 89–93 (1993).

Ellis et al, "Expression of Drosophila glass protein and evidence for negative regulation of its activity in non–neuronal cells by another DNA–binding protein," Development, vol. 119, pp. 855–865 (1993).

Engelender et al., "Synphilin–1 associates with alpha–synuclein and promotes the formation of cytosolic inclusions," Nature Genetics, vol. 22, pp. 110–114 (1999).

Engels, W.R., "A trans–Acting Product Needed for P Factor Transposition in Drosophila," Science, vol. 226, pp. 1194–1196 (1984).

Ertekin–Taner, et al., "Linkage of Plasma ABeta42 to a Quantitative Locus on Chromosome 10 in Late–Onset Alzheimer's Disease Pedigrees," Science, vol. 290, pp. 2303–2304 (2000).

Feany et al., "A Drosophila model of Parkinson's disease," Nature, vol. 404, pp. 394–398 (2000).

Fernandez–Funez et al., "Identification of genes that modify ataxin–1–induced neurodegeneration," Nature, vol. 408, pp. 101–106 (2000).

Flucher et al., "Distribution of Na+ Channels and Ankyrin in Neuromuscular Junctions is Complementary to That of Acetylcholine Receptors and the 43 kd Protein," Neuron, vol. 3, pp. 163–175 (1989).

Fortini et al., "Modeling human neurodegenerative diseases in Drosophila on a wing and a prayer," Trends Genet., vol. 16, pp. 161–167 (2000).

Fossgreen et aI., "Transgenic Drosophila expressing human amyloid precursor protein show gamma–secretase activity and a blistered–wing phenotype," Proc. NatI. Acad. Sci. USA, vol. 95, pp. 13703–13708 (1998).

Fraser et al., "Ionic effects of the Alzheimer's disease beta–amyloid precursor protein and its metabolic fragments," Trends Neurosci., vol. 20(2), pp. 67–72 (1997).

Fukumoto et al., "Amyloid Beta Protein Deposition in Normal Aging Has Same Characteristics as That in Alzheimer's Disease," Am. J. Pathol., vol. 148, pp. 259–265 (1996).

Fukuta et al., "Difference in toxicity of beta–amyloid peptide with aging in relation to nerve growth factor content in rat brain," J. Neural Transm., vol. 108, pp. 221–230 (2001).

Giovannelli et al., "Long–term Changes in the Aggregation State and Toxic Effects of Beta–Amyloid Injected into the Rat Brain," Neuroscience, vol. 87(2), pp. 349–357 (1998).

Goate et al., "Segregation of a missense mutation in the amyloid precursor protein gene with familial Alzheimer's disease," Nature, vol. 349, p. 704–706 (1991).

Golde et al., "Processing of the Amyloid Protein Precursor to Potentially Amyloidogenic Derivatives," Science, vol. 255, pp. 728–730 (1992).

Gouras et al., "Intraneuronal ABeta42 Accumulation in Human Brain," Am. J. Pathol., vol. 156, pp. 15–20 (2000).

Greenfield et al., "Endoplasmic reticulum and trans–Golgi network generate distinct populations of Alzheimer beta–amyloid peptides," Proc. NatI. Acad. Sci. USA, vol. 96, pp. 742–747 (1999).

Grether et al., "The head involution defective gene of Drosophila melanogaster functions in programmed cell death," Genes and Development, vol. 9, pp. 1694–1708 (1995).

Guo et al., "Drosophila presenilin Is Required for Neuronal Differentiation and Affects Notch Subcellular Localization and Signaling," The Journal of Neuroscience, vol. 19(19), pp. 8435–8442 (1999).

Guo et al., "Physical and genetic interaction of filamin with presenilin in Drosophila," Journal of Cell Science, vol. 113, pp. 3499–3508 (2000).

Harper et al., "Observation of metastable Abeta amyloid protofibrils by atomic force microscopy," Chem. Biol, vol. 4, pp. 119–125 (1997).

Hartley et al., "Protofibrillar Intermediates of Amyloid Beta–Protein Induce Acute Electrophysiological Changes and Progressive Neurotoxicity in Cortical Neurons," The Journal of Neuroscience, vol. 19(20), p. 8876–8884 (1999).

Hartmann et al., "Distinct sites of intracellular production for Alzheimer's disease ABeta40/42 amyloid peptides," Nature Medicine, vol. 3(9), pp. 1016–1020 (1997).

Hay et al., "Expression of baculovirus P35 prevents cell death in Drosophila," Development, vol. 120, pp. 2121–2129 (1994).

Hay et al., "P element insertion–dependent gene activation in the Drosophila eye," Proc. Natl. Acad. Sci., vol. 94, pp. 5195–5200 (1997).

Hellstroem–Lindahl et al., "Nicotinic acetylcholine receptors during prenatal development and brain pathology in human aging," Behavioural Brain Research, vol. 113, pp. 159–168 (2000).

Hellstroem–Lindahl E., "Modulation of beta–amyloid precursor protein processing and tau phosphorylation by acetylcholine receptors," European Journal of Pharmacology, vol. 393, pp. 255–263 (2000).

Hsia et al., "Plaque–independent disruption of neural circuits in Alzheimer's disease mouse models," Proc. Natl. Acad. Sci. USA., vol. 96, pp. 3228–3233 (1999).

Hussain et al., "Identification of a Novel Aspartic Protease (ASp 2) as Beta–Secretase," Molecular and Cellular Neuroscience, vol. 14, p. 419–427 (1999).

Hyman et al., "Role of the Low–density Lipoprotein Receptor–Related Protein in Beta–Amyloid Metabolism and Alzheimer Disease," Arch. Neurol. vol. 57, pp. 646–650 (2000).

Iwata et al., "Metabolic Regulation of Brain ABeta by Neprilysin," Sicence, vol. 292, pp. 15550–15552 (2001).

Jackson et al., "Polyglutamine–Expanded Human Huntingtin Transgenes Induce Degeneration of Drosophila Photoreceptor Neurons," Neuron, vol. 21, pp. 633–642 (1998).

Jarrett et al., "The Carboxy Terminus of the Beta Amyloid Protein Is Critical for the Seeding of Amyloid Formation: Implications for the Pathogenesis of Alzheimer's Disease," Biochemistry, vol. 32, pp. 4693–4697 (1993).

Jiang et al., "Telomerase expression in human somatic cells does not induce changes associated with a transformed phenotype," Nature Genetics, vol. 21, pp. 111–114 (1999).

Karim et al., "Ectopic expression of activated Ras 1 induces hyperplastic growth and increased cell death in Drosophila imaginal tissues," Development, vol. 125, pp. 1–9 (1998).

Kazemi–Esfarjani et al., "Genetic Suppression of Polyglutamine Toxicity in Drosophila," Science, vol. 287, pp. 1837–1840 (2000).

Kelliher et al., "Alterations in the Ryanodine Receptor Calcium Release Channel Correlate With Alzheimer's Disease Neurofibrillary and Beta–Amyloid Pathologies," Neuroscience, vol. 92(2), pp. 499–513 (1999).

Kellum et al., "A Position–Effect Assay for Boundaries of Higher Order Chromosomal Domains," Cell, vol. 64, pp. 941–950 (1991).

Konsolaki et al., "Windbeutel, a gene requried for dorsoventral patterning in Drosophila, encodes a protein that has homologies to vertebrate proteins of the endoplasmic reticulum," Genes & Development, vol. 12, pp. 120–131 (1998).

Kordeli et al., "An Isoform of Ankyrin is Localized at Notes of Ranvier in Myelinated Axons of Central and Peripheral Nerves," The Journal of Cell Biology, vol. 110, 1341–1352 (1990).

Kordeli et al., "AnkyrinG; A New Ankyrin Gene with Neural–Specific Isoforms Localized at the Axonal Initial Segment and Node of Ranvier," "The Journal of Biological Chemistry," vol. 270(5), pp. 2352–2359 (1995).

Kordeli et al., "Distinct Ankyrin Isoforms at Neuron Cell Bodies and Nodes of Ranvier Resolved Using Erythrocyte Ankyrin–Deficient Mice," The Journal of Cell Biology, vol. 114(6), pp. 1243–1259 (1991).

Kulic et al., "Separation of presenilin function in amyloid beta–peptide generation and endoproteolysis of Notch," Proc. Natl. Acad. Scie., vol. 97(11), pp. 5913–5918 (2000).

LaFerla et al., "The Alzheimer's ABeta peptide induces neurodegeneration and apoptotic cell death in transgenic mice," Nature Genetics, vol. 9, pp. 21–30 (1995).

Lambert et al., "Diffusible, nonfibrillar ligands derived from ABeta1–42 are potent central nervous system neurotoxins," Proc. Natl. Acad. Sci. USA, vol. 95, pp. 6448–6453 (1998).

Launer et al., "Regional Differences in the Incidence of Dementia in Europe: EURODEM Collaborative Analyses," In lqbal, K., Swaab, D.F., Winblad, B. and Wisniewski, H.M. (Eds), Alzheimer's Disease and Related Disorders, pp. 9–15 (1999).

Lavedan, C., "The Synuclein Family," Genome Research, vol. 8, pp. 871–880 (1998).

Lorenzo et al., "Beta–Amyloid neurotoxicity requires fibril formation and is inhibited by Congo red," Proc. Natl. Acad. Sci., vol. 91, pp. 12243–12247 (1994).

Lucassen et al., "DNA Damage Distribution in the Human Brain as Shown by In Situ End Labeling; Area–specific Differences in Aging and Alzheimer Disease in the Absence of Apoptotic Morphology," Journal of Neuropathology and Experimental Neurology, vol. 56(.

Luedecking et al., "Genetic polymorphism in the persyn (gamma–synuclein) gene and the risk of Alzheimer's disease," Neuroscience Letters, vol. 261, pp. 186–188 (1999).

Luo et al., "Human Amyloid Precursor Protein Ameliorates Behavioral Deficit of Flies Deleted for Appl Gene," Neuron, vol. 9, pp. 595–605 (1992).

Luo et al., "Identification, Secretion, and Neural Expression of APPL, a Drosophila Protein Similar to Human Amyloid Protein Precursor," The Journal of Neuroscience, vol. 10(12), p. 3849–3861 (1990).

Mattson M.P., "Cellular Actions of Beta–Amyloid Precursor Protein and Its Soluble and Fibrillogenic Derivatives," Physiological Reviews, vol. 77(4), pp. 1081–1132 (1997).

McKee et al., "The neurotoxicity of amyloid beta protein in aged primates," Amyloid: Int. J. Exp. Clin. Invest. vol. 5, pp. 1–9 (1998).

McLean et al., "Soluble Pool of ABeta Amyloid as a Determinant of Severity of Neurodegeneration in Alzheimer's Disease," Ann. Neurol., vol. 46, pp. 860–866 (1999).

Mills et al., "Regulation of Amyloid Precursor Protein Cleavage," Journal of Neurchemistry, vol. 72, pp. 443–460 (1999).

Moses et al., "Glass encodes a site–specific DNA–binding protein that is regulated in response to positional signals in the developing Drosophila eye," Genes & Development, vol. 5, pp. 583–593 (1991).

Moses et al., "The glass gene encodes a zinc–finger protein required by Drosophila photoreceptor cells," Nature, vol. 340, pp. 531–536 (1989).

Mucke et al., "High–Level Neuronal Expression of A Beta1–42 in WId–Type Human Amyloid Protein Precursor Transgenic Mice: Synaptotoxicity without Plaque Formation," The Journal of Neuroscience, vol. 20(11), pp. 4050–4058 (2000).

Mukherjee et al., "Insulysin Hydrolyzes Amyloid BetaPeptides to Products That Are Neither Neurotoxic Nor Deposit on Amyloid Plaques," J. Neurosci., vol. 20, pp. 8745–8749 (2000).

Mullan et al., "A pathogenic mutation for probable Alzheimer's disease in the APP gene at the N–terminus of beta–amyloid," Nat. Genet., vol. 1, pp. 345–347 (1992).

Murayama et al., "Enhancement of amyloid Beta 42 secretion by 28 different presenilin 1 mutations of familial Alzheimer's disease," Neurosci. Lett., vol. 265, pp. 61–63 (1999).

Myers et al., "Susceptibility Locus for Alzheimer's Disease on Chromosome 10," Science, vol. 290, pp. 2304–2305 (2000).

Näslund et al., "Correlation Between Elevated Levels of Amyloid beta–Peptide in the Brain and Cognitive Decline," J.A.M.A., vol. 283, pp. 1571–1577 (2000).

Ninkina et al., "Organization, expression and polymorphism of the human persyn gene," Human Molecular Genetics, vol. 7(9), pp. 1417–1424 (1998).

Okamoto et al., "Ligand–dependent G Protein Coupling Function of Amyloid Transmembrane Precursor," The Journal of Biological Chemistry, vol. 270(9), pp. 4205–4208 (1995).

Paganetti et al., "Amyloid Precursor Protein Truncated at any of the Gamma–Secretase Sites Is Not Cleaved to Beta–Amyloid," Journal of Neuroscience Research, vol. 46, pp. 283–293 (1996).

Pike et al., "Neurodegeneration Induced by beta–Amyloid Peptides in vitro: The Role of Peptide Assembly State," J. Neurosci., vol. 13, pp. 1676–1687 (1993).

Poirier, J., "Apolipoprotein E and Alzheimer's Disease—A Role in Amyloid Catabolism," Ann. N.Y. Acad. Sci., vol. 924, pp. 81–90 (2000).

Pradier et al., "Mapping the APP/Presenilin (PS) Binding Domains: The Hydrophilic N–Terminus of PS2 is Sufficient for Interaction with APP and Can Displace APP/PS1 Interaction," Neurobiology of Disease, vol. 6, pp. 43–55 (1999).

Price, D., "New order from neurological disorders," Nature, vol. 399, pp. A3–A5 (1999).

Qiu et al., "Degradation of Amyloid Beta–Protein by a Serine Protease–Alpha Macroglobulin Complex," The Journal of Biological Chemistry, vol. 271 (14), pp. 8443–8451 (1996).

Robertson et al., "A Stable Genomic Source of P Element Transposase in Drosophila melanogaster," Genetics, vol. 118, pp. 461–470 (1988).

Rorth et al., "Systematic gain–of–function genetics in Drosophila," Development, vol. 125(6), pp. 1049–1057 (1998).

Rosen et al., "A Drosophila gene encoding a protein resembling the human beta–amyloid protein precursor," Proc. NatI. Acad. Sci., vol. 86, pp. 2478–2482 (1989).

Rubin et al., "Comparative Genomics of the Eukaryotes," Science, vol. 287, pp. 2204–2215 (2000).

Rubin et al., "Genetic Transformation of Drosophila with Transposable Element Vectors," Science, vol. 218, pp. 348–353 (1982).

Schneider–Maunoury et al., "Disruption of Krox–20 Results in Alteration of Rhombomeres 3 and 5 in the Developing Hindbrain," Cell, vol. 75, pp. 1199–1214 (1993).

Schultz et al., "SAM as a protein interaction domain involved in developmental regulation," Protein Science, vol. 6, pp. 249–253 (1997).

Selkoe D. J., "Alzheimer's Disease: Genes, Proteins, and Therapy," Physiol. Rev., vol. 81(2), pp. 741–766 (2001).

Selkoe, D. J., "Translating cell biology into therapeutic advances ih Alzheimer's disease," Nature, vol. 399, pp. A23–A31 (1999).

Sherrington et al., "Cloning of a gene bearing missense mutations in early–onset familial Alzheimer's disease," Nature, vol. 375, pp. 754–760 (1995).

Sinha et al., "Purification and cloning of amyloid precursor protein beta–secretase from human brain," Nature, vol. 402(2), pp. 537–540 (1999).

Skovronsky et al., "Detection of a Novel Intraneuronal Pool of Insoluble Amyloid Beta Protein that accumulates with Time in Culture," J. Cell Biol., vol. 141, pp. 1031–1039 (1998).

Smale et al., "Evidence for Apoptotic Cell Death in Alzheimer's Disease," Exp. Neurol., vol. 133, pp. 225–230 (1995).

Spradling et al., "The Effect of Chromosomal Position on the Expression of the Drosophila Xanthine Dehydrogenase Gene," Cell, vol. 34, pp. 47–57 (1983).

Srinivasan et al., "Ankyrin and spectrin associate with voltage–dependent sodium channels in brain," Nature, vol. 333, pp. 177–180 (1988).

Stadelmann et al., "Alzheimer Disease: DNA Fragmentation Indicates Increased Neuronal Vulnerability, but no Apoptosis," J. Neuropathol. Exp. Neurol, vol. 57, pp. 456–464 (1998).

Struhl et al., "Presenilin is required for activity and nuclear access of Notch in Drosophila," Nature, vol. 398, pp. 522–525 (1999).

Su et al., "lmmunohistochemical evidence for apoptosis in Alzheimer's disease," Clinical Neuroscience and Neuropathology, NeuroReport, vol. 5, pp. 2529–2533 (1994).

Suzuki et al., "An Increased Percentage of Long Amyloid Beta Protein Secreted by Familial Amyloid Beta Protein Precursor (BetaAPP717) Mutants," Science, vol. 264, pp. 1336–1340 (1994).

Swiatek et al., "Perinatal lethality and defects in hindbrain development in mice homozygous for a targeted mutation of the zinc finger gene Krox20," Genes & Development, vol. 7, pp. 2071–2084 (1993).

Tamaoka et al., "Amyloid beta protein 1–42/43 (Abeta 1–42/43) in cerebellar diffuse plaques: enzyme–linked immunosorbent assay and immunocytochemical study," Brain Res., vol. 679, pp. 151–156 (1995).

Thanos et al., "Oligomeric Structure of the Human EphB2 Receptor SAM Domain," Science, vol. 283, pp. 833–836 (1999).

Timmerman et al., "Novel missense mutation in the early growth rsponse 2 gene associated with Dejerine–Sottas syndrome phenotype," Neurology, vol. 52, pp. 1827–1832 (1999).

Torroja et al., "Neuronal overexpression of APPL, the Drosophila homologue of the amyloid precursor protein (APP), disrupts axonal transport," Current Biology, vol. 9(9), pp. 489–492 (1999).

Torroja et al., "The Drosophila beta–Amyloid Precursor Protein Homolog Promotes Synapse Differentiation at the Neuromuscular Junction," The Journal of Neuroscience, vol. 19(18), pp. 7793–7803 (1999).

Trommsdorff et al., "Interaction of Cytosolic Adaptor Proteins with Neuronal Apolipoprotein E Receptors and the Amyloid Precursor Protein," The Journal of Biological Chemistry, vol. 273(50), pp. 33556–33560 (1998).

Tucker et al., "The Plasmin System Is Induced by and Degrades Amyloid–Beta Aggregates," The Journal of Neuroscience, vol. 20(11), pp. 3937–3945 (2000).

Turner et al., "Amyloids Beta40 and Beta42 are Generated Intracellularly in Cultured Human Neurons and Their Secretation Increases with Maturation," The Journal of Biological Chemistry, vol. 271(15), pp. 8966–8970 (1996).

van Leuven, F., "Single and multiple transgenic mice as models for Alzheimer's disease," Progress in Neurobiology, vol. 61, pp. 305–312, (2000).

Vassar et al., "Beta–Secretase Cleavage of Alzheimer's Amyloid Precursor Protein by the Transmembrane Aspartic Protease BACE," Science, vol. 286, pp. 735–741 (1999).

Vekrellis et al., "Neurons Regulate Extracellular Levels of Amyloid Beta–Protein via Proteolysis by Insulin–Degrading Enzyme," The Journal of Neuroscience, vol. 20(5), pp. 1657–1665 (2000).

Walsh et al., "Amyloid Beta–Protein Fibrillogenesis," The Journal of Biological Chemistry, vol. 274(36), pp. 25945–25952 (1999).

Walsh et al., "Amyloid Beta–Protein Fibrillogenesis," The Journal of Biological Chemistry, vol. 272(35), pp. 22364–22372 (1997).

Warner et al., "Mutations in the early growth response 2 (EGR2) gene are associated with hereditary myelinopathies," Nature Genetics, vol. 18, pp. 382–384 (1998).

Warrick et al., "Expanded Polyglutamine Protein Forms Nuclear Inclusions and Causes Neural Degeneration in Drosophila," Cell, vol. 93, pp. 939–949 (1998).

Wild–Bode et al., "Intracellular Generation and Accumulation of Amyloid Beta–Peptide Terminating at Amino Acid 42," The Journal of Biological Chemistry, vol. 272(26), pp. 16085–16088 (1997).

Wittmann et al., "Tauopathy in Drosophila: Neurodegeneration Without Neurofibrillary Tangles," Science, vol. 293, pp. 711–714 (2001).

Wyss–Coray et al., "TGF–Beta1 promotes microglial amyloid–beta clearance and reduces plaque burden in transgenic mice," Nat. Med., vol. 7(5), 612–618 (2001).

Xia et al., "Interaction between amyloid precursor protein and presenilins in mammalian cells: Implications fo the pathogenesis of Alzheimer disease," Proc. Natl. Acad. Sci., vol. 94, pp. 8208–8213 (1997).

Yan et al., "Membrane–anchored aspartyl protease with Alzheimer's disease beta–secretase activity," Nature, vol. 402, pp. 533–537 (1999).

Ye et al., "Apoptotic Activities of Wild–type and Alzheimer's Disease–related Mutant Presenilins in Drosophila melanogaster," J. Cell Biol., vol. 146, ppp. 1351–1364 (1999).

Ye et al., "Neurogenic phenotypes and altered Notch processing in Drosophila Presenilin mutants," Nature, vol. 398, pp. 525–529 (1999).

Zhang et al., "Identification of a novel family of putative methyltransferases that interact with human and Drosophila presenilins," Gene, vol. 280, pp. 135–144 (2001).

* cited by examiner

SEQUENCE LISTING

<160> NUMBER OF SEQ ID NOS: 53

<210> SEQ ID NO 1
<211> LENGTH: 123
<212> TYPE: DNA
<213> ORGANISM: Homo Sapien

<400> SEQUENCE: 1

| gacgcagaat tccgacatga ctcaggatat gaagttcatc atcaaaaatt ggtgttcttt | 60 |
| gcagaagatg tgggttcaaa caaaggtgca atcattggac tcatggtggg cggtgttgtc | 120 |
| tag | 123 |

<210> SEQ ID NO 2
<211> LENGTH: 129
<212> TYPE: DNA
<213> ORGANISM: Homo Sapien

<400> SEQUENCE: 2

| gacgcagaat tccgacatga ctcaggatat gaagttcatc atcaaaaatt ggtgttcttt | 60 |
| gcagaagatg tgggttcaaa caaaggtgca atcattggac tcatggtggg cggtgttgtc | 120 |
| atagcgtag | 129 |

<210> SEQ ID NO 3
<211> LENGTH: 300
<212> TYPE: DNA
<213> ORGANISM: Homo Sapien

<400> SEQUENCE: 3

| gacgcagaat tccgacatga ctcaggatat gaagttcatc atcaaaaatt ggtgttcttt | 60 |
| gcagaagatg tgggttcaaa caaaggtgca atcattggac tcatggtggg cggtgttgtc | 120 |
| atagcgacag tgatcgtcat caccttggtg atgctgaaga agaaacagta cacatccatt | 180 |
| catcatggtg tggtggaggt tgacgccgct gtcaccccag aggagcgcca cctgtccaag | 240 |
| atgcagcaga acggctacga aaatccaacc tacaagttct tgagcagat gcagaactag | 300 |

<210> SEQ ID NO 4
<211> LENGTH: 300
<212> TYPE: DNA
<213> ORGANISM: Homo Sapien

<400> SEQUENCE: 4

| gacgcagaat tccgacatga ctcaggatat gaagttcatc atcaaaaatt ggtgttcttt | 60 |
| gcagaagatg tgggttcaaa caaaggtgca atcattggac tcatggtggg cggtgttgtc | 120 |
| atagcgacag tgatcatcat caccttggtg atgctgaaga agaaacagta cacatccatt | 180 |
| catcatggtg tggtggaggt tgacgccgct gtcaccccag aggagcgcca cctgtccaag | 240 |
| atgcagcaga acggctacga aaatccaacc tacaagttct tgagcagat gcagaactag | 300 |

<210> SEQ ID NO 5
<211> LENGTH: 72
<212> TYPE: DNA
<213> ORGANISM: Homo Sapien

<400> SEQUENCE: 5

| atggcgcagt tcctgagact ttgcatctgg ctgctagcgc ttgggtcctg cctcctggct | 60 |
| acagtgcagg ca | 72 |

<210> SEQ ID NO 6
<211> LENGTH: 1537
<212> TYPE: DNA
<213> ORGANISM: Homo Sapien

<400> SEQUENCE: 6

| | | | | | |
|---|---|---|---|---|---|
| ggtgcgccga | gcaggagcag | ggaacaaagg | agcggagagg | ggaggggaga | gagttgggcg | 60 |
| agggagagcc | cccggccggc | tgccagaaga | tcccggcggg | aggaagccca | agtgtcactt | 120 |
| gaattccacc | caaggagcgg | gcgcctggga | tcagagcgtc | ctgtttagca | ataacggctg | 180 |
| gagcacgtcc | tacaagttac | gggagagtcg | gctgtgaagg | agacgttcgc | ttatcccctg | 240 |
| tgtccccgct | cctggcccct | ccagaccccc | gccttgcctc | cgctgggag | gggagatcca | 300 |
| gaatgaaagg | caagaaaggt | attgttgcag | catctggcag | tgagactgag | gatgaggaca | 360 |
| gcatggacat | tcccttggac | ctttcttcat | ccgctggctc | aggcaagaga | ggagaaggg | 420 |
| gcaacctacc | caaggagtct | gtgcagattc | ttcgggattg | gctgtatgag | caccgttaca | 480 |
| atgcctatcc | ttcagagcaa | gaaaaagcgt | tgctgtccca | gcaaacacac | ctgtctacgc | 540 |
| tacaggtctg | taactggttc | atcaacgccc | gccgcaggct | cctccctgac | atgctgagaa | 600 |
| aggatggcaa | agatccaaat | cagttcacaa | tttcccgccg | tggggccaag | atttctgaaa | 660 |
| cgagctctgt | ggagtccgtg | atgggcatca | aaaacttcat | gccagctcta | gaggagaccc | 720 |
| catttcattc | ctgtacagct | gggccaaacc | caacccctagg | gaggccactg | tctcctaagc | 780 |
| cgtcatcccc | gggatcagtt | ttggctcgtc | catcagtgat | ctgccatacc | actgtgactg | 840 |
| cattgaaaga | tgtccctttc | tctctctgcc | agtcggtcgg | tgtgggacaa | acacagata | 900 |
| tacagcagat | agcggccaaa | aacttcacag | acacctctct | catgtaccca | gaggacactt | 960 |
| gtaaatctgg | accaagtacg | aatacacaga | gtggtctttt | caacactcct | ccccctactc | 1020 |
| caccggacct | caaccaggac | ttcagtggat | ttcagcttct | agtggatgtt | gcactcaaac | 1080 |
| gggctgcaga | gatggagctt | caggcaaaac | ttacagctta | acccattttc | aagcaaaaca | 1140 |
| gttctcagaa | atgtcatgat | tgccggggtg | aaggcaagag | atgaattgca | ttattttata | 1200 |
| tatttttat | taatatttgc | acatgggatt | gctaaaacag | cttcctgtta | ctgagatgtc | 1260 |
| ttcaatggaa | tacagtcatt | ccaagaacta | taaacttaaa | gctactgtag | aaacaaaggg | 1320 |
| ttttctttt | taaatgtttc | ttggtagatt | attcataatg | tgagatggtt | cccaatatca | 1380 |
| tgtgattttt | ttttcctcc | ccttcccttt | ttttgttatt | ttttcagact | gtgcaatact | 1440 |
| tagagaacct | atagcatctt | ctcattccca | tgtggaacag | gatgcccaca | tactgtctaa | 1500 |
| ttaataaatt | ttccattttt | tttcaaacaa | gtatgaa | | | 1537 |

<210> SEQ ID NO 7
<211> LENGTH: 332
<212> TYPE: PRT
<213> ORGANISM: Homo Sapien

<400> SEQUENCE: 7

Ile Pro Pro Lys Glu Arg Ala Pro Gly Ile Arg Ala Ser Cys Leu Ala
1               5                   10                  15

Ile Thr Ala Gly Ala Arg Pro Thr Ser Tyr Gly Arg Val Gly Cys Glu
            20                  25                  30

Gly Asp Val Arg Leu Ser Pro Val Ser Pro Leu Leu Ala Pro Pro Asp
        35                  40                  45

Pro Arg Leu Ala Ser Arg Trp Glu Gly Arg Ser Arg Met Lys Gly Lys

```
                50                  55                  60
Lys Gly Ile Val Ala Ala Ser Gly Ser Glu Thr Glu Asp Glu Asp Ser
 65                  70                  75                  80

Met Asp Ile Pro Leu Asp Leu Ser Ser Ala Gly Ser Gly Lys Arg
                 85                  90                  95

Arg Arg Arg Gly Asn Leu Pro Lys Glu Ser Val Gln Ile Leu Arg Asp
                100                 105                 110

Trp Leu Tyr Glu His Arg Tyr Asn Ala Tyr Pro Ser Glu Gln Glu Lys
                115                 120                 125

Ala Leu Leu Ser Gln Gln Thr His Leu Ser Thr Leu Gln Val Cys Asn
130                 135                 140

Trp Phe Ile Asn Ala Arg Arg Arg Leu Leu Pro Asp Met Leu Arg Lys
145                 150                 155                 160

Asp Gly Lys Asp Pro Asn Gln Phe Thr Ile Ser Arg Arg Gly Ala Lys
                165                 170                 175

Ile Ser Glu Thr Ser Ser Val Glu Ser Val Met Gly Ile Lys Asn Phe
                180                 185                 190

Met Pro Ala Leu Glu Glu Thr Pro Phe His Ser Cys Thr Ala Gly Pro
                195                 200                 205

Asn Pro Thr Leu Gly Arg Pro Leu Ser Pro Lys Pro Ser Ser Pro Gly
210                 215                 220

Ser Val Leu Ala Arg Pro Ser Val Ile Cys His Thr Thr Val Thr Ala
225                 230                 235                 240

Leu Lys Asp Val Pro Phe Ser Leu Cys Gln Ser Val Gly Val Gly Gln
                245                 250                 255

Asn Thr Asp Ile Gln Gln Ile Ala Ala Lys Asn Phe Thr Asp Thr Ser
                260                 265                 270

Leu Met Tyr Pro Glu Asp Thr Cys Lys Ser Gly Pro Ser Thr Asn Thr
                275                 280                 285

Gln Ser Gly Leu Phe Asn Thr Pro Pro Thr Pro Pro Asp Leu Asn
290                 295                 300

Gln Asp Phe Ser Gly Phe Gln Leu Leu Val Asp Val Ala Leu Lys Arg
305                 310                 315                 320

Ala Ala Glu Met Glu Leu Gln Ala Lys Leu Thr Ala
                325                 330

<210> SEQ ID NO 8
<211> LENGTH: 1053
<212> TYPE: DNA
<213> ORGANISM: Homo Sapien

<400> SEQUENCE: 8
gtggtgcgaa tcctggagcg gcaaggccct cgggcagctc ctggggggtgc agacgatctc      60
agtgctgtgc gcaaccacac ttaccagatg ttgacactgc tggcagagga ccgtgcagtt     120
ccctcggccc ccacaggccc tgggcccctg ctggagtttg ctctgcacga ggatctgctg     180
acccgtgtgt tgcacatggc agctgcaatgg gatgagcttg ggatgggggt cgaggaacgg     240
cgggctgagc aactgaaact atttgaaatg ctagtgagcg aagctcgcca gccactgttg     300
cggcatggtc cagttcgtga ggctctgctc accctgctgg atgcctgtgg ccgccctgtg     360
cccagtagcc cagcactgga tgaaggcttg gtgctacttc tcagccagct gtgtgtttgt     420
gtggcccagg agccttcatt gctcgagttc ttcctgcagc cacctcctga gcctggagcc     480
gctccccgtc ttcttctctt ttctcgcctt gtcccttttg tgcatcgaga gggcacccctg     540
```

-continued

```
ggccagcagg cccgtgatgc cctacttctt ctcatggctt tgtcagctgg gagccccact    600
gtgggccgct acatcgcgga tcactcttac ttctgcccgg tgctggccac agggctcagt    660
gccctgtact catcactgcc tcgaaagatt gaggttccag gggatgattg cactgtctg     720 cgacgggaag actggctggg agtgccagcc cttgcactct tcatgagttc cctggagttc    780
tgcaatgcag taattcaggt ggctcacccc ctggtgcaga agcagttggt tgattatatc    840
cataatgggt tcctggtgcc tgtcatgggt cctgccttgc acaagacctc tgtggaggag    900
atgatcgcca gtaccgccta cctggaactt ttcctacgga gtatctcaga gcctgctttg    960
ctccgtacct tcctgcgatt cctgttgttg caccggcatg acacccacac catcctcgac    1020
accctcgttg ctcgtattgg cagtaactcc cgg                                 1053
```

<210> SEQ ID NO 9
<211> LENGTH: 351
<212> TYPE: PRT
<213> ORGANISM: Homo Sapien

<400> SEQUENCE: 9

```
Val Val Arg Ile Leu Glu Arg Gln Gly Pro Arg Ala Ala Pro Gly Gly
 1               5                  10                  15

Ala Asp Leu Ser Ala Val Arg Asn His Thr Tyr Gln Met Leu Thr
             20                  25                  30

Leu Leu Ala Glu Asp Arg Ala Val Pro Ser Ala Pro Thr Gly Pro Gly
         35                  40                  45

Pro Leu Leu Glu Phe Ala Leu His Glu Asp Leu Leu Thr Arg Val Leu
     50                  55                  60

Thr Trp Gln Leu Gln Trp Asp Glu Leu Gly Asp Gly Val Glu Glu Arg
 65                  70                  75                  80

Arg Ala Glu Gln Leu Lys Leu Phe Glu Met Leu Val Ser Glu Ala Arg
                 85                  90                  95

Gln Pro Leu Leu Arg His Gly Pro Val Arg Glu Ala Leu Leu Thr Leu
            100                 105                 110

Leu Asp Ala Cys Gly Arg Pro Val Pro Ser Ser Pro Ala Leu Asp Glu
        115                 120                 125

Gly Leu Val Leu Leu Ser Gln Leu Cys Val Cys Val Ala Gln Glu
    130                 135                 140

Pro Ser Leu Leu Glu Phe Phe Leu Gln Pro Pro Glu Pro Gly Ala
145                 150                 155                 160

Ala Pro Arg Leu Leu Phe Ser Arg Leu Val Pro Phe Val His Arg
                165                 170                 175

Glu Gly Thr Leu Gly Gln Gln Ala Arg Asp Ala Leu Leu Leu Met
            180                 185                 190

Ala Leu Ser Ala Gly Ser Pro Thr Val Gly Arg Tyr Ile Ala Asp His
        195                 200                 205

Ser Tyr Phe Cys Pro Val Leu Ala Thr Gly Leu Ser Ala Leu Tyr Ser
    210                 215                 220

Ser Leu Pro Arg Lys Ile Glu Val Pro Gly Asp Asp Trp His Cys Leu
225                 230                 235                 240

Arg Arg Glu Asp Trp Leu Gly Val Pro Ala Leu Ala Leu Phe Met Ser
                245                 250                 255

Ser Leu Glu Phe Cys Asn Ala Val Ile Gln Val Ala His Pro Leu Val
            260                 265                 270

Gln Lys Gln Leu Val Asp Tyr Ile His Asn Gly Phe Leu Val Pro Val
        275                 280                 285
```

```
Met Gly Pro Ala Leu His Lys Thr Ser Val Glu Met Ile Ala Ser
    290                 295                 300

Thr Ala Tyr Leu Glu Leu Phe Leu Arg Ser Ile Ser Glu Pro Ala Leu
305                 310                 315                 320

Leu Arg Thr Phe Leu Arg Phe Leu Leu His Arg His Asp Thr His
                325                 330                 335

Thr Ile Leu Asp Thr Leu Val Ala Arg Ile Gly Ser Asn Ser Arg
                340                 345                 350

<210> SEQ ID NO 10
<211> LENGTH: 1425
<212> TYPE: DNA
<213> ORGANISM: Homo Sapien

<400> SEQUENCE: 10
gggaaagaaa atgaggcccc aggacacctg ggttcacacc caggtcccca gcgatgtctc      60
caccaccgct gctgcaaccc ctgctgctgc tgctgcctct gctgaatgtg gagccttccg     120
gggccacact gatccgcatc cctcttcatc gagtccaacc tggacgcagg atcctgaacc     180
tactaggggg atggagagaa ccagcagagc tccccaagtt gggggcccca tcccctgggg     240
acaagcccat cttcgtacct ctctcgaact acagggatgt gcagtatttt ggggaaattg     300
ggctgggaac gcctccacaa aacttcactg ttgcctttga cactggctcc tccaatctct     360
gggtcccgtc caggagatgc cacttcttca gtgtgccctg ctggttacac caccgatttg     420
atcccaaagc ctctagctcc ttccaggcca atgggaccaa gtttgccatt caatatggaa     480
ctgggcgggt agatggaatc ctgagcgagg acaagctgac tattggtgga atcaagggtg     540
catcagtgat tttcggggag gctctctggg agcccagcct ggtcttcgct tttgcccatt     600
ttgatgggat attgggcctc ggttttccca ttctgtctgt ggaaggagtt cggccccga      660
tggatgtact ggtggagcag gggctattgg ataagcctgc cttctccttt tacctcaaca     720
gggaccctga agagcctgat ggaggagagc tggtcctggg gggctcggac ccggcacact     780
acatcccacc cctcaccttc gtgccagtca cggtccccgc ctactggcag atccacatgg     840
agcgtgtgaa ggtgggccca gggctgactc tctgtgccaa gggctgtgct gccatcctgg     900
atacgggcac gtccctcatc acaggaccca ctgaggagat ccgggccctg catgcagcca     960
ttgggggaat ccccttgctg gctggggagt acatcatcct gtgctcggaa atcccaaagc    1020
tccccgcagt ctccttcctt cttgggggggg tctggtttaa cctcacggcc catgattacg    1080
tcatccagac tactcgaaat ggcgtccgcc tctgcttgtc cggtttccag gccctggatg    1140
tccctccgcc tgcagggccc ttctggatcc tcggtgacgt cttcttgggg acgtatgtgg    1200
ccgtcttcga ccgcggggac atgaagagca gcgcccgggt gggcctggcg cgcgctcgca    1260
ctcgcggagc ggaccctcgga tggggagaga ctgcgcaggc gcagttcccc gggtgacgcc    1320
caagtgaagc gcatgcgcag cgggtggtcg cggaggtcct gctacccagt aaaaatccac    1380
tatttccatt gagcgaaaaa aaaaaaaaa aaaaaaaaa atcaa                       1425

<210> SEQ ID NO 11
<211> LENGTH: 433
<212> TYPE: PRT
<213> ORGANISM: Homo Sapien

<400> SEQUENCE: 11

Gly Pro Arg Thr Pro Gly Phe Thr Pro Arg Ser Pro Ala Met Ser Pro
1               5                   10                  15
```

```
Pro Pro Leu Leu Gln Pro Leu Leu Leu Leu Pro Leu Leu Asn Val
            20              25              30
Glu Pro Ser Gly Ala Thr Leu Ile Arg Ile Pro Leu His Arg Val Gln
        35              40              45
Pro Gly Arg Arg Ile Leu Asn Leu Leu Arg Gly Trp Arg Glu Pro Ala
    50              55              60
Glu Leu Pro Lys Leu Gly Ala Pro Ser Pro Gly Asp Lys Pro Ile Phe
65              70              75              80
Val Pro Leu Ser Asn Tyr Arg Asp Val Gln Tyr Phe Gly Glu Ile Gly
                85              90              95
Leu Gly Thr Pro Pro Gln Asn Phe Thr Val Ala Phe Asp Thr Gly Ser
            100             105             110
Ser Asn Leu Trp Val Pro Ser Arg Cys His Phe Ser Val Pro
        115             120             125
Cys Trp Leu His His Arg Phe Asp Pro Lys Ala Ser Ser Ser Phe Gln
    130             135             140
Ala Asn Gly Thr Lys Phe Ala Ile Gln Tyr Gly Thr Gly Arg Val Asp
145             150             155             160
Gly Ile Leu Ser Glu Asp Lys Leu Thr Ile Gly Ile Lys Gly Ala
                165             170             175
Ser Val Ile Phe Gly Glu Ala Leu Trp Glu Pro Ser Leu Val Phe Ala
            180             185             190
Phe Ala His Phe Asp Gly Ile Leu Gly Leu Gly Phe Pro Ile Leu Ser
        195             200             205
Val Glu Gly Val Arg Pro Pro Met Asp Val Leu Val Glu Gln Gly Leu
    210             215             220
Leu Asp Lys Pro Val Phe Ser Phe Tyr Leu Asn Arg Asp Pro Glu Glu
225             230             235             240
Pro Asp Gly Gly Glu Leu Val Leu Gly Gly Ser Asp Pro Ala His Tyr
                245             250             255
Ile Pro Pro Leu Thr Phe Val Pro Val Thr Val Pro Ala Tyr Trp Gln
            260             265             270
Ile His Met Glu Arg Val Lys Val Gly Pro Gly Leu Thr Leu Cys Ala
        275             280             285
Lys Gly Cys Ala Ala Ile Leu Asp Thr Gly Thr Ser Leu Ile Thr Gly
    290             295             300
Pro Thr Glu Glu Ile Arg Ala Leu His Ala Ala Ile Gly Gly Ile Pro
305             310             315             320
Leu Leu Ala Gly Glu Tyr Ile Ile Leu Cys Ser Glu Ile Pro Lys Leu
                325             330             335
Pro Ala Val Ser Phe Leu Leu Gly Gly Val Trp Phe Asn Leu Thr Ala
            340             345             350
His Asp Tyr Val Ile Gln Thr Thr Arg Asn Gly Val Arg Leu Cys Leu
        355             360             365
Ser Gly Phe Gln Ala Leu Asp Val Pro Pro Pro Ala Gly Pro Phe Trp
    370             375             380
Ile Leu Gly Asp Val Phe Leu Gly Thr Tyr Val Ala Val Phe Asp Arg
385             390             395             400
Gly Asp Met Lys Ser Ser Ala Arg Val Gly Leu Ala Arg Ala Arg Thr
                405             410             415
Arg Gly Ala Asp Leu Gly Trp Gly Glu Thr Ala Gln Ala Gln Phe Pro
            420             425             430
```

-continued

Gly

<210> SEQ ID NO 12
<211> LENGTH: 1242
<212> TYPE: DNA
<213> ORGANISM: Homo Sapien

<400> SEQUENCE: 12

| | | | | | |
|---|---|---|---|---|---|
| cggtgtgtgc | ggaacatggc | ggagcgcggc | aggaagcggc | cgtgcggccc | gggtgaacac | 60 |
| ggccaaagga | ttgagtggcg | aaaatggaag | caacagaaga | agaggagaa | aaaaaaatgg | 120 |
| aaggatctca | agctgatgaa | aaactggag | cggcagcggg | cacaggagga | acaggcaaag | 180 |
| cgcctggaag | aggaggaggc | agcggcagag | aaggaggacc | gcgggcggcc | ctacacactg | 240 |
| agcgtagccc | tgccgggctc | catcctggac | aatgctcagt | cgccggagct | tcgcacctac | 300 |
| ttggccggtc | agattgccag | agcctgtgcc | atcttctgtg | tggatgagat | cgtggtgttt | 360 |
| gatgaggagg | gccaggatgc | caagactgtg | gaggggaat | tcacaggagt | tgggaagaag | 420 |
| gggcaggcgt | gcgtacagct | ggcccggatc | ctgcagtacc | tggagtgtcc | acagtacctg | 480 |
| aggaaggcgt | tcttccccaa | gcaccaggat | ctacagtttg | cagggctcct | gaaccccctg | 540 |
| gacagccccc | accacatgcg | tcaggatgag | gaatccgagt | tccgagaggg | catcgtggtg | 600 |
| gatcggccca | cccggccagg | ccacggctcc | tttgtcaact | gtggcatgaa | aaaggaggtg | 660 |
| aagattgaca | agaacctgga | gcccgggctt | cgggtgactg | tgcgactgaa | ccagcagcag | 720 |
| cacccagact | gcaagaccta | ccatggcaaa | gtggtatcat | cgcaggaccc | tcgcaccaaa | 780 |
| gctggtctct | actggggcta | caccgtccga | ctggcttcct | gcctcagtgc | tgtgtttgct | 840 |
| gaggcccct | tccaagatgg | gtatgacctg | accatcggga | cgtcagagcg | cggctcagat | 900 |
| gtggcctctg | cccagcttcc | caacttcagg | catgctcttg | tggtgttcgg | gggcctccag | 960 |
| ggtctggaag | ctggagcgga | tgctgacccc | aacctggagg | tggctgaacc | cagtgtcctc | 1020 |
| tttgacctgt | acgtcaatac | ctgtcctggc | cagggtagcc | gtaccatccg | cacggaggaa | 1080 |
| gccatcctca | tctccctggc | cgccctgcag | cctggcctca | cccaggcggg | tgcccggcac | 1140 |
| acctgaaagt | tctaaggggc | cgaggacatc | agtgaagcag | cagtgaaacc | aggggctctg | 1200 |
| caggtcactt | gggacggacg | ccaccagact | tgtctccaaa | aa | | 1242 |

<210> SEQ ID NO 13
<211> LENGTH: 381
<212> TYPE: PRT
<213> ORGANISM: Homo Sapien

<400> SEQUENCE: 13

Arg Cys Val Arg Asn Met Ala Glu Arg Gly Arg Lys Arg Pro Cys Gly
1               5                   10                  15

Pro Gly Glu His Gly Gln Arg Ile Glu Trp Arg Lys Trp Lys Gln Gln
                20                  25                  30

Lys Lys Glu Glu Lys Lys Lys Trp Lys Asp Leu Lys Leu Met Lys Lys
            35                  40                  45

Leu Glu Arg Gln Arg Ala Gln Glu Gln Ala Lys Arg Leu Glu Glu
        50                  55                  60

Glu Glu Ala Ala Ala Glu Lys Glu Asp Arg Gly Arg Pro Tyr Thr Leu
65                  70                  75                  80

Ser Val Ala Leu Pro Gly Ser Ile Leu Asp Asn Ala Gln Ser Pro Glu
                85                  90                  95

Leu Arg Thr Tyr Leu Ala Gly Gln Ile Ala Arg Ala Cys Ala Ile Phe

```
                100               105                110
Cys Val Asp Glu Ile Val Val Phe Asp Glu Gly Gln Asp Ala Lys
        115                 120                 125

Thr Val Glu Gly Glu Phe Thr Gly Val Gly Lys Lys Gly Gln Ala Cys
    130                 135                 140

Val Gln Leu Ala Arg Ile Leu Gln Tyr Leu Glu Cys Pro Gln Tyr Leu
145                 150                 155                 160

Arg Lys Ala Phe Phe Pro Lys His Gln Asp Leu Gln Phe Ala Gly Leu
                165                 170                 175

Leu Asn Pro Leu Asp Ser Pro His His Met Arg Gln Asp Glu Glu Ser
            180                 185                 190

Glu Phe Arg Glu Gly Ile Val Val Asp Arg Pro Thr Arg Pro Gly His
        195                 200                 205

Gly Ser Phe Val Asn Cys Gly Met Lys Lys Glu Val Lys Ile Asp Lys
    210                 215                 220

Asn Leu Glu Pro Gly Leu Arg Val Thr Val Arg Leu Asn Gln Gln Gln
225                 230                 235                 240

His Pro Asp Cys Lys Thr Tyr His Gly Lys Val Val Ser Ser Gln Asp
                245                 250                 255

Pro Arg Thr Lys Ala Gly Leu Tyr Trp Gly Tyr Thr Val Arg Leu Ala
            260                 265                 270

Ser Cys Leu Ser Ala Val Phe Ala Glu Ala Pro Phe Gln Asp Gly Tyr
        275                 280                 285

Asp Leu Thr Ile Gly Thr Ser Glu Arg Gly Ser Asp Val Ala Ser Ala
    290                 295                 300

Gln Leu Pro Asn Phe Arg His Ala Leu Val Val Phe Gly Gly Leu Gln
305                 310                 315                 320

Gly Leu Glu Ala Gly Ala Asp Ala Asp Pro Asn Leu Glu Val Ala Glu
                325                 330                 335

Pro Ser Val Leu Phe Asp Leu Tyr Val Asn Thr Cys Pro Gly Gln Gly
            340                 345                 350

Ser Arg Thr Ile Arg Thr Glu Glu Ala Ile Leu Ile Ser Leu Ala Ala
        355                 360                 365

Leu Gln Pro Gly Leu Thr Gln Ala Gly Ala Arg His Thr
370                 375                 380

<210> SEQ ID NO 14
<211> LENGTH: 1779
<212> TYPE: DNA
<213> ORGANISM: Homo Sapien

<400> SEQUENCE: 14
cccggccacg gcttccgctg cgggccaccc caggattact cgcgtctggc tccaggcgcc      60
gagaaggcgc gctgggcgcc cgtggccgcc gcgccagctc ctcctcctcc cgctgctcct     120
gctcccgggg cgagcgcgca gccccgagcc cgccccgcgc ctcccggagc cctccccccc     180
gctgctccca tgcgcgcggg ctcgtccccg gccggcagca ccaagccttt tgtgcacgcc     240
gtgcccccct ctgacccect cgccaggcc aaccgcctgc caatcaaggt gctgaagatg     300
ctgacggcac gaactggcca cattttgcac cccgagtacc tgcagcccct gccttccacg     360
ccggtcagcc ccatcgagct cgatgccaag aagagcccgc tggcgctgtt ggcgcaaaca     420
tgttcgcaga tcgggaagcc cgaccccctcg ccctcctcca aactctcctc gaagtcggga     480
ttccgggtac cgagcgccac ctgccagcca ttcacgccca ggacaggcag cccgagctcc     540
```

```
agcgcctcgg cctgctcgcc gggaggtatg ctgtcctcgg ccgggggtgc cccggagggc      600
aaggacgaca agaaagacac cgacgtgggc ggcggtggca agggcaccgg gggcgcctcg      660
gccgaagggg gacccacggg gctggcacac ggccggatta gctgcggcgg cgggattaat      720
gtggatgtga accagcatcc ggatggggcc ccggaggcaa aggctctggg ctcggactgc      780
ggcggttcat cgggctccag ctccggctcc ggcccagcg cgcccacctc ctcctcagtg       840
ttgggctctg ggctggtggc tcccgtgtca ccctacaagc cgggccagac agtgttccct      900
ctgcctcccg cgggtatgac ctacccaggc agcctggccg gggcctacgc cggctacccg      960
ccccagttcc tgccacacgg cgtggcactt gaccccacca gccgggcag cctggtgggg     1020
gcgcagctgg cggcggccgc ggccgggtct ctgggctgca gtaagccggc cggctccagc     1080
cctttggccg gagcgtctcc gccgtccgtg atgacagcca gtttgtgccg ggaccccttac    1140
tgcctcagct accactgcgc tagccacctg gcagggcgg cggccgccag cgcttcttgc      1200
gcacatgatc cggctgctgc ggctgcggcg ctgaagtccg gatacccgct ggtgtacccc     1260
acgcacccgc tgcacggtgt gcactcctcg ctaacggccg ccgcggctgc tggcgccaca     1320
ccgcccctcc tggccggcca ccccctctac ccctacggct ttatgctccc taacgaccca     1380
ctcccccaca tctgcaactg ggtgtcggcc aacgggccgt gcgacaagcg cttcgccacg     1440
tccgaagagc tgctgagcca cttgcggacc catacggcat ttcccgggac agacaaactg     1500
ctgtcgggct accccagctc gtcgtctatg ccagcgctg ccgcggccgc catggcttgc      1560
cacatgcaca tccccacctc gggcgcaccg ggcagccctg gggacgctgg cgctgcgcag     1620
ccccaccac gcgctgggac tcagcagccg ctaccacccc tactccaaga gcccgcttcc      1680
cacgcctggc gccccgtgc cggtgcccgc cgccaccgga ccgtactact cccctacgc       1740
cctctacgga cagagactga ccaccgcctc ggcgctggg                            1779
```

<210> SEQ ID NO 15
<211> LENGTH: 593
<212> TYPE: PRT
<213> ORGANISM: Homo Sapien

<400> SEQUENCE: 15

```
Pro Gly His Gly Phe Arg Cys Gly Pro Pro Gln Asp Tyr Ser Arg Leu
1               5                   10                  15

Ala Pro Gly Ala Glu Lys Ala Arg Trp Ala Pro Val Ala Ala Ala Pro
            20                  25                  30

Ala Pro Pro Pro Ala Ala Pro Ala Pro Gly Ala Ser Ala Gln Pro
        35                  40                  45

Arg Ala Arg Pro Ala Pro Pro Gly Ala Leu Pro Ala Ala Pro Met
    50                  55                  60

Arg Ala Gly Ser Ser Pro Ala Gly Ser Thr Lys Pro Phe Val His Ala
65                  70                  75                  80

Val Pro Pro Ser Asp Pro Leu Arg Gln Ala Asn Arg Leu Pro Ile Lys
                85                  90                  95

Val Leu Lys Met Leu Thr Ala Arg Thr Gly His Ile Leu His Pro Glu
            100                 105                 110

Tyr Leu Gln Pro Leu Pro Ser Thr Pro Val Ser Pro Ile Glu Leu Asp
        115                 120                 125

Ala Lys Lys Ser Pro Leu Ala Leu Leu Ala Gln Thr Cys Ser Gln Ile
    130                 135                 140

Gly Lys Pro Asp Pro Ser Pro Ser Ser Lys Leu Ser Ser Lys Ser Gly
145                 150                 155                 160
```

-continued

```
Phe Arg Val Pro Ser Ala Thr Cys Gln Pro Phe Thr Pro Arg Thr Gly
                165                 170                 175
Ser Pro Ser Ser Ala Ser Ala Cys Ser Pro Gly Gly Met Leu Ser
            180                 185                 190
Ser Ala Gly Gly Ala Pro Glu Gly Lys Asp Lys Lys Asp Thr Asp
            195                 200                 205
Val Gly Gly Gly Lys Gly Thr Gly Ala Ser Ala Glu Gly Gly
    210                 215                 220
Pro Thr Gly Leu Ala His Gly Arg Ile Ser Cys Gly Gly Ile Asn
225                 230                 235                 240
Val Asp Val Asn Gln His Pro Asp Gly Gly Pro Gly Gly Lys Ala Leu
                245                 250                 255
Gly Ser Asp Cys Gly Gly Ser Ser Ser Ser Ser Gly Ser Gly Pro
                260                 265                 270
Ser Ala Pro Thr Ser Ser Ser Val Leu Gly Ser Gly Leu Val Ala Pro
            275                 280                 285
Val Ser Pro Tyr Lys Pro Gly Gln Thr Val Phe Pro Leu Pro Pro Ala
    290                 295                 300
Gly Met Thr Tyr Pro Gly Ser Leu Ala Gly Ala Tyr Ala Gly Tyr Pro
305                 310                 315                 320
Pro Gln Phe Leu Pro His Gly Val Ala Leu Asp Pro Thr Lys Pro Gly
                325                 330                 335
Ser Leu Val Gly Ala Gln Leu Ala Ala Ala Ala Gly Ser Leu Gly
            340                 345                 350
Cys Ser Lys Pro Ala Gly Ser Ser Pro Leu Ala Gly Ala Ser Pro Pro
            355                 360                 365
Ser Val Met Thr Ala Ser Leu Cys Arg Asp Pro Tyr Cys Leu Ser Tyr
    370                 375                 380
His Cys Ala Ser His Leu Ala Gly Ala Ala Ala Ser Ala Ser Cys
385                 390                 395                 400
Ala His Asp Pro Ala Ala Ala Ala Ala Leu Lys Ser Gly Tyr Pro
                405                 410                 415
Leu Val Tyr Pro Thr His Pro Leu His Gly Val His Ser Ser Leu Thr
            420                 425                 430
Ala Ala Ala Ala Ala Gly Ala Thr Pro Pro Ser Leu Ala Gly His Pro
            435                 440                 445
Leu Tyr Pro Tyr Gly Phe Met Leu Pro Asn Asp Pro Leu Pro His Ile
    450                 455                 460
Cys Asn Trp Val Ser Ala Asn Gly Pro Cys Asp Lys Arg Phe Ala Thr
465                 470                 475                 480
Ser Glu Glu Leu Leu Ser His Leu Arg Thr His Thr Ala Phe Pro Gly
                485                 490                 495
Thr Asp Lys Leu Leu Ser Gly Tyr Pro Ser Ser Ser Met Ala Ser
            500                 505                 510
Ala Ala Ala Ala Met Ala Cys His Met His Ile Pro Thr Ser Gly
            515                 520                 525
Ala Pro Gly Ser Pro Gly Asp Ala Gly Ala Ala Gln Pro Pro Arg
    530                 535                 540
Ala Gly Thr Gln Gln Pro Leu Pro Pro Leu Leu Gln Glu Pro Ala Ser
545                 550                 555                 560
His Ala Trp Arg Pro Arg Ala Gly Ala Arg Arg His Arg Thr Val Leu
                565                 570                 575
```

```
Leu Pro Leu Arg Pro Leu Arg Thr Glu Thr Asp His Arg Leu Gly Ala
        580                 585                 590
Gly

<210> SEQ ID NO 16
<211> LENGTH: 1938
<212> TYPE: DNA
<213> ORGANISM: Homo Sapien

<400> SEQUENCE: 16
gtttcctcgc cagagccccg gctggacacg cagcggctcg catcgcagag cgcagcgccg      60
gcgcggggcc gcgagaacgc agcgcagggg agcagcccga ggcggacacc gcgagccgcc     120
cggcactccc gcagtccagc cggctcctct agcccggcca cggctccgct gcgggccacc     180
caggattact cgcgtctggc tccaggcgcc gagaaggcgc gctgggcgcc cgtggccgcc     240
gcgccagctc ctcctcctcc cgctgctcct gctcccgggg cgagcgcgca gccccgagcc     300
cgccccgcgc ctcccggagc cctccccccc gctgctccca tgcgcgcggg ctcgtccccg     360
gccggcagca ccaagccttt tgtgcacgcc gtgcccccct ctgacccccct cgcgccaggcc    420 aaccgcctgc caatcaaggt gctgaagatg ctgacggcac gaactggcca cattttgcac     480
cccgagtacc tgcagcccct gccttccacg ccggtcagcc ccatcgagct cgatgccaag     540
aagagcccgc tggcgctgtt ggcgcaaaca tgttcgcaga tcgggaagcc cgaccctcg      600 ccctcctcca aactctcctc gaagtcggga ttccgggtac cgagcgccac ctgccagcca     660
ttcacgccca ggacaggcag cccgagctcc agcgcctcgg cctgctcgcc gggaggtatg     720
ctgtcctcgg ccgggggtgc cccggagggc aaggacgaca agaaagacac cgacgtgggc     780
ggcggtggca agggcaccgg gggcgcctcg gccgaagggg gacccacggg gctggcacac     840
ggccggatta gctgcggcgg cgggattaat gtggatgtga accagcatcc ggatgggggc     900
ccgggaggca aggctctggg ctcggactgc ggcggttcat cgggctccag ctccggctcc     960
ggccccagcg cgcccacctc ctcctcagtg ttgggctctg gctggtggc tcccgtgtca    1020 ccctacaagc cggccagac agtgttccct ctgcctcccg cgggtatgac ctacccaggc    1080
agcctggccg gggcctacgc cggctacccg ccccagttcc tgccacacgg cgtggcactt    1140
gaccccacca gccgggcag cctggtgggg gcgcagctgg cggcggccgc ggccgggtct    1200
ctgggctgca gtaagccggc cggctccagc cctttggccg gagcgtctcc gccgtccgtg    1260
atgacagcca gtttgtgccg ggaccccttac tgcctcagct accactgcgc tagccacctg    1320 gcagggggcgg cggccgccag cgcttcttgc gcacatgatc cggctgctgc ggctgcggcg    1380
ctgaagtccg gatacccgct ggtgtacccc acgcacccgc tgcacggtgt gcactcctcg    1440
ctaacggccg ccgcggctgc tggcgccaca ccgccctccc tggccggcca ccccctctac    1500
ccctacggct ttatgctccc taacgaccca ctcccccaca tctgcaactg ggtgtcggcc    1560
aacgggccgt gcgacaagcg cttcgccacg tccgaagagc tgctgagcca cttgcggacc    1620
catacggcat ttcccgggac agacaaactg ctgtcgggct accccagctc gtcgtctatg    1680
gccagcgctg ccgcggccgc catggcttgc cacatgcaca tccccacctc gggcgcaccg    1740
ggcagccctg ggacgctggc gctgcgcagc cccaccacg cgctgggact cagcagccgc    1800
taccacccct actccaagag cccgcttccc acgcctggcg ccccgtgcc ggtgcccgcc     1860 gccaccggac cgtactactc cccctacgcc ctctacggac agagactgac caccgcctcg    1920
gcgctggggt atcagtga                                                  1938
```

-continued

```
<210> SEQ ID NO 17
<211> LENGTH: 645
<212> TYPE: PRT
<213> ORGANISM: Homo Sapien

<400> SEQUENCE: 17

Val Ser Ser Pro Glu Pro Arg Leu Asp Thr Gln Arg Leu Ala Ser Gln
1               5                   10                  15

Ser Ala Ala Pro Ala Arg Gly Arg Glu Asn Ala Ala Gln Gly Ser Ser
            20                  25                  30

Pro Arg Arg Thr Pro Arg Ala Ala Arg His Ser Arg Ser Pro Ala Gly
        35                  40                  45

Ser Ser Ser Pro Ala Thr Ala Pro Leu Arg Ala Thr Gln Asp Tyr Ser
50                  55                  60

Arg Leu Ala Pro Gly Ala Glu Lys Ala Arg Trp Ala Pro Val Ala Ala
65                  70                  75                  80

Ala Pro Ala Pro Pro Pro Ala Ala Pro Ala Pro Gly Ala Ser Ala
                85                  90                  95

Gln Pro Arg Ala Arg Pro Ala Pro Pro Gly Ala Leu Pro Pro Ala Ala
            100                 105                 110

Pro Met Arg Ala Gly Ser Ser Pro Ala Gly Ser Thr Lys Pro Phe Val
        115                 120                 125

His Ala Val Pro Pro Ser Asp Pro Leu Arg Gln Ala Asn Arg Leu Pro
    130                 135                 140

Ile Lys Val Leu Lys Met Leu Thr Ala Arg Thr Gly His Ile Leu His
145                 150                 155                 160

Pro Glu Tyr Leu Gln Pro Leu Pro Ser Thr Pro Val Ser Pro Ile Glu
                165                 170                 175

Leu Asp Ala Lys Lys Ser Pro Leu Ala Leu Leu Ala Gln Thr Cys Ser
            180                 185                 190

Gln Ile Gly Lys Pro Asp Pro Ser Ser Lys Leu Ser Ser Lys
        195                 200                 205

Ser Gly Phe Arg Val Pro Ser Ala Thr Cys Gln Pro Phe Thr Pro Arg
    210                 215                 220

Thr Gly Ser Pro Ser Ser Ala Ser Ala Cys Ser Pro Gly Gly Met
225                 230                 235                 240

Leu Ser Ser Ala Gly Gly Ala Pro Glu Gly Lys Asp Lys Lys Asp
                245                 250                 255

Thr Asp Val Gly Gly Gly Lys Gly Thr Gly Ala Ser Ala Glu
            260                 265                 270

Gly Gly Pro Thr Gly Leu Ala His Gly Arg Ile Ser Cys Gly Gly Gly
        275                 280                 285

Ile Asn Val Asp Val Asn Gln His Pro Asp Gly Gly Pro Gly Gly Lys
    290                 295                 300

Ala Leu Gly Ser Asp Cys Gly Gly Ser Ser Gly Ser Ser Ser Gly Ser
305                 310                 315                 320

Gly Pro Ser Ala Pro Thr Ser Ser Val Leu Gly Ser Gly Leu Val
                325                 330                 335

Ala Pro Val Ser Pro Tyr Lys Pro Gly Gln Thr Val Phe Pro Leu Pro
            340                 345                 350

Pro Ala Gly Met Thr Tyr Pro Gly Ser Leu Ala Gly Ala Tyr Ala Gly
        355                 360                 365

Tyr Pro Pro Gln Phe Leu Pro His Gly Val Ala Leu Asp Pro Thr Lys
    370                 375                 380
```

-continued

```
Pro Gly Ser Leu Val Gly Ala Gln Leu Ala Ala Ala Ala Gly Ser
385                 390                 395                 400

Leu Gly Cys Ser Lys Pro Ala Gly Ser Ser Pro Leu Ala Gly Ala Ser
            405                 410                 415

Pro Pro Ser Val Met Thr Ala Ser Leu Cys Arg Asp Pro Tyr Cys Leu
            420                 425                 430

Ser Tyr His Cys Ala Ser His Leu Ala Gly Ala Ala Ala Ser Ala
            435                 440                 445

Ser Cys Ala His Asp Pro Ala Ala Ala Ala Leu Lys Ser Gly
    450                 455                 460

Tyr Pro Leu Val Tyr Pro Thr His Pro Leu His Gly Val His Ser Ser
465                 470                 475                 480

Leu Thr Ala Ala Ala Ala Gly Ala Thr Pro Pro Ser Leu Ala Gly
                485                 490                 495

His Pro Leu Tyr Pro Tyr Gly Phe Met Leu Pro Asn Asp Pro Leu Pro
            500                 505                 510

His Ile Cys Asn Trp Val Ser Ala Asn Gly Pro Cys Asp Lys Arg Phe
            515                 520                 525

Ala Thr Ser Glu Glu Leu Leu Ser His Leu Arg Thr His Thr Ala Phe
    530                 535                 540

Pro Gly Thr Asp Lys Leu Leu Ser Gly Tyr Pro Ser Ser Ser Ser Met
545                 550                 555                 560

Ala Ser Ala Ala Ala Ala Met Ala Cys His Met His Ile Pro Thr
                565                 570                 575

Ser Gly Ala Pro Gly Ser Pro Gly Thr Leu Ala Leu Arg Ser Pro His
            580                 585                 590

His Ala Leu Gly Leu Ser Ser Arg Tyr His Pro Tyr Ser Lys Ser Pro
    595                 600                 605

Leu Pro Thr Pro Gly Ala Pro Val Pro Val Pro Ala Ala Thr Gly Pro
    610                 615                 620

Tyr Tyr Ser Pro Tyr Ala Leu Tyr Gly Gln Arg Leu Thr Thr Ala Ser
625                 630                 635                 640

Ala Leu Gly Tyr Gln
                645
```

```
<210> SEQ ID NO 18
<211> LENGTH: 4022
<212> TYPE: DNA
<213> ORGANISM: Homo Sapien
<220> FEATURE:
<221> NAME/KEY: misc_feature
<222> LOCATION: (1)...(4022)
<223> OTHER INFORMATION: n = A,T,C or G

<400> SEQUENCE: 18
gccgagcacc gcgcaccgcg tcatgggggc cgcctcgggc cgccgggggc cggggctgct      60
gctgccgctg ccgctgctgt tgctgctgcc gccgcagccc gccctggcgt tggaccccgg     120
gctgcagccc ggcaactttt ctgctgacga ggccggggcg cagctcttcg cgcagagcta     180
caactccagc gccgaacagg tgctgttcca gagcgtggcc gccagctggg cgcacgacac     240
caacatcacc gcggagaatg ncnaaggcgc caggaggaag cagccctgct cagccaggag     300
tttgcggagg cctggggcca gaaggccaag gagctgtatg aaccgatctg cagaacttc      360 acggacccgc agctgcgcag gatcatcgga gctgtgcgca ccctgggctc tgccaacctg     420 ccctggcta agcggcagca gtacaacgcc ctgctaagca acatgagcag gatctactcc     480
```

-continued

```
accgccaagg tctgcctccc caacaagact gccacctgct ggtccctgga cccagatctc    540
accaacatcc tggcttcctc gcgaagctac gccatgctcc tgtttgcctg ggagggctgg    600
cacaacgctg cgggcatccc gctgaaaccg ctgtacgagg atttcactgc cctcagcaat    660
gaagcctaca agcaggacgg cttcacagac acgggggcct actggcgctc ctggtacaac    720
tcccccacct tcgaggacga tctggaacac ctctaccaac agctagagcc cctctacctg    780
aacctccatg ccttcgtccg ccgcgcactg catcgccgat acggagacag atacatcaac    840
ctcaggggac ccatccctgc tcatctgctg ggagacatgt gggcccagag ctgggaaaac    900
atctacgaca tggtggtgcc tttcccagac aagcccaacc tcgatgtcac cagtactatg    960
ctgcagcagg gctggaacgc cacgcacatg ttccgggtgg cagaggagtt cttcacctcc   1020
ctggagctct cccccatgcc tcccgagttc tgggaagggt cgatgctgga gaagccggcc   1080
gacgggcggg aagtggtgtg ccacgcctcg gcttgggact ctacaacag aaagacttc     1140
aggatcaagc agtgcacacg ggtcacgatg gaccagctct ccacagtgca ccatgagatg   1200
ggccatatac agtactacct gcagtacaag gatctgcccg tctccctgcg tcgggggggcc   1260
aaccccggct tccatgaggc cattggggac gtgctggcgc tctcggtctc cactcctgaa   1320
catctgcaca aaatcggcct gctggaccgt gtcaccaatg acacggaaag tgacatcaat   1380
tacttgctaa aaatggcact ggaaaaaatt gccttcctgc cctttggcta cttggtggac   1440
cagtggcgct gggggggtctt tagtgggcgt accccccctt cccgctacaa cttcgactgg   1500
tggtatcttc gaaccaagta tcaggggatc tgtcctcctg ttacccgaaa cgaaacccac   1560
tttgatgctg gagctaagtt tcatgttcca aatgtgacac catacatcag gtactttgtg   1620
agttttgtcc tgcagttcca gttccatgaa gccctgtgca aggaggcagg ctatgagggc   1680
ccactgcacc agtgtgacat ctaccggtcc accaaggcag gggccaagct ccggaaggtg   1740
ctgcaggctg gctcctccag gccctggcag gaggtgctga aggacatggt cggcttagat   1800
gccctggatg cccagccgct gctcaagtac ttccagccag tcacccagtg gctgcaggag   1860
cagaaccagc agaacggcga ggtcctgggc tggcccgagt accagtggca cccgccgttg   1920
cctgacaact acccggaggg catagacctg gtgactgatg aggctgaggc cagcaagttt   1980
gtggaggaat atgaccggac atcccaggtg gtgtggaacg agtatgccga ggccaactgg   2040
aactacaaca ccaacatcac cacagagacc agcaagattc tgctgcagaa gaacatgcaa   2100
atagccaacc acaccctgaa gtacggcacc caggccagga gtttgatgt gaaccagttg    2160
cagaacacca ctatcaagcg gatcataaag aaggttcagg acctagaacg ggcagcactg   2220
cctgcccagg agctggagga gtacaacaag atcctgttgg atatggaaac cacctacagc   2280
gtggccactg tgtgccaccc gaatggcagc tgcctgcagc tcgagccaga tctgacgaat   2340
gtgatggcca cgtcccggaa atatgaagac ctgttatggg catgggaggg ctggcgagac   2400
aaggcgggga gagccatcct ccagtttttac ccgaaatacg tggaactcat caaccaggct   2460
gcccggctca atggctatgt agatgcaggg gactcgtgga ggtctatgta cgagacacca   2520
tccctggagc aagacctgga gcggctcttc caggagctgc agccactcta cctcaacctg   2580
catgcctacg tgcgccgggc cctgcaccgt cactacgggg cccagcacat caacctggag   2640
gggcccattc ctgctcacct gctggggaac atgtgggcgc agacctggtc caacatctat   2700
gacttggtgg tgcccttccc ttcagccccc tcgatggaca ccacagaggc tatgctaaag   2760
cagggctgga cgcccaggag gatgtttaag gaggctgatg atttcttcac ctccctgggg   2820
```

-continued

```
ctgctgcccg tgcctcctga gttctggaac aagtcgatgc tggagaagcc aaccgacggg    2880
cgggaggtgg tctgccacgc ctcggcctgg gacttctaca acggcaagga cttccggatc    2940
aagcagtgca ccaccgtgaa cttggaggac ctggtggtgg cccaccacga aatgggccac    3000
atccagtatt tcatgcagta caaagactta cctgtggcct tgaggagggg tgccaacccc    3060
ggcttccatg aggccattgg ggacgtgcta gccctctcag tgtctacgcc caagcacctg    3120
cacagtctca acctgctgag cagtgagggt ggcagcgacg agcatgacat caactttctg    3180
atgaagatgg cccttgacaa gatcgccttt atccccttca gctacctcgt cgatcagtgg    3240
cgctggaggg tatttgatgg aagcatcacc aaggagaact ataaccagga gtggtggagc    3300
ctcaggctga agtaccaggg cctctgcccc ccagtgccca ggactcaagg tgactttgac    3360
ccaggggcca agttccacat tccttctagc gtgccttaca tcaggtactt tgtcagcttc    3420
atcatccagt tccagttcca cgaggcactg tgccaggcag ctggccacac gggccccctg    3480
cacaagtgtg acatctacca gtccaaggag gccgggcagc gcctggcgac cgccatgaag    3540
ctgggcttca gtaggccgtg gccggaagcc atgcagctga tcacgggcca gcccaacatg    3600
agcgcctcgg ccatgttgag ctacttcaag ccgctgctgg actggctccg cacggagaac    3660
gagctgcatg gggagaagct gggctggccg cagtacaact ggacgccgaa ctccgctcgc    3720
tcagaagggc ccctcccaga cagcggccgc gtcagcttcc tgggcctgga cctggatgcg    3780
cagcaggccc gcgtgggcca gtggctgctg ctcttcctgg gcatcgccct gctggtagcc    3840
accctgggcc tcagccagcg gctcttcagc atccgccacc gcagcctcca ccggcactcc    3900
cacgggcccc agttcggctc cgaggtggag ctgagacact cctgaggtga cccggctggg    3960
tcggccctgc ccaagggcct cccaccagag actgggatgg gaacactggt gggcagctga    4020
gg                                                                    4022
```

<210> SEQ ID NO 19
<211> LENGTH: 1265
<212> TYPE: PRT
<213> ORGANISM: Homo Sapien
<220> FEATURE:
<221> NAME/KEY: VARIANT
<222> LOCATION: (1)...(1265)
<223> OTHER INFORMATION: Xaa = Any Amino Acid

<400> SEQUENCE: 19

```
Arg Gly Arg Gly Ala Ala Leu Arg Ala Glu Leu Gln Leu Gln Arg Arg
1               5                   10                  15

Thr Gly Ala Val Pro Glu Arg Gly Arg Gln Leu Gly Ala Arg His Gln
            20                  25                  30

His His Arg Gly Glu Xaa Xaa Arg Arg Gln Glu Glu Ala Ala Leu Leu
        35                  40                  45

Ser Gln Glu Phe Ala Glu Ala Trp Gly Gln Lys Ala Lys Glu Leu Tyr
    50                  55                  60

Glu Pro Ile Trp Gln Asn Phe Thr Asp Pro Gln Leu Arg Arg Ile Ile
65                  70                  75                  80

Gly Ala Val Arg Thr Leu Gly Ser Ala Asn Leu Pro Leu Ala Lys Arg
                85                  90                  95

Gln Gln Tyr Asn Ala Leu Leu Ser Asn Met Ser Arg Ile Tyr Ser Thr
            100                 105                 110

Ala Lys Val Cys Leu Pro Asn Lys Thr Ala Thr Cys Trp Ser Leu Asp
        115                 120                 125

Pro Asp Leu Thr Asn Ile Leu Ala Ser Ser Arg Ser Tyr Ala Met Leu
```

-continued

```
            130                 135                 140
Leu Phe Ala Trp Glu Gly Trp His Asn Ala Ala Gly Ile Pro Leu Lys
145                 150                 155                 160

Pro Leu Tyr Glu Asp Phe Thr Ala Leu Ser Asn Glu Ala Tyr Lys Gln
                165                 170                 175

Asp Gly Phe Thr Asp Thr Gly Ala Tyr Trp Arg Ser Trp Tyr Asn Ser
                180                 185                 190

Pro Thr Phe Glu Asp Leu Glu His Leu Tyr Gln Gln Leu Glu Pro
                195                 200                 205

Leu Tyr Leu Asn Leu His Ala Phe Val Arg Arg Ala Leu His Arg Arg
210                 215                 220

Tyr Gly Asp Arg Tyr Ile Asn Leu Arg Gly Pro Ile Pro Ala His Leu
225                 230                 235                 240

Leu Gly Asp Met Trp Ala Gln Ser Trp Glu Asn Ile Tyr Asp Met Val
                245                 250                 255

Val Pro Phe Pro Asp Lys Pro Asn Leu Asp Val Thr Ser Thr Met Leu
                260                 265                 270

Gln Gln Gly Trp Asn Ala Thr His Met Phe Arg Val Ala Glu Glu Phe
                275                 280                 285

Phe Thr Ser Leu Glu Leu Ser Pro Met Pro Glu Phe Trp Glu Gly
                290                 295                 300

Ser Met Leu Glu Lys Pro Ala Asp Gly Arg Glu Val Val Cys His Ala
305                 310                 315                 320

Ser Ala Trp Asp Phe Tyr Asn Arg Lys Asp Phe Arg Ile Lys Gln Cys
                325                 330                 335

Thr Arg Val Thr Met Asp Gln Leu Ser Thr Val His His Glu Met Gly
                340                 345                 350

His Ile Gln Tyr Tyr Leu Gln Tyr Lys Asp Leu Pro Val Ser Leu Arg
                355                 360                 365

Arg Gly Ala Asn Pro Gly Phe His Glu Ala Ile Gly Asp Val Leu Ala
370                 375                 380

Leu Ser Val Ser Thr Pro Glu His Leu His Lys Ile Gly Leu Leu Asp
385                 390                 395                 400

Arg Val Thr Asn Asp Thr Glu Ser Asp Ile Asn Tyr Leu Leu Lys Met
                405                 410                 415

Ala Leu Glu Lys Ile Ala Phe Leu Pro Phe Gly Tyr Leu Val Asp Gln
                420                 425                 430

Trp Arg Trp Gly Val Phe Ser Gly Arg Thr Pro Pro Ser Arg Tyr Asn
                435                 440                 445

Phe Asp Trp Trp Tyr Leu Arg Thr Lys Tyr Gln Gly Ile Cys Pro Pro
450                 455                 460

Val Thr Arg Asn Glu Thr His Phe Asp Ala Gly Ala Lys Phe His Val
465                 470                 475                 480

Pro Asn Val Thr Pro Tyr Ile Arg Tyr Phe Val Ser Phe Val Leu Gln
                485                 490                 495

Phe Gln Phe His Glu Ala Leu Cys Lys Glu Ala Gly Tyr Glu Gly Pro
                500                 505                 510

Leu His Gln Cys Asp Ile Tyr Arg Ser Thr Lys Ala Gly Ala Lys Leu
                515                 520                 525

Arg Lys Val Leu Gln Ala Gly Ser Ser Arg Pro Trp Gln Glu Val Leu
530                 535                 540

Lys Asp Met Val Gly Leu Asp Ala Leu Asp Ala Gln Pro Leu Leu Lys
545                 550                 555                 560
```

-continued

Tyr Phe Gln Pro Val Thr Gln Trp Leu Gln Glu Gln Asn Gln Gln Asn
                565                 570                 575

Gly Glu Val Leu Gly Trp Pro Glu Tyr Gln Trp His Pro Pro Leu Pro
            580                 585                 590

Asp Asn Tyr Pro Glu Gly Ile Asp Leu Val Thr Asp Glu Ala Glu Ala
            595                 600                 605

Ser Lys Phe Val Glu Glu Tyr Asp Arg Thr Ser Gln Val Val Trp Asn
        610                 615                 620

Glu Tyr Ala Glu Ala Asn Trp Asn Tyr Asn Thr Asn Ile Thr Thr Glu
625                 630                 635                 640

Thr Ser Lys Ile Leu Leu Gln Lys Asn Met Gln Ile Ala Asn His Thr
                645                 650                 655

Leu Lys Tyr Gly Thr Gln Ala Arg Lys Phe Asp Val Asn Gln Leu Gln
                660                 665                 670

Asn Thr Thr Ile Lys Arg Ile Ile Lys Lys Val Gln Asp Leu Glu Arg
            675                 680                 685

Ala Ala Leu Pro Ala Gln Glu Leu Glu Glu Tyr Asn Lys Ile Leu Leu
        690                 695                 700

Asp Met Glu Thr Thr Tyr Ser Val Ala Thr Val Cys His Pro Asn Gly
705                 710                 715                 720

Ser Cys Leu Gln Leu Glu Pro Asp Leu Thr Asn Val Met Ala Thr Ser
                725                 730                 735

Arg Lys Tyr Glu Asp Leu Leu Trp Ala Trp Glu Gly Trp Arg Asp Lys
            740                 745                 750

Ala Gly Arg Ala Ile Leu Gln Phe Tyr Pro Lys Tyr Val Glu Leu Ile
            755                 760                 765

Asn Gln Ala Ala Arg Leu Asn Gly Tyr Val Asp Ala Gly Asp Ser Trp
        770                 775                 780

Arg Ser Met Tyr Glu Thr Pro Ser Leu Glu Gln Asp Leu Glu Arg Leu
785                 790                 795                 800

Phe Gln Glu Leu Gln Pro Leu Tyr Leu Asn Leu His Ala Tyr Val Arg
                805                 810                 815

Arg Ala Leu His Arg His Tyr Gly Ala Gln His Ile Asn Leu Glu Gly
                820                 825                 830

Pro Ile Pro Ala His Leu Leu Gly Asn Met Trp Ala Gln Thr Trp Ser
            835                 840                 845

Asn Ile Tyr Asp Leu Val Val Pro Phe Pro Ser Ala Pro Ser Met Asp
850                 855                 860

Thr Thr Glu Ala Met Leu Lys Gln Gly Trp Thr Pro Arg Arg Met Phe
865                 870                 875                 880

Lys Glu Ala Asp Asp Phe Phe Thr Ser Leu Gly Leu Leu Pro Val Pro
                885                 890                 895

Pro Glu Phe Trp Asn Lys Ser Met Leu Glu Lys Pro Thr Asp Gly Arg
            900                 905                 910

Glu Val Val Cys His Ala Ser Ala Trp Asp Phe Tyr Asn Gly Lys Asp
            915                 920                 925

Phe Arg Ile Lys Gln Cys Thr Thr Val Asn Leu Glu Asp Leu Val Val
        930                 935                 940

Ala His His Glu Met Gly His Ile Gln Tyr Phe Met Gln Tyr Lys Asp
945                 950                 955                 960

Leu Pro Val Ala Leu Arg Glu Gly Ala Asn Pro Gly Phe His Glu Ala
                965                 970                 975

-continued

```
Ile Gly Asp Val Leu Ala Leu Ser Val Ser Thr Pro Lys His Leu His
            980                 985                 990
Ser Leu Asn Leu Leu Ser Ser Glu Gly Gly Ser Asp Glu His Asp Ile
        995                 1000                1005
Asn Phe Leu Met Lys Met Ala Leu Asp Lys Ile Ala Phe Ile Pro Phe
        1010                1015                1020
Ser Tyr Leu Val Asp Gln Trp Arg Trp Arg Val Phe Asp Gly Ser Ile
1025                1030                1035                1040
Thr Lys Glu Asn Tyr Asn Gln Glu Trp Trp Ser Leu Arg Leu Lys Tyr
            1045                1050                1055
Gln Gly Leu Cys Pro Pro Val Pro Arg Thr Gln Gly Asp Phe Asp Pro
        1060                1065                1070
Gly Ala Lys Phe His Ile Pro Ser Ser Val Pro Tyr Ile Arg Tyr Phe
        1075                1080                1085
Val Ser Phe Ile Ile Gln Phe Gln Phe His Glu Ala Leu Cys Gln Ala
        1090                1095                1100
Ala Gly His Thr Gly Pro Leu His Lys Cys Asp Ile Tyr Gln Ser Lys
1105                1110                1115                1120
Glu Ala Gly Gln Arg Leu Ala Thr Ala Met Lys Leu Gly Phe Ser Arg
            1125                1130                1135
Pro Trp Pro Glu Ala Met Gln Leu Ile Thr Gly Gln Pro Asn Met Ser
        1140                1145                1150
Ala Ser Ala Met Leu Ser Tyr Phe Lys Pro Leu Leu Asp Trp Leu Arg
        1155                1160                1165
Thr Glu Asn Glu Leu His Gly Glu Lys Leu Gly Trp Pro Gln Tyr Asn
        1170                1175                1180
Trp Thr Pro Asn Ser Ala Arg Ser Glu Gly Pro Leu Pro Asp Ser Gly
1185                1190                1195                1200
Arg Val Ser Phe Leu Gly Leu Asp Leu Asp Ala Gln Gln Ala Arg Val
            1205                1210                1215
Gly Gln Trp Leu Leu Leu Phe Leu Gly Ile Ala Leu Leu Val Ala Thr
        1220                1225                1230
Leu Gly Leu Ser Gln Arg Leu Phe Ser Ile Arg His Arg Ser Leu His
        1235                1240                1245
Arg His Ser His Gly Pro Gln Phe Gly Ser Glu Val Glu Leu Arg His
        1250                1255                1260
Ser
1265

<210> SEQ ID NO 20
<211> LENGTH: 954
<212> TYPE: DNA
<213> ORGANISM: Homo Sapien

<400> SEQUENCE: 20
cgccggagga gttctgcgtc tcggggtggt gactgggtcc agaatggctt cggattcggg      60
gaaccagggg accctctgca cgttggagtt cgcggtgcag atgacctgtc agagctgtgt     120
ggacgcggtg cgcaaatccc tgcaagggg tggcaggtgtc caggatgtgg aggtgcactt     180
ggaggaccag atggtcttgg tacacaccac tctacccagc caggaggtgc aggctctcct     240
ggaaggcacg gggcggcagg cggtactcaa gggcatgggc agcggccagt tgcagaatct     300
gggggcagca gtggccatcc tggggggggcc tggcaccgtg cagggggtgg tgcgcttcct     360
acagctgacc cctgagcgct gcctcatcga gggaactatt gacggcctgg agcctgggct     420
```

| | |
|---|---|
| gcatggactc cacgtccatc agtacgggga ccttacaaac aactgcaaca gctgtgggaa | 480 |
| tcactttaac cctgatggag catctcatgg gggcccccag gactctgacc ggcaccgcgg | 540 |
| agacctgggc aatgtccgtg ctgatgctga cggccgcgcc atcttcagaa tggaggatga | 600 |
| gcagctgaag gtgtgggatg tgattggccg cagcctgatt attgatgagg gagaagatga | 660 |
| cctgggccgg ggaggccatc ccttatccaa gatcacaggg aactccgggg agaggttggc | 720 |
| ctgtggcatc attgcacgct ccgctggcct tttccagaac cccaagcaga tctgctcttg | 780 |
| cgatggcctc accatctggg aggagcgagg ccggcccatc gctggcaagg gcccgaaagg | 840 |
| agtcagcgca gccctgccc acctttgagc agacctcact ggctctgtt gctgtcctcc | 900 |
| agggcgagca ctttccactt ccagagggg ccagagggac tttgcctgcc cagt | 954 |

<210> SEQ ID NO 21
<211> LENGTH: 288
<212> TYPE: PRT
<213> ORGANISM: Homo Sapien

<400> SEQUENCE: 21

Ala Gly Gly Val Leu Arg Leu Gly Val Val Thr Gly Ser Arg Met Ala
1               5                   10                  15

Ser Asp Ser Gly Asn Gln Gly Thr Leu Cys Thr Leu Glu Phe Ala Val
            20                  25                  30

Gln Met Thr Cys Gln Ser Cys Val Asp Ala Val Arg Lys Ser Leu Gln
        35                  40                  45

Gly Val Ala Gly Val Gln Asp Val Glu Val His Leu Glu Asp Gln Met
    50                  55                  60

Val Leu Val His Thr Thr Leu Pro Ser Gln Glu Val Gln Ala Leu Leu
65                  70                  75                  80

Glu Gly Thr Gly Arg Gln Ala Val Leu Lys Gly Met Gly Ser Gly Gln
                85                  90                  95

Leu Gln Asn Leu Gly Ala Ala Val Ala Ile Leu Gly Gly Pro Gly Thr
            100                 105                 110

Val Gln Gly Val Val Arg Phe Leu Gln Leu Thr Pro Glu Arg Cys Leu
        115                 120                 125

Ile Glu Gly Thr Ile Asp Gly Leu Glu Pro Gly Leu His Gly Leu His
    130                 135                 140

Val His Gln Tyr Gly Asp Leu Thr Asn Asn Cys Asn Ser Cys Gly Asn
145                 150                 155                 160

His Phe Asn Pro Asp Gly Ala Ser His Gly Pro Gln Asp Ser Asp
                165                 170                 175

Arg His Arg Gly Asp Leu Gly Asn Val Arg Ala Asp Ala Asp Gly Arg
            180                 185                 190

Ala Ile Phe Arg Met Glu Asp Glu Gln Leu Lys Val Trp Asp Val Ile
        195                 200                 205

Gly Arg Ser Leu Ile Ile Asp Glu Gly Glu Asp Leu Gly Arg Gly
    210                 215                 220

Gly His Pro Leu Ser Lys Ile Thr Gly Asn Ser Gly Glu Arg Leu Ala
225                 230                 235                 240

Cys Gly Ile Ile Ala Arg Ser Ala Gly Leu Phe Gln Asn Pro Lys Gln
                245                 250                 255

Ile Cys Ser Cys Asp Gly Leu Thr Ile Trp Glu Glu Arg Gly Arg Pro
            260                 265                 270

Ile Ala Gly Lys Gly Pro Lys Gly Val Ser Ala Ala Pro Ala His Leu
        275                 280                 285

<210> SEQ ID NO 22
<211> LENGTH: 1006
<212> TYPE: DNA
<213> ORGANISM: Homo Sapien

<400> SEQUENCE: 22

```
atgggcctgg agctgtacct ggacctgctg tcccagccct gccgcgctgt ttacatcttt      60
gccaagaaga acgacattcc cttcgagctg cgcatcgtgg atctgattaa aggtcagcac     120
ttaagcgatg cctttgccca ggtgaacccc ctcaagaagg tgccagcctt gaaggacggg     180
gacttcacct tgacggagag tgtggccatc ctgctctacc tgacgcgcaa atataaggtc     240
cctgactact ggtaccctca ggacctgcag gcccgtgccc gtgtggatga gtacctggca     300
tggcagcaca cgactctgcg gagaagctgc tccgggcct tgtggcataa ggtgatgttc      360
cctgttttcc tgggtgagcc agtatctccc cagacactgg cagccaccct ggcagagttg     420
gatgtgaccc tgcagttgct cgaggacaag ttcctccaga caaggccttc cttactggt      480
cctcacatct ccttagctga cctcgtagca atcacggagc tgatgcatcc cgtgggtgct     540
ggctgccaag tcttcgaagg ccgacccaag ctggccacat ggcggcagcg cgtggaggca     600
gcagtggggg aggacctctt ccaggaggcc catgaggtca ttctgaaggc caaggacttc     660
ccacctgcag accccaccat aaagcagaag ctgatgccct gggtgctggc catgatccgg     720
tgagctggga acctcacccc ttgcaccgtc ctcagcagtc cacaaagcat tttcatttct     780
aatggcccat gggagccagg cccagaaagc aggaatggct gcttaagac ttgcccaagt      840
cccagagcac ctcacctccc gaagccacca tccccaccct gtcttccaca gccgcctgaa     900
agccacaatg agaatgatgc acactgaggc cttgtgtccc tttaatcact gcatttcatt     960
ttgattttgg ataataaacc tgggctcagc ctgagcctct gcttct                   1006
```

<210> SEQ ID NO 23
<211> LENGTH: 240
<212> TYPE: PRT
<213> ORGANISM: Homo Sapien

<400> SEQUENCE: 23

```
Met Gly Leu Glu Leu Tyr Leu Asp Leu Leu Ser Gln Pro Cys Arg Ala
1               5                   10                  15

Val Tyr Ile Phe Ala Lys Lys Asn Asp Ile Pro Phe Glu Leu Arg Ile
                20                  25                  30

Val Asp Leu Ile Lys Gly Gln His Leu Ser Asp Ala Phe Ala Gln Val
            35                  40                  45

Asn Pro Leu Lys Lys Val Pro Ala Leu Lys Asp Gly Asp Phe Thr Leu
        50                  55                  60

Thr Glu Ser Val Ala Ile Leu Leu Tyr Leu Thr Arg Lys Tyr Lys Val
65                  70                  75                  80

Pro Asp Tyr Trp Tyr Pro Gln Asp Leu Gln Ala Arg Ala Arg Val Asp
                85                  90                  95

Glu Tyr Leu Ala Trp Gln His Thr Thr Leu Arg Arg Ser Cys Leu Arg
                100                 105                 110

Ala Leu Trp His Lys Val Met Phe Pro Val Phe Leu Gly Glu Pro Val
            115                 120                 125

Ser Pro Gln Thr Leu Ala Ala Thr Leu Ala Glu Leu Asp Val Thr Leu
        130                 135                 140

Gln Leu Leu Glu Asp Lys Phe Leu Gln Asn Lys Ala Phe Leu Thr Gly
```

```
                145                 150                 155                 160
Pro His Ile Ser Leu Ala Asp Leu Val Ala Ile Thr Glu Leu Met His
                    165                 170                 175
Pro Val Gly Ala Gly Cys Gln Val Phe Glu Gly Arg Pro Lys Leu Ala
                180                 185                 190
Thr Trp Arg Gln Arg Val Glu Ala Val Gly Glu Asp Leu Phe Gln
        195                 200                 205
Glu Ala His Glu Val Ile Leu Lys Ala Lys Asp Phe Pro Pro Ala Asp
        210                 215                 220
Pro Thr Ile Lys Gln Lys Leu Met Pro Trp Val Leu Ala Met Ile Arg
225                 230                 235                 240

<210> SEQ ID NO 24
<211> LENGTH: 2442
<212> TYPE: DNA
<213> ORGANISM: Homo Sapien

<400> SEQUENCE: 24
atggctgcgg cggcccagct ctctctgaca cagttatcaa gtgggaatcc tgtatatgaa      60
aaatactata gacaggttga tacaggcaat actggaaggg tgttggcttc tgatgctgct     120
gctttcctga aaaatcagg gcttccagac ttgatacttg aaagatttg ggatttagcc      180
gacacagatg gcaaaggtat cctgaacaaa caagaattct ttgttgcttt gcgtcttgtg     240
gcatgtgccc agaatggatt ggaagtttca ctaagtagtt gaacctggc tgttcctcca      300
ccaagatttc ctgaagataa ggccaaatat gatgcaatat ttgatagttt aagcccagtg     360
aatggatttc tgtctggtga taaagtgaaa ccagtgttgc tcaactctaa gttacctgtg     420
gatatccttg aagagtttg ggagttgagt gatattgacc atgatggaat gcttgacaga      480
gatgagtttg cagttgccat gttttttggta tactgtgcac tggagaaaga acctgtgcca    540
atgtccttgc ctccagcctt ggtgccacca tctaagagaa aaacggtcag tatatcaggc     600
tctgtgcggt tgatcccctc ttcagcatca gccaaggaat cttaccactc cttaccatct     660
gtaggcattt tacctaccaa agcaccatta agacagtggg ttgtatcccc tgcagaaaaa     720
gctaaatatg atgaaatctt cctgaaaact gataaagata tggacggatt tgtgtctgga    780
ttggaggtcc gtgaaatatt cttgaaaaca ggtttacctt ctaccttact agcccatata     840
tggtcattat gcgacacaaa ggactgtggg aagcttttcaa aggatcagtt tgccttggct    900
tttcacttaa tcagtcagaa gttaatcaag gcattgatc ctcctcacgt tcttactcct      960
gaaatgattc caccatcaga cagggccagt ttacaaaaga acatcatagg atcaagtcct    1020
gttgcagatt tctctgctat taaggaacta gatactctta caatgaaat agttgaccta     1080
cagagggaaa agaataatgt ggaacaggac cttaaggaga aggaagatac tattaaacag     1140
aggacaagtg aggttcagga tcttcaagat gaagttcaaa gggagaatac taatctgcaa    1200
aaactacagg cccagaaaca gcaggtacag gaactccttg atgaactgga tgagcagaaa    1260
gcccagctgg aggagcaact caaggaagtc agaaagaaat gtgctgagga ggcccaactg    1320
atctcttctc tgaaagctga attaactagt caggaatcgc agatctccac ttatgaagaa    1380
gaattggcaa agctagaga gagctgagc cgtctacagc aagaaacagc agaattggag     1440
gagagtgtag agtcagggaa ggctcagttg gaacctcttc agcagcacct acaagattca    1500
caacaggaaa ttagttcaat gcaaatgaaa ctgatggaaa tgaaagattt ggaaaatcat    1560
aatagtcagt taaattggtg cagtagccca cacagcattc ttgtaaacgg agctacagat    1620
```

-continued

```
tattgcagcc tcagcaccag cagcagtgaa acagccaacc ttaatgaaca tgttgaaggc      1680
cagagcaacc tagagtctga gcccatacac caggaatctc catctgatcc ttttgttggc     1740
aatccatttg gtggtgatcc tttcaaaggt tcagatccat ttgcatcaga ctgtttcttc     1800
aggcaatcta ctgatccttt tgccacttca agcactgacc ctttcagtgc agccaacaat    1860
agcagtatta catcggtaga aacgttgaag cacaatgatc cttttgctcc tggtggaaca    1920
gttgttgcag caagcgattc agccacagac ccctttgctt ctgttttttgg gaatgaatca    1980 tttggaggtg gatttgctga cttcagcaca ttgtcaaagg tcaacaatga agatcctttt   2040
cgttcagcca catcgagctc tgtcagcaac gtagtgatta caaaaaatgt atttgaggaa    2100
acatcggtca aaagtgaaga tgaacccccca gcactgccac caaagatcgg aactccaaca  2160
agaccctgcc ctctaccacc tggcaacgat agccccaaag aaaaagatcc tgaaatgttt   2220
tgtgatccat tcacttctgc tactaccact accaataaag aggctgatcc aagcaatttt   2280
gccaacttca gtgcttatcc ctctgaagaa gatatgatcg aatgggccaa gagggaaagt    2340
gagagagagg aagagcagag gcttgcccga ctaaatcagc aggaacaaga agacttagaa    2400
ctggctattg cactcagcaa atctgagata tcagaagcat ga                       2442
```

<210> SEQ ID NO 25
<211> LENGTH: 813
<212> TYPE: PRT
<213> ORGANISM: Homo Sapien

<400> SEQUENCE: 25

```
Met Ala Ala Ala Gln Leu Ser Leu Thr Gln Leu Ser Ser Gly Asn
1               5                   10                  15

Pro Val Tyr Glu Lys Tyr Arg Gln Val Asp Thr Gly Asn Thr Gly
            20                  25                  30

Arg Val Leu Ala Ser Asp Ala Ala Phe Leu Lys Lys Ser Gly Leu
        35                  40                  45

Pro Asp Leu Ile Leu Gly Lys Ile Trp Asp Leu Ala Asp Thr Asp
    50                  55                  60

Lys Gly Ile Leu Asn Lys Gln Glu Phe Phe Val Ala Leu Arg Leu Val
65                  70                  75                  80

Ala Cys Ala Gln Asn Gly Leu Glu Val Ser Leu Ser Ser Leu Asn Leu
                85                  90                  95

Ala Val Pro Pro Pro Arg Phe Pro Glu Asp Lys Ala Lys Tyr Asp Ala
            100                 105                 110

Ile Phe Asp Ser Leu Ser Pro Val Asn Gly Phe Leu Ser Gly Asp Lys
        115                 120                 125

Val Lys Pro Val Leu Leu Asn Ser Lys Leu Pro Val Asp Ile Leu Gly
    130                 135                 140

Arg Val Trp Glu Leu Ser Asp Ile Asp His Asp Gly Met Leu Asp Arg
145                 150                 155                 160

Asp Glu Phe Ala Val Ala Met Phe Leu Val Tyr Cys Ala Leu Glu Lys
                165                 170                 175

Glu Pro Val Pro Met Ser Leu Pro Ala Leu Val Pro Pro Ser Lys
            180                 185                 190

Arg Lys Thr Val Ser Ile Ser Gly Ser Val Arg Leu Ile Pro Ser Ser
        195                 200                 205

Ala Ser Ala Lys Glu Ser Tyr His Ser Leu Pro Ser Val Gly Ile Leu
    210                 215                 220

Pro Thr Lys Ala Pro Leu Arg Gln Trp Val Val Ser Pro Ala Glu Lys
```

```
                225                 230                 235                 240
Ala Lys Tyr Asp Glu Ile Phe Leu Lys Thr Asp Lys Asp Met Asp Gly
                245                 250                 255
Phe Val Ser Gly Leu Glu Val Arg Glu Ile Phe Leu Lys Thr Gly Leu
            260                 265                 270
Pro Ser Thr Leu Leu Ala His Ile Trp Ser Leu Cys Asp Thr Lys Asp
            275                 280                 285
Cys Gly Lys Leu Ser Lys Asp Gln Phe Ala Leu Ala Phe His Leu Ile
        290                 295                 300
Ser Gln Lys Leu Ile Lys Gly Ile Asp Pro His Val Leu Thr Pro
305                 310                 315                 320
Glu Met Ile Pro Pro Ser Asp Arg Ala Ser Leu Gln Lys Asn Ile Ile
                325                 330                 335
Gly Ser Ser Pro Val Ala Asp Phe Ser Ala Ile Lys Glu Leu Asp Thr
                340                 345                 350
Leu Asn Asn Glu Ile Val Asp Leu Gln Arg Glu Lys Asn Asn Val Glu
            355                 360                 365
Gln Asp Leu Lys Glu Lys Glu Asp Thr Ile Lys Gln Arg Thr Ser Glu
    370                 375                 380
Val Gln Asp Leu Gln Asp Glu Val Gln Arg Glu Asn Thr Asn Leu Gln
385                 390                 395                 400
Lys Leu Gln Ala Gln Lys Gln Val Gln Glu Leu Leu Asp Glu Leu
                405                 410                 415
Asp Glu Gln Lys Ala Gln Leu Glu Glu Gln Leu Lys Glu Val Arg Lys
            420                 425                 430
Lys Cys Ala Glu Ala Gln Leu Ile Ser Ser Leu Lys Ala Glu Leu
        435                 440                 445
Thr Ser Gln Glu Ser Gln Ile Ser Thr Tyr Glu Glu Leu Ala Lys
    450                 455                 460
Ala Arg Glu Glu Leu Ser Arg Leu Gln Gln Glu Thr Ala Glu Leu Glu
465                 470                 475                 480
Glu Ser Val Glu Ser Gly Lys Ala Gln Leu Glu Pro Leu Gln Gln His
                485                 490                 495
Leu Gln Asp Ser Gln Gln Glu Ile Ser Ser Met Gln Met Lys Leu Met
            500                 505                 510
Glu Met Lys Asp Leu Glu Asn His Asn Ser Gln Leu Asn Trp Cys Ser
        515                 520                 525
Ser Pro His Ser Ile Leu Val Asn Gly Ala Thr Asp Tyr Cys Ser Leu
    530                 535                 540
Ser Thr Ser Ser Glu Thr Ala Asn Leu Asn Glu His Val Glu Gly
545                 550                 555                 560
Gln Ser Asn Leu Glu Ser Glu Pro Ile His Gln Glu Ser Pro Ser Asp
                565                 570                 575
Pro Phe Val Gly Asn Pro Phe Gly Asp Pro Phe Lys Gly Ser Asp
            580                 585                 590
Pro Phe Ala Ser Asp Cys Phe Arg Gln Ser Thr Asp Pro Phe Ala
        595                 600                 605
Thr Ser Ser Thr Asp Pro Phe Ser Ala Ala Asn Asn Ser Ser Ile Thr
    610                 615                 620
Ser Val Glu Thr Leu Lys His Asn Asp Pro Phe Ala Pro Gly Gly Thr
625                 630                 635                 640
Val Val Ala Ala Ser Asp Ser Ala Thr Asp Pro Phe Ala Ser Val Phe
                645                 650                 655
```

-continued

```
Gly Asn Glu Ser Phe Gly Gly Phe Ala Asp Phe Ser Thr Leu Ser
            660             665             670
Lys Val Asn Asn Glu Asp Pro Phe Arg Ser Ala Thr Ser Ser Ser Val
        675             680             685
Ser Asn Val Val Ile Thr Lys Asn Val Phe Glu Thr Ser Val Lys
        690             695             700
Ser Glu Asp Glu Pro Pro Ala Leu Pro Pro Lys Ile Gly Thr Pro Thr
705             710             715             720
Arg Pro Cys Pro Leu Pro Pro Gly Asn Asp Ser Pro Lys Glu Lys Asp
            725             730             735
Pro Glu Met Phe Cys Asp Pro Phe Thr Ser Ala Thr Thr Thr Thr Asn
        740             745             750
Lys Glu Ala Asp Pro Ser Asn Phe Ala Asn Phe Ser Ala Tyr Pro Ser
        755             760             765
Glu Glu Asp Met Ile Glu Trp Ala Lys Arg Glu Ser Glu Arg Glu Glu
    770             775             780
Glu Gln Arg Leu Ala Arg Leu Asn Gln Gln Glu Gln Glu Asp Leu Glu
785             790             795             800
Leu Ala Ile Ala Leu Ser Lys Ser Glu Ile Ser Glu Ala
            805             810

<210> SEQ ID NO 26
<211> LENGTH: 1357
<212> TYPE: DNA
<213> ORGANISM: Homo Sapien

<400> SEQUENCE: 26
cccggggccg gcggtgccgg ggtcatcggg atgatgcgga cgcagtgtct gctggggctg      60
cgcacgttcg tggccttcgc cgccaagctc tggagcttct tcatttacct tctgcggagg     120
cagatccgca cggtaattca gtaccaaact gttcgatatg atatcctccc cttatctcct     180
gtgtcccgga tcggctagcc caggtgaag aggaagatcc tggtgctgga tctggatgag     240
acacttattc actcccacca tgatggggtc ctgaggccca cagtccggcc tggtacgcct     300
cctgacttca tcctcaaggt ggtaatagac aaacatcctg tccggttttt tgtacataag     360
aggccccatg tggatttctt cctggaagtg gtgagccagt ggtacgagct ggtggtgttt     420
acagcaagca tggagatcta tggctctgct gtggcagata aactggacaa tagcagaagc     480
attcttaaga ggagatatta cagacagcac tgcactttgg agttgggcag ctacatcaag     540
gacctctctg tggtccacag tgacctctcc agcattgtga tcctggataa ctccccaggg     600
gcttacagga gccatccaga caatgccatc cccatcaaat cctggttcag tgaccccagc     660
gacacagccc ttctcaacct gctcccaatg ctggatgccc tcaggttcac cgctgatgtt     720
cgttccgtgc tgagccgaaa ccttcaccaa catcggctct ggtgacagct gctccccctc     780
cacctgagtt ggggtggggg ggaaagggag ggcgagccct gggatgccg tctgatgccc     840
tgtccaatgt gaggactgcc tgggcagggt ctgcccctcc caccctctc tgccctggga     900
gccctacact ccacttggga gtctggatgg acacatgggc caggggctct gaagcagcct     960
cactcttaac ttcgtgttca cactccatgg aaaccccaga ctgggacaca ggcggaagcc    1020
taggagagcc gaatcagtgt ttgtgaagag gcaggactgg ccagagtgac agacatacgg    1080
tgatccagga ggctcaaaga gaagccaagt cagctttgtt gtgatttgat ttttttttaaa   1140
aaactcttgt acaaaactga tctaattctt cactcctgct ccaagggctg ggctgtgggt    1200
```

-continued

```
gggatactgg gattttgggc cactggattt tccctaaatt tgtccccct ttactctccc    1260 tctatttttc tctccttaga ctccctcaga cctgtaacca gctttgtgtc ttttttcctt    1320
ttctctcttt taaaccatgc attataactt tgaaacc                            1357
```

<210> SEQ ID NO 27
<211> LENGTH: 254
<212> TYPE: PRT
<213> ORGANISM: Homo Sapien

<400> SEQUENCE: 27

```
Pro Gly Ala Gly Gly Ala Gly Val Ile Gly Met Met Arg Thr Gln Cys
1               5                   10                  15

Leu Leu Gly Leu Arg Thr Phe Val Ala Phe Ala Ala Lys Leu Trp Ser
            20                  25                  30

Phe Phe Ile Tyr Leu Leu Arg Arg Gln Ile Arg Thr Val Ile Gln Tyr
        35                  40                  45

Gln Thr Val Arg Tyr Asp Ile Leu Pro Leu Ser Pro Val Ser Arg Asn
    50                  55                  60

Arg Leu Ala Gln Val Lys Arg Lys Ile Leu Val Leu Asp Leu Asp Glu
65                  70                  75                  80

Thr Leu Ile His Ser His His Asp Gly Val Leu Arg Pro Thr Val Arg
                85                  90                  95

Pro Gly Thr Pro Pro Asp Phe Ile Leu Lys Val Val Ile Asp Lys His
            100                 105                 110

Pro Val Arg Phe Phe Val His Lys Arg Pro His Val Asp Phe Phe Leu
        115                 120                 125

Glu Val Val Ser Gln Trp Tyr Glu Leu Val Val Phe Thr Ala Ser Met
    130                 135                 140

Glu Ile Tyr Gly Ser Ala Val Ala Asp Lys Leu Asp Asn Ser Arg Ser
145                 150                 155                 160

Ile Leu Lys Arg Arg Tyr Tyr Arg Gln His Cys Thr Leu Glu Leu Gly
                165                 170                 175

Ser Tyr Ile Lys Asp Leu Ser Val Val His Ser Asp Leu Ser Ser Ile
            180                 185                 190

Val Ile Leu Asp Asn Ser Pro Gly Ala Tyr Arg Ser His Pro Asp Asn
        195                 200                 205

Ala Ile Pro Ile Lys Ser Trp Phe Ser Asp Pro Ser Asp Thr Ala Leu
    210                 215                 220

Leu Asn Leu Leu Pro Met Leu Asp Ala Leu Arg Phe Thr Ala Asp Val
225                 230                 235                 240

Arg Ser Val Leu Ser Arg Asn Leu His Gln His Arg Leu Trp
                245                 250
```

<210> SEQ ID NO 28
<211> LENGTH: 1812
<212> TYPE: DNA
<213> ORGANISM: Homo Sapien

<400> SEQUENCE: 28

```
atgccggccg tgagcctccc gcccaaggag aatgcgctct tcaagcggat cttgaggtgt     60
tatgaacata aacagtatag aaatggattg aaattctgta acaaatact ttctaatccc    120 aaatttgcag agcatggagg ttggcacgtt tatggccttc ttcagaggtc agacaagaag    180
tatgatgaag ccattaagtg ttacagaaat gcactaaaat gggataaaga caatcttcaa    240
atcttaaggg acctttcctt actacagatt caaatgcgag atcttgaggg ttacaggaca    300
```

```
tcccctgaca aggtggatta tgaatatagt gaactactct tatatcagaa tcaagttctt      360
cgggaagcag gtctctatag agaagctttg aacatctttt gtacctatga aaagcagatt      420
tgtgataaac ttgctgtaga agaaaccaaa ggggaacttc tgttgcaact atgtcgtttg      480
gaagatgctg cagatgttta tagaggattg caagagagaa atcctgaaaa ctgggcctat      540
tacaaaggct tggaaaaagc actcaagcca gctaatatgt tagaacggct aaaaatttat      600
gaggaagcct ggactaaata tcccagggga ctggtgccaa gaaggctgcc gttaaacttt      660
ttatctggtg agaagtttaa agaatgtttg gataagttcc taaggatgaa tttcagcaag      720
ggttgcccac cagtcttcaa tactttaaga tcattataca aagacaaaga aaaggtggca      780
atcatagaag agttagtagt aggttatgaa acctctctaa aaagctgccg gttatttaac      840
cccaatgatg atggaaagga ggaaccacca accacattac tttgggtcca gtactacttg      900
gcacaacatt atgacaaaat tggtcagcca tctattgctt tggagtacat aaatactgct      960
attgaaagta cacctacatt aatagaactc tttctcgtga aagctaaaat ctataagcat     1020
gctggaaata ttaaagaagc tgcaaggtgg atggatgagg cccaggcctt ggacacagca     1080
gacagattta tcaactccaa atgtgcaaaa tacatgctaa aagccaacct gattaaagaa     1140
gctgaagaaa tgtgctcaaa gtttacaagg aaggaacat cagcggtaga gaatttgaat      1200
gaaatgcagt gcatgtggtt ccaaacagaa tgtgcccagg cttataaagc aatgaataaa     1260
tttggtgaag cacttaagaa atgtcatgag attgagagac attttatag aatcactgat      1320 gaccagtttg actttcatac atactgtatg aggaagatta cccttagatc atatgtggac     1380
ttattaaaac tagaagatgt acttcgacag catccatttt acttcaaggc agcaagaatt     1440
gctatagaga tctatttgaa gcttcatgac aacccccta cagatgagaa taaagaacac     1500
gaagctgata cagctgccaa aatggtatat tacttagatc cttctagtca gaagcgagct     1560
atagagttgg caacaacact tgatgaatct ctcactaaca gaaacctcca gacatgtatg     1620
gaggtattgg aagccttgta tgatggtagc ctaggagact gtaaagaagc tgctgaaatt     1680
tatagagcaa attgtcataa gcttttccct tatgctttgg ctttcatgcc tcctggatat     1740
gaagaggata tgaagatcac agttaatgga gatagttctg cagaagctga agaactggcc     1800
aatgaaattt ga                                                          1812
```

<210> SEQ ID NO 29
<211> LENGTH: 603
<212> TYPE: PRT
<213> ORGANISM: Homo Sapien

<400> SEQUENCE: 29

```
Met Pro Ala Val Ser Leu Pro Pro Lys Glu Asn Ala Leu Phe Lys Arg
1               5                   10                  15

Ile Leu Arg Cys Tyr Glu His Lys Gln Tyr Arg Asn Gly Leu Lys Phe
            20                  25                  30

Cys Lys Gln Ile Leu Ser Asn Pro Lys Phe Ala Glu His Gly Gly Trp
        35                  40                  45

His Val Tyr Gly Leu Leu Gln Arg Ser Asp Lys Lys Tyr Asp Glu Ala
    50                  55                  60

Ile Lys Cys Tyr Arg Asn Ala Leu Lys Trp Asp Lys Asp Asn Leu Gln
65                  70                  75                  80

Ile Leu Arg Asp Leu Ser Leu Leu Gln Ile Gln Met Arg Asp Leu Glu
                85                  90                  95
```

```
Gly Tyr Arg Thr Ser Pro Asp Lys Val Asp Tyr Glu Tyr Ser Glu Leu
            100                 105                 110

Leu Leu Tyr Gln Asn Gln Val Leu Arg Glu Ala Gly Leu Tyr Arg Glu
            115                 120                 125

Ala Leu Glu His Leu Cys Thr Tyr Glu Lys Gln Ile Cys Asp Lys Leu
            130                 135                 140

Ala Val Glu Glu Thr Lys Gly Glu Leu Leu Gln Leu Cys Arg Leu
145                 150                 155                 160

Glu Asp Ala Ala Asp Val Tyr Arg Gly Leu Gln Glu Arg Asn Pro Glu
                165                 170                 175

Asn Trp Ala Tyr Tyr Lys Gly Leu Glu Lys Ala Leu Lys Pro Ala Asn
            180                 185                 190

Met Leu Glu Arg Leu Lys Ile Tyr Glu Glu Ala Trp Thr Lys Tyr Pro
            195                 200                 205

Arg Gly Leu Val Pro Arg Arg Leu Pro Leu Asn Phe Leu Ser Gly Glu
            210                 215                 220

Lys Phe Lys Glu Cys Leu Asp Lys Phe Leu Arg Met Asn Phe Ser Lys
225                 230                 235                 240

Gly Cys Pro Pro Val Phe Asn Thr Leu Arg Ser Leu Tyr Lys Asp Lys
            245                 250                 255

Glu Lys Val Ala Ile Ile Glu Glu Leu Val Val Gly Tyr Glu Thr Ser
            260                 265                 270

Leu Lys Ser Cys Arg Leu Phe Asn Pro Asn Asp Gly Lys Glu Glu
            275                 280                 285

Pro Pro Thr Thr Leu Leu Trp Val Gln Tyr Tyr Leu Ala Gln His Tyr
            290                 295                 300

Asp Lys Ile Gly Gln Pro Ser Ile Ala Leu Glu Tyr Ile Asn Thr Ala
305                 310                 315                 320

Ile Glu Ser Thr Pro Thr Leu Ile Glu Leu Phe Leu Val Lys Ala Lys
                325                 330                 335

Ile Tyr Lys His Ala Gly Asn Ile Lys Glu Ala Ala Arg Trp Met Asp
            340                 345                 350

Glu Ala Gln Ala Leu Asp Thr Ala Asp Arg Phe Ile Asn Ser Lys Cys
            355                 360                 365

Ala Lys Tyr Met Leu Lys Ala Asn Leu Ile Lys Glu Ala Glu Glu Met
            370                 375                 380

Cys Ser Lys Phe Thr Arg Glu Gly Thr Ser Ala Val Glu Asn Leu Asn
385                 390                 395                 400

Glu Met Gln Cys Met Trp Phe Gln Thr Glu Cys Ala Gln Ala Tyr Lys
                405                 410                 415

Ala Met Asn Lys Phe Gly Glu Ala Leu Lys Lys Cys His Glu Ile Glu
            420                 425                 430

Arg His Phe Ile Glu Ile Thr Asp Asp Gln Phe Asp Phe His Thr Tyr
            435                 440                 445

Cys Met Arg Lys Ile Thr Leu Arg Ser Tyr Val Asp Leu Leu Lys Leu
            450                 455                 460

Glu Asp Val Leu Arg Gln His Pro Phe Tyr Phe Lys Ala Ala Arg Ile
465                 470                 475                 480

Ala Ile Glu Ile Tyr Leu Lys Leu His Asp Asn Pro Leu Thr Asp Glu
                485                 490                 495

Asn Lys Glu His Glu Ala Asp Thr Ala Ala Lys Met Val Tyr Tyr Leu
            500                 505                 510

Asp Pro Ser Ser Gln Lys Arg Ala Ile Glu Leu Ala Thr Thr Leu Asp
```

```
                515                 520                 525
Glu Ser Leu Thr Asn Arg Asn Leu Gln Thr Cys Met Glu Val Leu Glu
    530                 535                 540

Ala Leu Tyr Asp Gly Ser Leu Gly Asp Cys Lys Glu Ala Ala Glu Ile
545                 550                 555                 560

Tyr Arg Ala Asn Cys His Lys Leu Phe Pro Tyr Ala Leu Ala Phe Met
                565                 570                 575

Pro Pro Gly Tyr Glu Glu Asp Met Lys Ile Thr Val Asn Gly Asp Ser
            580                 585                 590

Ser Ala Glu Ala Glu Glu Leu Ala Asn Glu Ile
            595                 600

<210> SEQ ID NO 30
<211> LENGTH: 1351
<212> TYPE: DNA
<213> ORGANISM: Homo Sapien

<400> SEQUENCE: 30
gcctcaggcc ggagcagccc catcatgccg agggagcgca gggagcggga tgcgaaggag      60
cgggacacca tgaaggagga cggcggcgcg gagttctcgg ctcgctccag gaagaggaag     120
gcaaacgtga ccgttgatcc agatgaagaa atggccaaaa tcgacaggac ggcgagggac     180
cagtgtggga gccagccttg gacaataat gcagtctgtg cagacccctg ctccctgatc      240
cccacacctg acaaagaaga tgatgaccgg gtttacccaa actcaacgtg caagcctcgg     300
attattgcac catccagagg ctccccgctg cctgtactga gctgggcaaa tagagaggaa     360
gtctggaaaa tcatgttaaa caaggaaaag acatacttaa gggatcagca ctttcttgag     420 caacacccte ttctgcagcc aaaaatgcga gcaattcttc tggattggtt aatggaggtg     480
tgtgaagtct ataaacttca cagggagacc ttttacttgg cacaagattt ctttgaccgg     540
tatatggcga cacaagaaaa tgttgtaaaa actcttttac agcttattgg gatttcatct     600
ttatttattg cagccaaact tgaggaaatc tatcctccaa agttgcacca gtttgcgtat     660
gtgacagatg gagcttgttc aggagatgaa attctcacca tggaattaat gattatgaag     720
gcccttaagt ggcgtttaag tcccctgact attgtgtcct ggctgaatgt atacatgcag     780
gttgcatatc taaatgactt acatgaagtg ctactgccgc agtatcccca gcaaatcttt     840
atacagattg cagagctgtt ggatctctgt gtcctggatg ttgactgcct tgaatttcct     900
tatggtatac ttgctgcttc ggccttgtat catttctcgt catctgaatt gatgcaaaag     960
gtttcagggt atcagtggtg cgacatagag aactgtgtca agtggatggt tccatttgcc    1020
atggttataa gggagacggg gagctcaaaa ctgaagcact tcagggcgt cgctgatgaa    1080 gatgcacaca acatacagac ccacagagac agcttggatt tgctggacaa agcccgagca    1140
aagaaagcca tgttgtctga acaaaatagg gcttctcctc tccccagtgg gctcctcacc    1200
ccgccacaga gcggtgttct gggctccgtt gtaccaagtg gagcaggtgg ttgcgggcaa    1260
gcgttgtgca gagcccatag ccagctgggc aggggctga cctctccaca ttatcagttg    1320
acagtgtaca atgcctttga tgaactgttt t                                  1351

<210> SEQ ID NO 31
<211> LENGTH: 451
<212> TYPE: PRT
<213> ORGANISM: Homo Sapien
<220> FEATURE:
<221> NAME/KEY: VARIANT
<222> LOCATION: (1)...(451)
```

<223> OTHER INFORMATION: Xaa = Any Amino Acid

<400> SEQUENCE: 31

```
Ala Ser Gly Arg Ser Ser Pro Ile Met Pro Arg Glu Arg Arg Glu Arg
1               5                   10                  15

Asp Ala Lys Glu Arg Asp Thr Met Lys Glu Asp Gly Gly Ala Glu Phe
            20                  25                  30

Ser Ala Arg Ser Arg Lys Arg Lys Ala Asn Val Thr Val Asp Pro Asp
        35                  40                  45

Glu Glu Met Ala Lys Ile Asp Arg Thr Ala Arg Asp Gln Cys Gly Ser
    50                  55                  60

Gln Pro Trp Asp Asn Asn Ala Val Cys Ala Asp Pro Cys Ser Leu Ile
65                  70                  75                  80

Pro Thr Pro Asp Lys Glu Asp Asp Arg Val Tyr Pro Asn Ser Thr
                85                  90                  95

Cys Lys Pro Arg Ile Ile Ala Pro Ser Arg Gly Ser Pro Leu Pro Val
                100                 105                 110

Leu Ser Trp Ala Asn Arg Glu Glu Val Trp Lys Ile Met Leu Asn Lys
            115                 120                 125

Glu Lys Thr Tyr Leu Arg Asp Gln His Phe Leu Glu Gln His Pro Leu
    130                 135                 140

Leu Gln Pro Lys Met Arg Ala Ile Leu Leu Asp Trp Leu Met Glu Val
145                 150                 155                 160

Cys Glu Val Tyr Lys Leu His Arg Glu Thr Phe Tyr Leu Ala Gln Asp
                165                 170                 175

Phe Phe Asp Arg Tyr Met Ala Thr Gln Glu Asn Val Val Lys Thr Leu
                180                 185                 190

Leu Gln Leu Ile Gly Ile Ser Ser Leu Phe Ile Ala Ala Lys Leu Glu
            195                 200                 205

Glu Ile Tyr Pro Pro Lys Leu His Gln Phe Ala Tyr Val Thr Asp Gly
    210                 215                 220

Ala Cys Ser Gly Asp Glu Ile Leu Thr Met Glu Leu Met Ile Met Lys
225                 230                 235                 240

Ala Leu Lys Trp Arg Leu Ser Pro Leu Thr Ile Val Ser Trp Leu Asn
                245                 250                 255

Val Tyr Met Gln Val Ala Tyr Leu Asn Asp Leu His Glu Val Leu Leu
                260                 265                 270

Pro Gln Tyr Pro Gln Gln Ile Phe Ile Gln Ile Ala Glu Leu Leu Asp
            275                 280                 285

Leu Cys Val Leu Asp Val Asp Cys Leu Glu Phe Pro Tyr Gly Ile Leu
    290                 295                 300

Ala Ala Ser Ala Leu Tyr His Phe Ser Ser Ser Glu Leu Met Gln Lys
305                 310                 315                 320

Val Ser Gly Tyr Gln Trp Cys Asp Ile Glu Asn Cys Val Lys Trp Met
                325                 330                 335

Val Pro Phe Ala Met Val Ile Arg Glu Thr Gly Ser Ser Lys Leu Lys
                340                 345                 350

His Phe Arg Gly Val Ala Asp Glu Asp Ala His Asn Ile Gln Thr His
            355                 360                 365

Arg Asp Ser Leu Asp Leu Leu Asp Lys Ala Arg Ala Lys Lys Ala Met
    370                 375                 380

Leu Ser Glu Gln Asn Arg Ala Ser Pro Leu Pro Ser Gly Leu Leu Thr
385                 390                 395                 400
```

```
Pro Pro Gln Ser Gly Val Leu Gly Ser Val Val Pro Ser Gly Ala Gly
            405                 410                 415
Gly Cys Gly Gln Ala Leu Cys Arg Ala His Ser Gln Leu Gly Arg Gly
            420                 425                 430
Leu Thr Ser Pro His Tyr Gln Leu Thr Val Tyr Asn Ala Phe Asp Glu
            435                 440                 445
Leu Phe Xaa
    450

<210> SEQ ID NO 32
<211> LENGTH: 3750
<212> TYPE: DNA
<213> ORGANISM: Homo Sapien

<400> SEQUENCE: 32
```

| | | | | | |
|---|---|---|---|---|---|
| gatctgtctg | gctccattga | tgacctcccc | acgggaacgg | aagcaacttt | gagctcagca | 60 |
| gtcagtgcat | ccgggtccac | gagcagccaa | ggggatcaga | gcaacccggc | gcagtcgcct | 120 |
| ttctccccac | atgcgtcccc | tcatctctcc | agcatcccgg | ggggcccatc | tccctctcct | 180 |
| gttggctctc | ctgtaggaag | caaccagtct | cgatctggcc | caatctctcc | tgcaagtatc | 240 |
| ccaggtttta | tggcaggcac | acaaagaaac | cctcagatgg | ctcagtatgg | acctcaacag | 300 |
| acaggaccat | ccatgtcgcc | tcatccttct | cctgggggcc | agatgcatgc | tggaatcagt | 360 |
| agctttcagc | agagtaactc | aagtgggact | tacggtccac | agatgagcca | gtatggacca | 420 |
| caaggtaact | actccagacc | cccagcgtat | agtggggtgc | ccagtgcaag | ctacagcggc | 480 |
| ccagggcccg | gtatgggtat | cagtgccaac | aaccagatgc | atggacaagg | gccaagccag | 540 |
| ccatgtggtg | ctgtgcccct | gggacgaatg | ccatcagctg | ggatgcagaa | cagaccattt | 600 |
| cctggaaata | tgagcagcat | gaccccagt | tctcctggca | tgtctcagca | gggagggcca | 660 |
| ggaatggggc | cgccaatgcc | aactgtgaac | cgtaaggcac | aggaggcagc | cgcagcagtg | 720 |
| atgcaggctg | ctgcgaactc | agcacaaagc | aggtacgcca | cccaggagca | cgccccgggc | 780 |
| aggcaaggca | gtttccccgg | catgaaccag | agtggactta | tggcttccag | ctctcccctac | 840 |
| agccagccca | tgaacaacag | ctctagcctg | atgaacacgg | aggcgccgcc | ctacagcatg | 900 |
| gcgcccgcca | tggtgaacag | ctcggcagca | tctgtgggtc | ttgcagatat | gatgtctcct | 960 |
| ggtgaatcca | aactgcccct | gcctctcaaa | gcagacggca | agaagaagg | cactccacag | 1020 |
| cccgagagca | agtcaaagga | tagctacagc | tctcagggta | tttctcagcc | cccaaccccca | 1080 |
| ggcaacctgc | cagtcccttc | cccaatgtcc | cccagctctg | ctagcatctc | ctcatttcat | 1140 |
| ggagatgaaa | gtgatagcat | tagcagccca | ggctggccaa | agactccatc | aagccctaag | 1200 |
| tccagctcct | ccaccactac | tggggagaag | atcacgaagg | tgtacgagct | ggggaatgag | 1260 |
| ccagagagaa | agctctgggt | cgaccgatac | ctcaccttca | tggaagagag | aggctctcct | 1320 |
| gtctcaagtc | tgcctgccgt | gggcaagaag | cccctggacc | tgttccgact | ctacgtctgc | 1380 |
| gtcaaagaga | tcgggggttt | ggcccaggtt | aataaaaaca | agaagtggcg | tgagctggca | 1440 |
| accaacctaa | acgttggcac | ctcaagcagt | gcagcgagct | ccatgaaaaa | gcagtatatt | 1500 |
| cagtacctgt | ttgcctttga | gagcaagatc | gaacctaact | cgggatcctt | gcaaggccca | 1560 |
| cagaccccc | agtcaactgg | cagcaattcc | atggcagagg | ttccaggtga | cctgaagcca | 1620 |
| cctaccccag | cctccacccc | tcacggccag | atgactccaa | tgcaaggtgg | aagaagcagt | 1680 |
| acaatcagtg | tgcacgaccc | attctcagat | gtgagtgatt | catccttccc | gaaacggaac | 1740 |
| tccatgactc | caaacgcccc | ctaccagcag | ggcatgagca | tgcccgatgt | gatgggcagg | 1800 |

```
atgccctatg agcccaacaa ggacccctt gggggaatga aaaagtgcc tggaagcagc      1860 gagcccttta tgacgcaagg acagatgccc aacagcagca tgcaggacat gtacaaccaa      1920
agtccctccg gagcaatgtc taacctgggc atggggcagc gccagcagtt tccctatgga      1980
gccagttacg accgaagcac tgttgctact ttcaatctct cccagttgtc tggatttctc      2040
gaacttttag tcgagtactt tagaaaatgc ctgattgaca tttttggaat tcttatggaa      2100
tatgaagtgg gagaccccag ccaaaaagca cttgatcaca acgcagcaag gaaggatgac      2160
agccagtcct tggcagacga ttctgggaaa gaggaggaag atgctgaatg tattgatgac      2220
gacgaggaag acgaggagga tgaggaggaa gacagcgaga agacagaaag cgatgaaaag      2280
agcagcatcg ctctgactgc cccggacgcc gctgcagacc caaaggagaa gcccaagcaa      2340
gccagtaagt tcgacaagct gccaataaag atagtcaaaa gaacaaccct gtttgttgtt      2400
gaccgatctg acaagttggg gcgtgtgcag gagttcaata gtggccttct gcactggcag      2460
ctcggcgggg gtgacaccac cgagcacatt cagactcact ttgagagcaa gatggaaatt      2520
cctcctcgca ggcgcccacc tcccccctta agctccgcag gtagaaagaa agagcaagaa      2580
ggcaaaggcg actctgaaga gcagcaagag aaaagcatca tagcaaccat cgatgacgtc      2640
ctctctgctc ggccaggggc attgcctgaa gacgcaaacc ctgggcccca gaccgaaagc      2700
agtaagtttc cctttggtat ccagcaagcc aaaagtcacc ggaacatcaa gctgctggag      2760
gacgagccca ggagccgaga cgagactcct ctgtgtacca tcgcgcactg gcaggactcg      2820
ctggctaagc gatgcatctg tgtgtccaat attgtccgta gcttgtcatt cgtgcctggc      2880
aatgatgccg aaatgtccaa acatccaggc ctggtgctga tcctggggaa gctgattctt      2940
cttcaccacg agcatccaga gagaaagcga gcaccgcaga cctatgagaa agaggaggat      3000
gaggacaagg gggtggcctg cagcaaagat gagtggtggt gggactgcct cgaggtcttg      3060
agggataaca cgttggtcac gttggccaac atttccgggc agctagactt gtctgcttac      3120
acggaaagca tctgcttgcc aattttggat ggcttgctgc actggatggt gtgcccgtct      3180
gcagaggcac aagatccctt tccaactgtg gacccaact cggtcctgtc gcctcagaga      3240
cttgtgctgg agaccctctg taaactcagt atccaggaca ataatgtgga cctgatcttg      3300
gccactcctc catttagtcg tcaggagaaa ttctatgcta cattagttag gtacgttggg      3360
gatcgcaaaa acccagtctg tcgagaaatg tccatggcgc ttttatcgaa ccttgcccaa      3420
ggggacgcac tagcagcaag ggccatagct gtgcagaaag gaagcattgg aaacttgata      3480
agcttcctag aggatggggt cacgatggcc cagtaccagc agagccagca caacctcatg      3540
cacatgcagc ccccgcccct ggaaccacct agcgtagaca tgatgtgcag ggcggccaag      3600
gctttgctag ccatggccag agtggacgaa aaccgctcgg aattccttt gcacgagggc      3660 cggttgctgg atatctcgat atcagctgtc ctgaactctc tggttgcatc tgtcatctgt      3720
gatgtactgt ttcagattgg gcagttatga                                      3750
```

<210> SEQ ID NO 33
<211> LENGTH: 1249
<212> TYPE: PRT
<213> ORGANISM: Homo Sapien

<400> SEQUENCE: 33

```
Asp Leu Ser Gly Ser Ile Asp Asp Leu Pro Thr Gly Thr Glu Ala Thr
1               5                   10                  15

Leu Ser Ser Ala Val Ser Ala Ser Gly Ser Thr Ser Ser Gln Gly Asp
```

```
                    20                  25                  30
Gln Ser Asn Pro Ala Gln Ser Pro Phe Ser Pro His Ala Ser Pro His
                35                  40                  45
Leu Ser Ser Ile Pro Gly Gly Pro Ser Pro Ser Pro Val Gly Ser Pro
 50                  55                  60
Val Gly Ser Asn Gln Ser Arg Ser Gly Pro Ile Ser Pro Ala Ser Ile
 65                  70                  75                  80
Pro Gly Phe Met Ala Gly Thr Gln Arg Asn Pro Gln Met Ala Gln Tyr
                 85                  90                  95
Gly Pro Gln Gln Thr Gly Pro Ser Met Ser Pro His Pro Ser Pro Gly
                100                 105                 110
Gly Gln Met His Ala Gly Ile Ser Ser Phe Gln Gln Ser Asn Ser Ser
                115                 120                 125
Gly Thr Tyr Gly Pro Gln Met Ser Gln Tyr Gly Pro Gln Gly Asn Tyr
                130                 135                 140
Ser Arg Pro Pro Ala Tyr Ser Gly Val Pro Ala Ser Tyr Ser Gly
145                 150                 155                 160
Pro Gly Pro Gly Met Gly Ile Ser Ala Asn Asn Gln Met His Gly Gln
                165                 170                 175
Gly Pro Ser Gln Pro Cys Gly Ala Val Pro Leu Gly Arg Met Pro Ser
                180                 185                 190
Ala Gly Met Gln Asn Arg Pro Phe Pro Gly Asn Met Ser Ser Met Thr
                195                 200                 205
Pro Ser Ser Pro Gly Met Ser Gln Gln Gly Gly Pro Gly Met Gly Pro
                210                 215                 220
Pro Met Pro Thr Val Asn Arg Lys Ala Gln Glu Ala Ala Ala Val
225                 230                 235                 240
Met Gln Ala Ala Ala Asn Ser Ala Gln Ser Arg Tyr Ala Thr Gln Glu
                245                 250                 255
His Ala Pro Gly Arg Gln Gly Ser Phe Pro Gly Met Asn Gln Ser Gly
                260                 265                 270
Leu Met Ala Ser Ser Ser Pro Tyr Ser Gln Pro Met Asn Asn Ser Ser
                275                 280                 285
Ser Leu Met Asn Thr Gln Ala Pro Pro Tyr Ser Met Ala Pro Ala Met
                290                 295                 300
Val Asn Ser Ser Ala Ala Ser Val Gly Leu Ala Asp Met Met Ser Pro
305                 310                 315                 320
Gly Glu Ser Lys Leu Pro Leu Pro Leu Lys Ala Asp Gly Lys Glu Glu
                325                 330                 335
Gly Thr Pro Gln Pro Glu Ser Lys Ser Lys Asp Ser Tyr Ser Ser Gln
                340                 345                 350
Gly Ile Ser Gln Pro Pro Thr Pro Gly Asn Leu Pro Val Pro Ser Pro
                355                 360                 365
Met Ser Pro Ser Ser Ala Ser Ile Ser Ser Phe His Gly Asp Glu Ser
                370                 375                 380
Asp Ser Ile Ser Ser Pro Gly Trp Pro Lys Thr Pro Ser Ser Pro Lys
385                 390                 395                 400
Ser Ser Ser Ser Thr Thr Thr Gly Glu Lys Ile Thr Lys Val Tyr Glu
                405                 410                 415
Leu Gly Asn Glu Pro Glu Arg Lys Leu Trp Val Asp Arg Tyr Leu Thr
                420                 425                 430
Phe Met Glu Glu Arg Gly Ser Pro Val Ser Ser Leu Pro Ala Val Gly
                435                 440                 445
```

-continued

```
Lys Lys Pro Leu Asp Leu Phe Arg Leu Tyr Val Cys Val Lys Glu Ile
    450                 455                 460
Gly Gly Leu Ala Gln Val Asn Lys Asn Lys Lys Trp Arg Glu Leu Ala
465                 470                 475                 480
Thr Asn Leu Asn Val Gly Thr Ser Ser Ala Ala Ser Ser Met Lys
                485                 490                 495
Lys Gln Tyr Ile Gln Tyr Leu Phe Ala Phe Glu Ser Lys Ile Glu Pro
                500                 505                 510
Asn Ser Gly Ser Leu Gln Gly Pro Gln Thr Pro Gln Ser Thr Gly Ser
                515                 520                 525
Asn Ser Met Ala Glu Val Pro Gly Asp Leu Lys Pro Pro Thr Pro Ala
                530                 535                 540
Ser Thr Pro His Gly Gln Met Thr Pro Met Gln Gly Gly Arg Ser Ser
545                 550                 555                 560
Thr Ile Ser Val His Asp Pro Phe Ser Asp Val Ser Asp Ser Ser Phe
                565                 570                 575
Pro Lys Arg Asn Ser Met Thr Pro Asn Ala Pro Tyr Gln Gln Gly Met
                580                 585                 590
Ser Met Pro Asp Val Met Gly Arg Met Pro Tyr Glu Pro Asn Lys Asp
                595                 600                 605
Pro Phe Gly Gly Met Arg Lys Val Pro Gly Ser Ser Glu Pro Phe Met
                610                 615                 620
Thr Gln Gly Gln Met Pro Asn Ser Ser Met Gln Asp Met Tyr Asn Gln
625                 630                 635                 640
Ser Pro Ser Gly Ala Met Ser Asn Leu Gly Met Gly Gln Arg Gln Gln
                645                 650                 655
Phe Pro Tyr Gly Ala Ser Tyr Asp Arg Ser Thr Val Ala Thr Phe Asn
                660                 665                 670
Leu Ser Gln Leu Ser Gly Phe Leu Glu Leu Leu Val Glu Tyr Phe Arg
                675                 680                 685
Lys Cys Leu Ile Asp Ile Phe Gly Ile Leu Met Glu Tyr Glu Val Gly
                690                 695                 700
Asp Pro Ser Gln Lys Ala Leu Asp His Asn Ala Ala Arg Lys Asp Asp
705                 710                 715                 720
Ser Gln Ser Leu Ala Asp Asp Ser Gly Lys Glu Glu Asp Ala Glu
                725                 730                 735
Cys Ile Asp Asp Asp Glu Glu Asp Glu Glu Asp Glu Glu Asp Ser
                740                 745                 750
Glu Lys Thr Glu Ser Asp Glu Lys Ser Ser Ile Ala Leu Thr Ala Pro
                755                 760                 765
Asp Ala Ala Ala Asp Pro Lys Glu Lys Pro Lys Gln Ala Ser Lys Phe
                770                 775                 780
Asp Lys Leu Pro Ile Lys Ile Val Lys Lys Asn Asn Leu Phe Val Val
785                 790                 795                 800
Asp Arg Ser Asp Lys Leu Gly Arg Val Gln Glu Phe Asn Ser Gly Leu
                805                 810                 815
Leu His Trp Gln Leu Gly Gly Gly Asp Thr Thr Glu His Ile Gln Thr
                820                 825                 830
His Phe Glu Ser Lys Met Glu Ile Pro Pro Arg Arg Pro Pro Pro
                835                 840                 845
Pro Leu Ser Ser Ala Gly Arg Lys Lys Glu Gln Glu Gly Lys Gly Asp
850                 855                 860
```

Ser Glu Glu Gln Gln Glu Lys Ser Ile Ile Ala Thr Ile Asp Asp Val
865                 870                 875                 880

Leu Ser Ala Arg Pro Gly Ala Leu Pro Glu Asp Ala Asn Pro Gly Pro
            885                 890                 895

Gln Thr Glu Ser Ser Lys Phe Pro Phe Gly Ile Gln Gln Ala Lys Ser
        900                 905                 910

His Arg Asn Ile Lys Leu Leu Glu Asp Glu Pro Arg Ser Arg Asp Glu
            915                 920                 925

Thr Pro Leu Cys Thr Ile Ala His Trp Gln Asp Ser Leu Ala Lys Arg
        930                 935                 940

Cys Ile Cys Val Ser Asn Ile Val Arg Ser Leu Ser Phe Val Pro Gly
945                 950                 955                 960

Asn Asp Ala Glu Met Ser Lys His Pro Gly Leu Val Leu Ile Leu Gly
                965                 970                 975

Lys Leu Ile Leu Leu His His Glu His Pro Glu Arg Lys Arg Ala Pro
            980                 985                 990

Gln Thr Tyr Glu Lys Glu Glu Asp Glu Asp Lys Gly Val Ala Cys Ser
        995                 1000                1005

Lys Asp Glu Trp Trp Asp Cys Leu Glu Val Leu Arg Asp Asn Thr
    1010                1015                1020

Leu Val Thr Leu Ala Asn Ile Ser Gly Gln Leu Asp Leu Ser Ala Tyr
1025                1030                1035                1040

Thr Glu Ser Ile Cys Leu Pro Ile Leu Asp Gly Leu Leu His Trp Met
                1045                1050                1055

Val Cys Pro Ser Ala Glu Ala Gln Asp Pro Phe Pro Thr Val Gly Pro
            1060                1065                1070

Asn Ser Val Leu Ser Pro Gln Arg Leu Val Leu Glu Thr Leu Cys Lys
            1075                1080                1085

Leu Ser Ile Gln Asp Asn Asn Val Asp Leu Ile Leu Ala Thr Pro Pro
        1090                1095                1100

Phe Ser Arg Gln Glu Lys Phe Tyr Ala Thr Leu Val Arg Tyr Val Gly
1105                1110                1115                1120

Asp Arg Lys Asn Pro Val Cys Arg Glu Met Ser Met Ala Leu Leu Ser
            1125                1130                1135

Asn Leu Ala Gln Gly Asp Ala Leu Ala Ala Arg Ala Ile Ala Val Gln
            1140                1145                1150

Lys Gly Ser Ile Gly Asn Leu Ile Ser Phe Leu Glu Asp Gly Val Thr
        1155                1160                1165

Met Ala Gln Tyr Gln Gln Ser Gln His Asn Leu Met His Met Gln Pro
    1170                1175                1180

Pro Pro Leu Glu Pro Pro Ser Val Asp Met Met Cys Arg Ala Ala Lys
1185                1190                1195                1200

Ala Leu Leu Ala Met Ala Arg Val Asp Glu Asn Arg Ser Glu Phe Leu
                1205                1210                1215

Leu His Glu Gly Arg Leu Leu Asp Ile Ser Ile Ser Ala Val Leu Asn
            1220                1225                1230

Ser Leu Val Ala Ser Val Ile Cys Asp Val Leu Phe Gln Ile Gly Gln
        1235                1240                1245

Leu

<210> SEQ ID NO 34
<211> LENGTH: 2887
<212> TYPE: DNA
<213> ORGANISM: Homo Sapien

<400> SEQUENCE: 34

```
taactgagcg aggagcaatt gattaatagc tcggcgaggg gactcactga ctgttataat      60
aacactacac cagcaactcc tggcttccca gcagccggaa cacagacagg agagagtcag     120
tggcaaatag acattttcct tatttcttaa aaaacagcaa cttgtttgct acttttattt     180
ctgttgattt ttttttcttg gtgtgtgtgg tggttgtttt taagtgtgga gggcaaaagg     240
agataccatc ccaggctcag tccaaccccct ctccaaaacg gcttttctga cactccaggt    300
agcgagggag ttgggtctcc aggttgtgcg aggagcaaat gatgaccgcc aaggccgtag     360
acaaaatccc agtaactctc agtggttttg tgcaccagct gtctgacaac atctacccgg     420
tggaggacct cgccgccacg tcggtgacca tctttcccaa tgccgaactg ggaggcccct     480
ttgaccagat gaacggagtg gccggagatg gcatgatcaa cattgacatg actggagaga     540
agaggtcgtt ggatctccca tatcccagca gctttgctcc cgtctctgca cctagaaaacc    600
agaccttcac ttacatgggc aagttctcca ttgaccctca gtaccctggt gccagctgct     660
acccagaagg cataatcaat attgtgagtg caggcatctt gcaagggtc acttccccag      720
cttcaaccac agcctcatcc agcgtcacct ctgcctcccc caacccactg ccacaggac      780
ccctgggtgt gtgcaccatg tcccagaccc agcctgacct ggaccacctg tactctccgc     840
caccgcctcc tcctccttat tctggctgtg caggagacct ctaccaggac ccttctgcgt     900
tcctgtcagc agccaccacc tccacctctt cctctctggc ctaccaccca cctccttcct     960
atccatcccc caagccagcc acggacccag gtctcttccc aatgatccca gactatcctg    1020
gattctttcc atctcagtgc cagagagacc tacatggtac agctggccca gaccgtaagc    1080
cctttccctg cccactggac accctgcggg tgcccctcc actcactcca ctctctacaa     1140
tccgtaactt taccctgggg ggccccagtg ctggggtgac cggaccaggg gccagtggag    1200
gcagcgaggg accccggctg cctggtagca gctcagcagc agcagcagcc gccgccgccg    1260
ccgcctataa cccacaccac ctgccactgc ggcccattct gaggcctcgc aagtacccca    1320
acagacccag caagacgccg gtgcacgaga ggccctaccc gtgcccagca gaaggctgcg    1380
accggcggtt ctcccgctct gacgagctga cacggcacat ccgaatccac actgggcata    1440
agccttcca gtgtcggatc tgcatgcgca acttcagccg cagtgaccac ctcaccaccc     1500
atatccgcac ccacaccggt gagaagccct tcgcctgtga ctactgtggc cgaaagtttg    1560
cccggagtga tgagaggaag cgccacacca agatccacct gagacagaaa gagcggaaaa    1620
gcagtgcccc ctctgcatcg gtgccagccc cctctacagc ctcctgctct ggggcgtgc    1680
agcctggggg tacccctgtg caccagtaaca gcagcagtct tggcggaggg ccgctcgccc    1740
cttgctcctc tcggacccgg acaccttgag atgagactca ggctgataca ccagctccca    1800
aagtccccgg aggcccttg tccactggag ctgcacaaca aacactacca cccttttcctg    1860
tccctctctc ccttttgttgg gcaaagggct ttggtggagc tagcactgcc cccttttccac   1920
ctagaagcag gttcttccta aaacttagcc cattctagtc tctcttaggt gagttgacta    1980
tcaacccaag gcaaagggga ggctcagaag gaggtggtgt ggggaccct ggccaagagg     2040
gctgaggtct gaccctgctt taaagggttg tttgactagg ttttgctacc ccacttcccc    2100
ttattttgac ccatcacagg tttttgaccc tggatgtcag agttgatcta agacgttttc    2160
tacaataggt tgggagatgc tgatcccttc aagtggggac agcaaaaaga caagcaaaac    2220
tgatgtgcac tttatggctt gggactgatt tgggggacat tgtacagtga gtgaagtata    2280
```

-continued

```
gcctttatgc cacactctgt ggccctaaaa tggtgaatca gagcatatct agttgtctca    2340
acccttgaag caatatgtat tataaactca gagaacagaa gtgcaatgtg atgggaggaa    2400
catagcaata tctgctcctt ttcgagttgt ttgagaaatg taggctattt tttcagtgta    2460
tatccactca gattttgtgt attttttgatg tacactgttc tctaaattct gaatctttgg    2520
gaaaaaatgt aaagcattta tgatctcaga ggttaactta tttaaggggg atgtacatat    2580
attctctgaa actaggatgc atgcaattgt gttggaagtg tccttggtgc cttgtgtgat    2640
gtagacaatg ttacaaggtc tgcatgtaaa tgggttgcct tattatggag aaaaaaatca    2700
ctccctgagt ttagtatggc tgtatatttc tgcctattaa tatttggaat ttttttttaga    2760 aagtatattt ttgtatgctt tgttttgtga cttaaaagtg ttacctttgt agtcaaattt    2820
cagataagaa tgtacataat gttaccggag ctgatttgtt tggtcattag ctcttaatag    2880
ttgtgaa                                                              2887
```

<210> SEQ ID NO 35
<211> LENGTH: 488
<212> TYPE: PRT
<213> ORGANISM: Homo Sapien

<400> SEQUENCE: 35

```
Arg Gly Ser Trp Val Ser Arg Leu Cys Glu Glu Gln Met Met Thr Ala
1               5                   10                  15

Lys Ala Val Asp Lys Ile Pro Val Thr Leu Ser Gly Phe Val His Gln
            20                  25                  30

Leu Ser Asp Asn Ile Tyr Pro Val Glu Asp Leu Ala Ala Thr Ser Val
        35                  40                  45

Thr Ile Phe Pro Asn Ala Glu Leu Gly Gly Pro Phe Asp Gln Met Asn
    50                  55                  60

Gly Val Ala Gly Asp Gly Met Ile Asn Ile Asp Met Thr Gly Glu Lys
65                  70                  75                  80

Arg Ser Leu Asp Leu Pro Tyr Pro Ser Ser Phe Ala Pro Val Ser Ala
                85                  90                  95

Pro Arg Asn Gln Thr Phe Thr Tyr Met Gly Lys Phe Ser Ile Asp Pro
            100                 105                 110

Gln Tyr Pro Gly Ala Ser Cys Tyr Pro Glu Gly Ile Ile Asn Ile Val
        115                 120                 125

Ser Ala Gly Ile Leu Gln Gly Val Thr Ser Pro Ala Ser Thr Thr Ala
    130                 135                 140

Ser Ser Ser Val Thr Ser Ala Ser Pro Asn Pro Leu Ala Thr Gly Pro
145                 150                 155                 160

Leu Gly Val Cys Thr Met Ser Gln Thr Gln Pro Asp Leu Asp His Leu
                165                 170                 175

Tyr Ser Pro Pro Pro Pro Pro Pro Tyr Ser Gly Cys Ala Gly Asp
            180                 185                 190

Leu Tyr Gln Asp Pro Ser Ala Phe Leu Ser Ala Thr Thr Ser Thr
        195                 200                 205

Ser Ser Ser Leu Ala Tyr Pro Pro Pro Ser Tyr Pro Ser Pro Lys
    210                 215                 220

Pro Ala Thr Asp Pro Gly Leu Phe Pro Met Ile Pro Asp Tyr Pro Gly
225                 230                 235                 240

Phe Phe Pro Ser Gln Cys Gln Arg Asp Leu His Gly Thr Ala Gly Pro
                245                 250                 255

Asp Arg Lys Pro Phe Pro Cys Pro Leu Asp Thr Leu Arg Val Pro Pro
```

```
                    260              265              270
Pro Leu Thr Pro Leu Ser Thr Ile Arg Asn Phe Thr Leu Gly Gly Pro
            275              280              285
Ser Ala Gly Val Thr Gly Pro Gly Ala Ser Gly Gly Ser Glu Gly Pro
        290              295              300
Arg Leu Pro Gly Ser Ser Ala Ala Ala Ala Ala Ala Ala Ala Ala Ala
305              310              315              320
Ala Tyr Asn Pro His His Leu Pro Leu Arg Pro Ile Leu Arg Pro Arg
                325              330              335
Lys Tyr Pro Asn Arg Pro Ser Lys Thr Pro Val His Glu Arg Pro Tyr
            340              345              350
Pro Cys Pro Ala Glu Gly Cys Asp Arg Arg Phe Ser Arg Ser Asp Glu
            355              360              365
Leu Thr Arg His Ile Arg Ile His Thr Gly His Lys Pro Phe Gln Cys
        370              375              380
Arg Ile Cys Met Arg Asn Phe Ser Arg Ser Asp His Leu Thr Thr His
385              390              395              400
Ile Arg Thr His Thr Gly Glu Lys Pro Phe Ala Cys Asp Tyr Cys Gly
            405              410              415
Arg Lys Phe Ala Arg Ser Asp Glu Arg Lys Arg His Thr Lys Ile His
            420              425              430
Leu Arg Gln Lys Glu Arg Lys Ser Ala Pro Ser Ala Ser Val Pro
        435              440              445
Ala Pro Ser Thr Ala Ser Cys Ser Gly Gly Val Gln Pro Gly Gly Thr
        450              455              460
Leu Cys Ser Ser Asn Ser Ser Ser Leu Gly Gly Gly Pro Leu Ala Pro
465              470              475              480
Cys Ser Ser Arg Thr Arg Thr Pro
                485

<210> SEQ ID NO 36
<211> LENGTH: 300
<212> TYPE: DNA
<213> ORGANISM: Homo Sapien

<400> SEQUENCE: 36
attaagatgt tctacgagga gcatttgcac ttggacgatg agatccgcta catcctggat      60
ggcagtgggt acttcgatgt gagggacaag gaggaccagt ggatccggat cttcatggag     120
aagggagaca tggtgacgct ccccgcgggg atctatcacc gcttcacggt ggacgagaag     180
aactacacga aggccatgcg gctgtttgtg ggagaaccgg tgtggacagc gtacaaccgg     240
cccgctgacc attttgaagc ccgcgggcag tacgtgaaat tctggcaca gaccgcctag      300

<210> SEQ ID NO 37
<211> LENGTH: 99
<212> TYPE: PRT
<213> ORGANISM: Homo Sapien

<400> SEQUENCE: 37

Ile Lys Met Phe Tyr Glu Glu His Leu His Leu Asp Asp Glu Ile Arg
1               5                   10                  15
Tyr Ile Leu Asp Gly Ser Gly Tyr Phe Asp Val Arg Asp Lys Glu Asp
            20                  25                  30
Gln Trp Ile Arg Ile Phe Met Glu Lys Gly Asp Met Val Thr Leu Pro
        35                  40                  45
```

```
Ala Gly Ile Tyr His Arg Phe Thr Val Asp Glu Lys Asn Tyr Thr Lys
 50                  55                  60

Ala Met Arg Leu Phe Val Gly Glu Pro Val Trp Thr Ala Tyr Asn Arg
 65                  70                  75                  80

Pro Ala Asp His Phe Glu Ala Arg Gly Gln Tyr Val Lys Phe Leu Ala
                 85                  90                  95

Gln Thr Ala

<210> SEQ ID NO 38
<211> LENGTH: 2404
<212> TYPE: DNA
<213> ORGANISM: Homo Sapien

<400> SEQUENCE: 38
```

| | | | | |
|---|---|---|---|---|
| gaaaaggtgg acaagtccta ttttcaagag aagatgactt ttaacagttt tgaaggatct | 60 |
| aaaacttgtg tacctgcaga catcaataag gaagaagaat ttgtagaaga gtttaataga | 120 |
| ttaaaaactt ttgctaattt tccaagtggt agtcctgttt cagcatcaac actggcacga | 180 |
| gcagggtttc tttatactgg tgaaggagat accgtgcggt gctttagttg tcatgcagct | 240 |
| gtagatagat ggcaatatgg agactcagca gttggaagac acaggaaagt atccccaaat | 300 |
| tgcagattta tcaacggctt ttatcttgaa aatagtgcca cgcagtctac aaattctggt | 360 |
| atccagaatg gtcagtacaa agttgaaaac tatctgggaa gcagagatca ttttgcctta | 420 |
| gacaggccat ctgagacaca tgcagactat cttttgagaa ctgggcaggt tgtagatata | 480 |
| tcagacacca tatcccgag gaaccctgcc atgtatagtg aagaagctag attaaagtcc | 540 |
| tttcagaact ggccagacta tgctcaccta accccaagag agttagcaag tgctggactc | 600 |
| tactacacag gtattggtga ccaagtgcag tgcttttgtt gtggtggaaa actgaaaaat | 660 |
| tgggaacctt gtgatcgtgc ctggtcagta acacaggcga cactttccta attgcttctt | 720 |
| tgttttgggc cggaatctta atattcgaag tgaatctgat gctgtgagtt ctgataggaa | 780 |
| tttcccaaat tcaacaaatc ttccaagaaa tccatccatg gcagattatg aagcacggat | 840 |
| cttactttt gggacatgga tatactcagt taacaaggag cagcttgcaa gagctggatt | 900 |
| ttatgcttta ggtgaaggtg ataaagtaaa gtgctttcac tgtggaggag gctaactga | 960 |
| ttggaagccc agtgaagacc cttgggaaca acatgctaaa tggtatccag ggtgcaaata | 1020 |
| tctgttagaa cagaagggac aagaatatat aaacaatatt catttaactc attcacttga | 1080 |
| ggagtgtctg gtaagaacta ctgagaaaac accatcacta actagaagaa ttgatgatac | 1140 |
| catcttccaa atcctatgg tacaagaagc tatacgaatg gggttcagtt tcaaggacat | 1200 |
| taagaaaata atggaggaaa aaattcagat atctgggagc aactataaat cacttggagt | 1260 |
| tctggttgca gatctagtga atgctcagaa agacagtatg caagatgagt caagtcagac | 1320 |
| ttcattacag aaagagatta gtactgaaga gcagctaagg cgcctgcaag aggagaagct | 1380 |
| ttgcaaaatc tgtatggata gaaatattgc tatcgttttt gttccttgtg acatctagt | 1440 |
| cacttgtaaa caatgtgctg aagcagttga caagtgtccc atgtgctaca cagtcattac | 1500 |
| tttcaagcaa aaaattttta tgtcttaatc taactctata gtaggcatgt tatgttgttc | 1560 |
| ttattaccct gattgaatgt gtgatgtgaa ctgactttaa gtaatcagga ttgaattcca | 1620 |
| ttagcatttg ctaccaagta ggaaaaaaaa tgtacatggc agtgtttag ttggcaatat | 1680 |
| aatctttgaa tttcttgatt tttcaggta ttagctgtat tatccatttt ttttactggt | 1740 |
| atttaattga aaccatagac taagaataag aagcatcata ctataactga acacaatgtg | 1800 |

-continued

```
tattcatagt atactgattt aatttctaag tgtaagtgaa ttaatcatct ggattttta      1860 ttctttcag ataggcttaa caaatggagc tttctgtata taaatgtgga gattagagtt      1920
aatctcccca atcacataat ttgttttgtg tgaaaaggaa taaattgttc catgctggtg      1980
gaaagataga gattgttttt agaggttggt tgttgtgttt taggattctg tccatttct       2040 tttaaagtta taaacacgta cttgtgcgaa ttattttttt aaagtgattt gccatttttg      2100
aaagcgtatt taatgataga atactatcga gccaacatgt actgacatgg aaagatgtca     2160
aagatatgtt aagtgtaaaa tgcaagtggc aaaacactat gtatagtctg agccagatca     2220
aagtatgtat gttttaata tgcatagaac aaaagatttg gaaagatata caccaaactg      2280
ttaaatgtgg tttctcttcg gggagggggg gattgggggg aggggcccca gagggttttt    2340
ataggggcct tttcactttc tacttttttc attttgttct gttcgaattt tttataagta     2400
tgta                                                                  2404
```

<210> SEQ ID NO 39
211> LENGTH: 278
<212> TYPE: PRT
<213> ORGANISM: Homo Sapien

<400> SEQUENCE: 39

```
His Arg Arg His Phe Pro Asn Cys Phe Phe Val Leu Gly Arg Asn Leu
1               5                   10                  15

Asn Ile Arg Ser Glu Ser Asp Ala Val Ser Ser Asp Arg Asn Phe Pro
            20                  25                  30

Asn Ser Thr Asn Leu Pro Arg Asn Pro Ser Met Ala Asp Tyr Glu Ala
        35                  40                  45

Arg Ile Phe Thr Phe Gly Thr Trp Ile Tyr Ser Val Asn Lys Glu Gln
    50                  55                  60

Leu Ala Arg Ala Gly Phe Tyr Ala Leu Gly Glu Gly Asp Lys Val Lys
65                  70                  75                  80

Cys Phe His Cys Gly Gly Gly Leu Thr Asp Trp Lys Pro Ser Glu Asp
                85                  90                  95

Pro Trp Glu Gln His Ala Lys Trp Tyr Pro Gly Cys Lys Tyr Leu Leu
            100                 105                 110

Glu Gln Lys Gly Gln Glu Tyr Ile Asn Asn Ile His Leu Thr His Ser
        115                 120                 125

Leu Glu Glu Cys Leu Val Arg Thr Thr Glu Lys Thr Pro Ser Leu Thr
    130                 135                 140

Arg Arg Ile Asp Asp Thr Ile Phe Gln Asn Pro Met Val Gln Glu Ala
145                 150                 155                 160

Ile Arg Met Gly Phe Ser Phe Lys Asp Ile Lys Lys Ile Met Glu Glu
                165                 170                 175

Lys Ile Gln Ile Ser Gly Ser Asn Tyr Lys Ser Leu Glu Val Leu Val
            180                 185                 190

Ala Asp Leu Val Asn Ala Gln Lys Asp Ser Met Gln Asp Glu Ser Ser
        195                 200                 205

Gln Thr Ser Leu Gln Lys Glu Ile Ser Thr Glu Glu Gln Leu Arg Arg
    210                 215                 220

Leu Gln Glu Glu Lys Leu Cys Lys Ile Cys Met Asp Arg Asn Ile Ala
225                 230                 235                 240

Ile Val Phe Val Pro Cys Gly His Leu Val Thr Cys Lys Gln Cys Ala
                245                 250                 255

Glu Ala Val Asp Lys Cys Pro Met Cys Tyr Thr Val Ile Thr Phe Lys
            260                 265                 270
```

-continued

Gln Lys Ile Phe Met Ser
    275

<210> SEQ ID NO 40
<211> LENGTH: 2409
<212> TYPE: DNA
<213> ORGANISM: Homo Sapien

<400> SEQUENCE: 40

| atgtcgggtc gccgctgcgc cggcggggga gcggcctgcg cgagcgccgc ggccgaggcc | 60 |
| gtggagccgg ccgcccgaga gctgttcgag gcgtgccgca acggggacgt ggaacgagtc | 120 |
| aagaggctgg tgacgcctga aaggtgaac agccgcgaca cggcgggcag gaaatccacc | 180 |
| ccgctgcact tcgccgcagg ttttgggcgg aaagacgtag ttgaatattt gcttcagaat | 240 |
| ggtgcaaatg tccaagcacg tgatgatggg ggccttattc ctcttcataa tgcatgctct | 300 |
| tttggtcatg ctgaagtagt caatctcctt ttgcgacatg gtgcagaccc caatgctcga | 360 |
| gataattgga attatactcc tctccatgaa gctgcaatta aggaaagat tgatgtttgc | 420 |
| attgtgctgt tacagcatgg agctgagcca accatccgaa atacagatgg aaggacagca | 480 |
| ttggatttag cagatccatc tgccaaagca gtgcttactg gtaagtctgt atactctggt | 540 |
| tattccagga agcctgtaaa gaacaacctt gccaggagtg gcaatgaaga aaaaatgatg | 600 |
| gctctactca caccattaaa tgtcaactgc cacgcaagtg atggcagaaa gcatggtgcc | 660 |
| tgtgtaaatg caatggactt gtggcaattc actcctcttc atgaggcagc ttctaagaac | 720 |
| agggttgaag tatgttctct tctcttaagt tatggtgcag acccaacact gctcaattgt | 780 |
| cacaataaaa gtgctataga cttggctccc acaccacagt taaagaaaag attagcatat | 840 |
| gaatttaaag gccactcgtt gctgcaagct gcacgagaag ctgatgttac tcgaatcaaa | 900 |
| aaacatctct ctctggaaat ggtgaatttc aagcatcctc aaacacatga acagcattg | 960 |
| aaactgtgta ctgttcagag tgtcaactgc agagacattg aagggcgtca gtctacacca | 1020 |
| cttcattttg cagctgggta taacagagtg tccgtggtgg aatatctgct acagcatgga | 1080 |
| gctgatgtgc atgctaaaga taaggaggc cttgtacctt gcacaatgc atgttcttat | 1140 |
| ggacattatg aagttgcaga acttcttgtt aaacatggag cagtagttaa tgtagctgat | 1200 |
| ttatggaaat ttacaccttt acatgaagca gcagcaaag gaaaatatga aatttgcaaa | 1260 |
| cttctgctcc agcatggtgc agaccctaca aaaaaaaaca gggatggaaa tactcctttg | 1320 |
| gatcttgtta aagatggaga tacagatatt caagatctgc ttaggggaga tgcagctttg | 1380 |
| ctagatgctg ccaagaaggg ttgtttagcc agagtgaaga agttgtcttc tcctgataat | 1440 |
| gtaaattgcc gcgatacccca aggcagacat tcaacacctt tacatttagc agctggttat | 1500 |
| aataatttag aagttgcaga gtatttgtta caacacggag ctgatgtgaa tgcccaagac | 1560 |
| aaaggaggac ttattccttt acataatgca gcatcttacg ggatcacttt ggatgtatta | 1620 |
| gttgagatgg ggcacaagga gctgaaggag attggaatca atgcttatgg acataggcac | 1680 |
| aaactaatta aaggagtcga gacttatc tccggacaac aaggtcttaa cccatattta | 1740 |
| actttgaaca cctctggtag tggaacaatt cttatagatc tgtctcctga tgataaagag | 1800 |
| tttcagtctg tggaggaaga gatgcaaagt acagttcgag agcacagaga tggaggtcat | 1860 |
| gcaggtggaa tcttcaacag atacaatatt ctcaagattc agaaggtttg taacaagaaa | 1920 |
| ctatgggaaa gatacactca ccggagaaaa gaagtttctg aagaaaacca caaccatgcc | 1980 |
| aatgaacgaa tgctatttca tgggtctcct tttgtgaatg caattatcca caaggctttt | 2040 |

-continued

```
gatgaaaggc atgcgtacat aggtggtatg tttggagctg gcatttattt tgctgaaaac    2100
tcttccaaaa gcaatcaata tgtatatgga attggaggag gtactgggtg tccagttcac    2160
aaagacagat cttgttacat tgccacagg cagctgctct tttgccgggt aaccttggga    2220
aagtctttcc tgcagttcag tgcaatgaaa atggcacatt ctcctccagg tcatcactca    2280
gtcactggta ggcccagtgt aaatggccta gcattagctg aatatgttat ttacagagga    2340
gaacaggctt atcctgagta tttaattact taccagatta tgaggcctga aggtatggtc    2400
gatggataa                                                             2409
```

<210> SEQ ID NO 41
<211> LENGTH: 802
<212> TYPE: PRT
<213> ORGANISM: Homo Sapien

<400> SEQUENCE: 41

```
Met Ser Gly Arg Arg Cys Ala Gly Gly Ala Ala Cys Ala Ser Ala
1               5                   10                  15

Ala Ala Glu Ala Val Glu Pro Ala Ala Arg Glu Leu Phe Glu Ala Cys
            20                  25                  30

Arg Asn Gly Asp Val Glu Arg Val Lys Arg Leu Val Thr Pro Glu Lys
        35                  40                  45

Val Asn Ser Arg Asp Thr Ala Gly Arg Lys Ser Thr Pro Leu His Phe
    50                  55                  60

Ala Ala Gly Phe Gly Arg Lys Asp Val Val Glu Tyr Leu Leu Gln Asn
65                  70                  75                  80

Gly Ala Asn Val Gln Ala Arg Asp Asp Gly Gly Leu Ile Pro Leu His
                85                  90                  95

Asn Ala Cys Ser Phe Gly His Ala Glu Val Val Asn Leu Leu Leu Arg
            100                 105                 110

His Gly Ala Asp Pro Asn Ala Arg Asp Asn Trp Asn Tyr Thr Pro Leu
        115                 120                 125

His Glu Ala Ala Ile Lys Gly Lys Ile Asp Val Cys Ile Val Leu Leu
    130                 135                 140

Gln His Gly Ala Glu Pro Thr Ile Arg Asn Thr Asp Gly Arg Thr Ala
145                 150                 155                 160

Leu Asp Leu Ala Asp Pro Ser Ala Lys Ala Val Leu Thr Gly Lys Ser
                165                 170                 175

Val Tyr Ser Gly Tyr Ser Arg Lys Pro Val Lys Asn Asn Leu Ala Arg
            180                 185                 190

Ser Gly Asn Glu Glu Lys Met Met Ala Leu Leu Thr Pro Leu Asn Val
        195                 200                 205

Asn Cys His Ala Ser Asp Gly Arg Lys His Gly Ala Cys Val Asn Ala
    210                 215                 220

Met Asp Leu Trp Gln Phe Thr Pro Leu His Glu Ala Ala Ser Lys Asn
225                 230                 235                 240

Arg Val Glu Val Cys Ser Leu Leu Leu Ser Tyr Gly Ala Asp Pro Thr
                245                 250                 255

Leu Leu Asn Cys His Asn Lys Ser Ala Ile Asp Leu Ala Pro Thr Pro
            260                 265                 270

Gln Leu Lys Glu Arg Leu Ala Tyr Glu Phe Lys Gly His Ser Leu Leu
        275                 280                 285

Gln Ala Ala Arg Glu Ala Asp Val Thr Arg Ile Lys Lys His Leu Ser
    290                 295                 300
```

-continued

```
Leu Glu Met Val Asn Phe Lys His Pro Gln Thr His Glu Thr Ala Leu
305                 310                 315                 320

Lys Leu Cys Thr Val Gln Ser Val Asn Cys Arg Asp Ile Glu Gly Arg
            325                 330                 335

Gln Ser Thr Pro Leu His Phe Ala Ala Gly Tyr Asn Arg Val Ser Val
            340                 345                 350

Val Glu Tyr Leu Leu Gln His Gly Ala Asp Val His Ala Lys Asp Lys
        355                 360                 365

Gly Gly Leu Val Pro Leu His Asn Ala Cys Ser Tyr Gly His Tyr Glu
    370                 375                 380

Val Ala Glu Leu Leu Val Lys His Gly Ala Val Val Asn Val Ala Asp
385                 390                 395                 400

Leu Trp Lys Phe Thr Pro Leu His Glu Ala Ala Lys Gly Lys Tyr
                405                 410                 415

Glu Ile Cys Lys Leu Leu Leu Gln His Gly Ala Asp Pro Thr Lys Lys
            420                 425                 430

Asn Arg Asp Gly Asn Thr Pro Leu Asp Leu Val Lys Asp Gly Asp Thr
        435                 440                 445

Asp Ile Gln Asp Leu Leu Arg Gly Asp Ala Ala Leu Leu Asp Ala Ala
    450                 455                 460

Lys Lys Gly Cys Leu Ala Arg Val Lys Lys Leu Ser Ser Pro Asp Asn
465                 470                 475                 480

Val Asn Cys Arg Asp Thr Gln Gly Arg His Ser Thr Pro Leu His Leu
            485                 490                 495

Ala Ala Gly Tyr Asn Asn Leu Glu Val Ala Glu Tyr Leu Leu Gln His
            500                 505                 510

Gly Ala Asp Val Asn Ala Gln Asp Lys Gly Gly Leu Ile Pro Leu His
        515                 520                 525

Asn Ala Ala Ser Tyr Gly Ile Thr Leu Asp Val Leu Val Glu Met Gly
    530                 535                 540

His Lys Glu Leu Lys Glu Ile Gly Ile Asn Ala Tyr Gly His Arg His
545                 550                 555                 560

Lys Leu Ile Lys Gly Val Glu Arg Leu Ile Ser Gly Gln Gln Gly Leu
            565                 570                 575

Asn Pro Tyr Leu Thr Leu Asn Thr Ser Gly Ser Gly Thr Ile Leu Ile
            580                 585                 590

Asp Leu Ser Pro Asp Asp Lys Glu Phe Gln Ser Val Glu Glu Glu Met
        595                 600                 605

Gln Ser Thr Val Arg Glu His Arg Asp Gly His Ala Gly Gly Ile
    610                 615                 620

Phe Asn Arg Tyr Asn Ile Leu Lys Ile Gln Lys Val Cys Asn Lys Lys
625                 630                 635                 640

Leu Trp Glu Arg Tyr Thr His Arg Arg Lys Glu Val Ser Glu Glu Asn
                645                 650                 655

His Asn His Ala Asn Glu Arg Met Leu Phe His Gly Ser Pro Phe Val
            660                 665                 670

Asn Ala Ile Ile His Lys Gly Phe Asp Glu Arg His Ala Tyr Ile Gly
        675                 680                 685

Gly Met Phe Gly Ala Gly Ile Tyr Phe Ala Glu Asn Ser Ser Lys Ser
    690                 695                 700

Asn Gln Tyr Val Tyr Gly Ile Gly Gly Gly Thr Gly Cys Pro Val His
705                 710                 715                 720
```

-continued

```
Lys Asp Arg Ser Cys Tyr Ile Cys His Arg Gln Leu Leu Phe Cys Arg
            725                 730                 735
Val Thr Leu Gly Lys Ser Phe Leu Gln Phe Ser Ala Met Lys Met Ala
        740                 745                 750
His Ser Pro Pro Gly His His Ser Val Thr Gly Arg Pro Ser Val Asn
    755                 760                 765
Gly Leu Ala Leu Ala Glu Tyr Val Ile Tyr Arg Gly Glu Gln Ala Tyr
770                 775                 780
Pro Glu Tyr Leu Ile Thr Tyr Gln Ile Met Arg Pro Glu Gly Met Val
785                 790                 795                 800
Asp Gly
```

<210> SEQ ID NO 42
<211> LENGTH: 5175
<212> TYPE: DNA
<213> ORGANISM: Homo Sapien

<400> SEQUENCE: 42

| | | | | | |
|---|---|---|---|---|---|
| tctgatgcca | atgcaagtta | cttaagagca | gctcgagctg | gacaccttga | aaaggccctc | 60 |
| gactacataa | aaaatggagt | tgacatcaac | atttgcaatc | agaatgggtt | gaacgctctc | 120 |
| caccttgctt | ccaaagaagg | ccatgtagag | gttgtttctg | agctgctgca | gagagaagcc | 180 |
| aatgtggatg | cagctacaaa | gaaggaaac | acagcattgc | acatcgcatc | tttggctggg | 240 |
| caagcagagg | tggtaaaagt | cttggttaca | aatggagcca | atgtcaatgc | acaatctcag | 300 |
| aatggttca | cgccattgta | tatggcagcc | aggaaaatc | acctggaagt | tgtcaagttt | 360 |
| cttcttgaca | atggtgcaag | ccagagccta | gccacagagg | atggcttcac | accattggca | 420 |
| gtggctttgc | aacaaggtca | cgaccaagtc | gtttcgctcc | tgctagagaa | tgacaccaaa | 480 |
| ggaaaagtgc | gtctcccagc | tcttcatatc | gcggcccgaa | agacgacac | gaaagccgcc | 540 |
| gccctgctgc | tgcagaatga | caacaatgca | gatgtggaat | caagagtgg | cttcactccg | 600 |
| ctccacatag | ctgctcacta | tggaaatatc | aatgtagcca | cgttgctgtt | aaaccgagcg | 660 |
| gctgctgtgg | atttcaccgc | aaggaatgac | atcactcctt | tacatgttgc | atcaaaaaga | 720 |
| ggaaatgcaa | atatggtaaa | actattgctc | gatcgaggag | ctaaaatcga | tgccaaaacc | 780 |
| agggatggtc | tgacaccact | gcactgtgga | gcaaggagtg | gccacgagca | ggtggtagaa | 840 |
| atgttgcttg | atcgagctgc | ccccattctt | tcaaaaacca | agaatggatt | atctccattg | 900 |
| cacatggcca | cacaagggga | tcatttaaac | tgcgtccagc | ttctcctcca | gcataatgta | 960 |
| cccgtggatg | atgtcaccaa | tgactacctg | actgccctac | acgtggctgc | ccactgtggc | 1020 |
| cattacaaag | ttgccaaggt | tctcttggat | aagaaagcta | accccaatgc | caaagccctg | 1080 |
| aatggctta | cccctcttca | tattgcctgc | aagaagaatc | gaattaaagt | aatggaactc | 1140 |
| cttctgaaac | acggtgcatc | catccaagct | gtaaccgaga | gagagaaac | agcactgcac | 1200 |
| atggcagctc | gctccggcca | agctgaagtt | gtgcggtatc | tggtacaaga | cggagctcag | 1260 |
| gtagaagcta | agctaagga | tgaccaaaca | ccactccaca | tttcagcccg | actggggaaa | 1320 |
| gcagacatag | tacaacagct | gttgcagcaa | ggggcatctc | caatgcagc | cacaacttct | 1380 |
| gggtacaccc | cacttcacct | ttccgcccga | gagggcatg | aggatgtggc | cgcgttcctt | 1440 |
| ttggatcatg | gagcgtcttt | atctataaca | acaaagagcg | ggctaacacc | actgcatgta | 1500 |
| gctgcacatt | acgataatca | gaaagtggcc | cttctgcttt | tggaccaagg | agcctcacct | 1560 |
| cacgcagccg | caaagaatgg | ttatacgcca | ctgcacatcg | ctgccaaaaa | gaaccagatg | 1620 |

-continued

```
gacatagcga caactctgct ggaatatggt gctgatgcca acgcagttac ccggcaagga    1680
attgcttccg tccatctcgc agctcaggaa gggcacgtgg acatggtgtc gctgctcctc    1740
ggtagaaatg cgaatgtgaa cctgagcaat aagagcggcc tgaccccact ccatttggct    1800
gctcaagaag atcgagtgaa tgtggcagaa gtcctcgtaa accaaggggc tcatgtggac    1860
gcccagacaa aggtatacgg ccctcccttg ccacacggaa agaatgtgt ccatttggtg     1920
actgcaaatg ggtatacgcc attacatcaa gcagcacagc aggggcatac gcatataata    1980
aatgtcttac ttcagaacaa cgcctccccc aatgaactca ctgtgactgt cacagagaag    2040
cacaaaatga atgttccaga aacgatgaat gaagttcttg atatgtctga tgatgaagtt    2100
cgtaaagcca atgccctga aatgctcagt gatggcgaat atatctcaga tgttgaagaa     2160
ggtaatagat gcacatggta caaaattccc aaggtacaaa agtttacggt gaaaactgac    2220
actttcaaaa gggaagcttt tgatgtgggc ttactctcta catctgcagg tgaagatgca    2280
atgaccgggg acacagacaa atatcttggg ccacaggacc ttaaggaatt gggtgatgat    2340
tccctgcctg cagagggtta catgggcttt agtctcggag cgcgttctgc caggtttctg    2400
gttagcttta tggtggacgc gagaggggc tccatgagag aagccgtca tcacgggatg      2460
agaatcatca ttcctccacg caagtgtact gccccactc gaatcacctg ccgtttggta     2520
aagagacata aactggccaa cccacccccc atggtggaag agagggatt agccagtagg     2580
ctggtagaaa tgggtcctgc aggggcacaa ttttaggcc ctgtcatagt ggaaatccct     2640
cactttgggt ccatgagagg aaaagagaga gaactcattg ttcttcgaag tgaaaatggt    2700
gaaacttgga aggagcatca gtttgacagc aaaaatgaag atttaaccga gttacttaat    2760
ggcatggatg aagaacttga tagcccagaa gagttaggga aaaagcgtat ctgcaggatt    2820
atcacgaaag atttcccccca gtattttgca gtggttcc ggattaagca ggaaagcaac     2880
cagattggtc ctgaaggtgg aattctgagc agcaccacag tgccccttgt tcaagcatct    2940
ttcccagagg gtgccctaac taaaagaatt cgagtgggcc tccaggccca gcctgttcca    3000
gatgaaattg tgaaaagat ccttggaaac aaagcaactt ttagcccaat tgtcactgtg     3060
gaaccaagaa gacggaaatt ccataaacca atcacaatga ccattccggt gccccgccc    3120
tcaggagaag gtgtatccaa tggatacaaa ggggacacta cacccaatct gcgtcttctc    3180
tgtagcatta caggggcac ttcgcctgct cagtgggaag acatcacagg aacaactcct    3240
ttgacgttta aaaagattg tgtctccttt acaaccaatg tttcagccag gtatggaaat    3300
aaaggattcc aaaaagcagt tctggaagga aaacctattt atgttgattg ttatggaaat    3360
ttggccccac ttaccaaagg aggacagcaa cttgttttta cttttattc tttcaaagaa    3420
aatagactgc cattttccat caagattaga gacaccagcc aagagccctg tggtcgtctg    3480
tcttttctga aagaaccaaa gacaacaaaa ggactgcctc aaacagcggt ttgcaactta    3540
aatatcactc tgccagcaca taaaaagatt gagaaaacag atagacgaca gagcttcgca    3600
tccttagctt tacgtaagcg ctacagctac ttgactgagc ctggaatgaa agaaaaaaag    3660
atgcagtccg agttgtccga tgaggaagaa agtacctcaa gaaacacgtc gttgtccgag    3720
acttcccggg gtggccagcc ttcggttaca acgaagtctg ctagagataa gaaaacagag    3780
gcagcacctt aaaatcaaa gagtgaaaag gccggcagtg agaaaggag cagtagaagg      3840
actgctgatg ccttaacttc ggtcttgaca aaaattaatc gaatagatat agtgacactg    3900
ctagaaggac caatatttga ttatggaaat atttcaggca ccagaagttt tgcagatgag    3960
aacaatgttt tccatgaccc tgttgatggt tatccttccc ttcaagtgga actggaaacc    4020
```

```
cccacagggt tgcactacac accacctacc cctttccagc aagatgatta ttttagtgat    4080
atctctagca tagaatctcc ccttagaacc cctagtagac tgagtgatgg gctagtgcct    4140
tcccagggga acatagagca ttccgcagat ggacctccag tcgtaactgc agaagacgct    4200
tccttagaag acagcaaact ggaagactca gtgcctttaa cagaaatgcc tgaagcagtg    4260
gatgtagatg agagccagtt ggagaatgta tgtctgagtg agtatcctca ataccttgga    4320
aatttggctg ggtccccaaa agatgttaaa ccagcagagc ctagaaaact aggagtaagc    4380
tctgagcagc aggagaaagg aaaatctggt cctgatgagg agatgatgga agagaaactc    4440
aaatctctat ttgaggacat tcaacttgaa gaaggagtag agtctgagga gatgacagaa    4500
gaaaaagtac aggctattct taagcgtgtt cagcaagcag aactggaaat gtcttcaatt    4560
acaggttggc agaatgagac atcaagtgga aacctagagt cctgcgctca agctcgaaga    4620
gtaactggtg ggttactaga tcgactggat gacagccctg accagtgtag agattccatt    4680
acctcatatc tcaaaggaga agctggcaaa tttgaagcaa atggaagcca tacagaaatc    4740
actccagaag caaagacaaa atcttacttt ccagaatccc aaaatgatgt aggaaaacag    4800
agtaccaagg aaactctgaa accaaaaata catggatctg gtcatgttga agaaccagca    4860
tcaccactag cagcatatca gaaatctcta gaagaaacca gcaagcttat aatagaagag    4920
actaaaccct gtgtgcctga cttgaaagac agtgagagtg attcaagctc agaggaagag    4980
cggagagtca ctacccgagt tattcgccgg cgtttgatta taagggaga ggaagcaaaa    5040 aacattcctg gtgaatctgt cacagaagaa caatttactg atgaagaagg caacctcatc    5100
accagaaaag gagaaggttt taaggtgaaa acgaagaaag aaatccggca tgtggaaaag    5160
aagagccact cgtaa                                                    5175
```

<210> SEQ ID NO 43
<211> LENGTH: 1724
<212> TYPE: PRT
<213> ORGANISM: Homo Sapien

<400> SEQUENCE: 43

```
Ser Asp Ala Asn Ala Ser Tyr Leu Arg Ala Arg Ala Gly His Leu
1               5                   10                  15

Glu Lys Ala Leu Asp Tyr Ile Lys Asn Gly Val Asp Ile Asn Ile Cys
            20                  25                  30

Asn Gln Asn Gly Leu Asn Ala Leu His Leu Ala Ser Lys Glu Gly His
        35                  40                  45

Val Glu Val Val Ser Glu Leu Leu Gln Arg Glu Ala Asn Val Asp Ala
    50                  55                  60

Ala Thr Lys Lys Gly Asn Thr Ala Leu His Ile Ala Ser Leu Ala Gly
65                  70                  75                  80

Gln Ala Glu Val Val Lys Val Leu Val Thr Asn Gly Ala Asn Val Asn
                85                  90                  95

Ala Gln Ser Gln Asn Gly Phe Thr Pro Leu Tyr Met Ala Ala Gln Glu
            100                 105                 110

Asn His Leu Glu Val Val Lys Phe Leu Leu Asp Asn Gly Ala Ser Gln
        115                 120                 125

Ser Leu Ala Thr Glu Asp Gly Phe Thr Pro Leu Ala Val Ala Leu Gln
    130                 135                 140

Gln Gly His Asp Gln Val Val Ser Leu Leu Leu Glu Asn Asp Thr Lys
145                 150                 155                 160
```

-continued

```
Gly Lys Val Arg Leu Pro Ala Leu His Ile Ala Ala Arg Lys Asp Asp
                165                 170                 175

Thr Lys Ala Ala Ala Leu Leu Gln Asn Asp Asn Ala Asp Val
                180                 185                 190

Glu Ser Lys Ser Gly Phe Thr Pro Leu His Ile Ala Ala His Tyr Gly
                195                 200                 205

Asn Ile Asn Val Ala Thr Leu Leu Asn Arg Ala Ala Val Asp
210                             215                 220

Phe Thr Ala Arg Asn Asp Ile Thr Pro Leu His Val Ala Ser Lys Arg
225                 230                 235                 240

Gly Asn Ala Asn Met Val Lys Leu Leu Leu Asp Arg Gly Ala Lys Ile
                245                 250                 255

Asp Ala Lys Thr Arg Asp Gly Leu Thr Pro Leu His Cys Gly Ala Arg
                260                 265                 270

Ser Gly His Glu Gln Val Val Glu Met Leu Leu Asp Arg Ala Ala Pro
                275                 280                 285

Ile Leu Ser Lys Thr Lys Asn Gly Leu Ser Pro Leu His Met Ala Thr
                290                 295                 300

Gln Gly Asp His Leu Asn Cys Val Gln Leu Leu Leu Gln His Asn Val
305                 310                 315                 320

Pro Val Asp Asp Val Thr Asn Asp Tyr Leu Thr Ala Leu His Val Ala
                325                 330                 335

Ala His Cys Gly His Tyr Lys Val Ala Lys Val Leu Leu Asp Lys Lys
                340                 345                 350

Ala Asn Pro Asn Ala Lys Ala Leu Asn Gly Phe Thr Pro Leu His Ile
                355                 360                 365

Ala Cys Lys Lys Asn Arg Ile Lys Val Met Glu Leu Leu Leu Lys His
                370                 375                 380

Gly Ala Ser Ile Gln Ala Val Thr Glu Arg Gly Glu Thr Ala Leu His
385                 390                 395                 400

Met Ala Ala Arg Ser Gly Gln Ala Glu Val Val Arg Tyr Leu Val Gln
                405                 410                 415

Asp Gly Ala Gln Val Glu Ala Lys Ala Lys Asp Asp Gln Thr Pro Leu
                420                 425                 430

His Ile Ser Ala Arg Leu Gly Lys Ala Asp Ile Val Gln Gln Leu Leu
                435                 440                 445

Gln Gln Gly Ala Ser Pro Asn Ala Ala Thr Thr Ser Gly Tyr Thr Pro
450                 455                 460

Leu His Leu Ser Ala Arg Glu Gly His Glu Asp Val Ala Ala Phe Leu
465                 470                 475                 480

Leu Asp His Gly Ala Ser Leu Ser Ile Thr Thr Lys Ser Gly Leu Thr
                485                 490                 495

Pro Leu His Val Ala His Tyr Asp Asn Gln Lys Val Ala Leu Leu
                500                 505                 510

Leu Leu Asp Gln Gly Ala Ser Pro His Ala Ala Lys Asn Gly Tyr
                515                 520                 525

Thr Pro Leu His Ile Ala Lys Lys Asn Gln Met Asp Ile Ala Thr
                530                 535                 540

Thr Leu Leu Glu Tyr Gly Ala Asp Ala Asn Ala Val Thr Arg Gln Gly
545                 550                 555                 560

Ile Ala Ser Val His Leu Ala Ala Gln Glu Gly His Val Asp Met Val
                565                 570                 575

Ser Leu Leu Leu Gly Arg Asn Ala Asn Val Asn Leu Ser Asn Lys Ser
```

-continued

```
                580                 585                 590
Gly Leu Thr Pro Leu His Leu Ala Ala Gln Glu Asp Arg Val Asn Val
            595                 600                 605
Ala Glu Val Leu Val Asn Gln Gly Ala His Val Asp Ala Gln Thr Lys
            610                 615                 620
Val Tyr Gly Pro Pro Leu Pro His Gly Lys Glu Cys Val His Leu Val
625                 630                 635                 640
Thr Ala Asn Gly Tyr Thr Pro Leu His Gln Ala Ala Gln Gln Gly His
                645                 650                 655
Thr His Ile Ile Asn Val Leu Leu Gln Asn Asn Ala Ser Pro Asn Glu
            660                 665                 670
Leu Thr Val Thr Val Thr Glu Lys His Lys Met Asn Val Pro Glu Thr
            675                 680                 685
Met Asn Glu Val Leu Asp Met Ser Asp Asp Glu Val Arg Lys Ala Asn
690                 695                 700
Ala Pro Glu Met Leu Ser Asp Gly Glu Tyr Ile Ser Asp Val Glu Glu
705                 710                 715                 720
Gly Asn Arg Cys Thr Trp Tyr Lys Ile Pro Lys Val Gln Glu Phe Thr
                725                 730                 735
Val Lys Thr Asp Thr Phe Lys Arg Glu Ala Phe Asp Val Gly Leu Leu
            740                 745                 750
Ser Thr Ser Ala Gly Glu Asp Ala Met Thr Gly Asp Thr Asp Lys Tyr
            755                 760                 765
Leu Gly Pro Gln Asp Leu Lys Glu Leu Gly Asp Asp Ser Leu Pro Ala
            770                 775                 780
Glu Gly Tyr Met Gly Phe Ser Leu Gly Ala Arg Ser Ala Arg Phe Leu
785                 790                 795                 800
Val Ser Phe Met Val Asp Ala Arg Gly Gly Ser Met Arg Gly Ser Arg
                805                 810                 815
His His Gly Met Arg Ile Ile Pro Pro Arg Lys Cys Thr Ala Pro
            820                 825                 830
Thr Arg Ile Thr Cys Arg Leu Val Lys Arg His Lys Leu Ala Asn Pro
            835                 840                 845
Pro Pro Met Val Glu Gly Glu Gly Leu Ala Ser Arg Leu Val Glu Met
            850                 855                 860
Gly Pro Ala Gly Ala Gln Phe Leu Gly Pro Val Ile Val Glu Ile Pro
865                 870                 875                 880
His Phe Gly Ser Met Arg Gly Lys Glu Arg Glu Leu Ile Val Leu Arg
                885                 890                 895
Ser Glu Asn Gly Glu Thr Trp Lys Glu His Gln Phe Asp Ser Lys Asn
            900                 905                 910
Glu Asp Leu Thr Glu Leu Leu Asn Gly Met Asp Glu Glu Leu Asp Ser
            915                 920                 925
Pro Glu Glu Leu Gly Lys Lys Arg Ile Cys Arg Ile Ile Thr Lys Asp
            930                 935                 940
Phe Pro Gln Tyr Phe Ala Val Val Ser Arg Ile Lys Gln Glu Ser Asn
945                 950                 955                 960
Gln Ile Gly Pro Glu Gly Gly Ile Leu Ser Ser Thr Val Pro Leu
                965                 970                 975
Val Gln Ala Ser Phe Pro Glu Gly Ala Leu Thr Lys Arg Ile Arg Val
            980                 985                 990
Gly Leu Gln Ala Gln Pro Val Pro Asp Glu Ile Val Lys Lys Ile Leu
            995                 1000                1005
```

-continued

```
Gly Asn Lys Ala Thr Phe Ser Pro Ile Val Thr Val Glu Pro Arg Arg
    1010                1015                1020
Arg Lys Phe His Lys Pro Ile Thr Met Thr Ile Pro Val Pro Pro Pro
1025                1030                1035                1040
Ser Gly Glu Gly Val Ser Asn Gly Tyr Lys Gly Asp Thr Thr Pro Asn
                1045                1050                1055
Leu Arg Leu Leu Cys Ser Ile Thr Gly Gly Thr Ser Pro Ala Gln Trp
            1060                1065                1070
Glu Asp Ile Thr Gly Thr Thr Pro Leu Thr Phe Ile Lys Asp Cys Val
        1075                1080                1085
Ser Phe Thr Thr Asn Val Ser Ala Arg Tyr Gly Asn Lys Gly Phe Gln
    1090                1095                1100
Lys Ala Val Leu Glu Gly Lys Pro Ile Tyr Val Asp Cys Tyr Gly Asn
1105                1110                1115                1120
Leu Ala Pro Leu Thr Lys Gly Gln Gln Leu Val Phe Asn Phe Tyr
                1125                1130                1135
Ser Phe Lys Glu Asn Arg Leu Pro Phe Ser Ile Lys Ile Arg Asp Thr
            1140                1145                1150
Ser Gln Glu Pro Cys Gly Arg Leu Ser Phe Leu Lys Glu Pro Lys Thr
        1155                1160                1165
Thr Lys Gly Leu Pro Gln Thr Ala Val Cys Asn Leu Asn Ile Thr Leu
    1170                1175                1180
Pro Ala His Lys Lys Ile Glu Lys Thr Asp Arg Arg Gln Ser Phe Ala
1185                1190                1195                1200
Ser Leu Ala Leu Arg Lys Arg Tyr Ser Tyr Leu Thr Glu Pro Gly Met
                1205                1210                1215
Lys Glu Lys Lys Met Gln Ser Glu Leu Ser Asp Glu Glu Ser Thr
            1220                1225                1230
Ser Arg Asn Thr Ser Leu Ser Glu Thr Ser Arg Gly Gly Gln Pro Ser
        1235                1240                1245
Val Thr Thr Lys Ser Ala Arg Asp Lys Lys Thr Glu Ala Ala Pro Leu
    1250                1255                1260
Lys Ser Lys Ser Glu Lys Ala Gly Ser Glu Lys Arg Ser Ser Arg Arg
1265                1270                1275                1280
Thr Ala Asp Ala Leu Thr Ser Val Leu Thr Lys Ile Asn Arg Ile Asp
                1285                1290                1295
Ile Val Thr Leu Leu Glu Gly Pro Ile Phe Asp Tyr Gly Asn Ile Ser
            1300                1305                1310
Gly Thr Arg Ser Phe Ala Asp Glu Asn Asn Val Phe His Asp Pro Val
        1315                1320                1325
Asp Gly Tyr Pro Ser Leu Gln Val Glu Leu Glu Thr Pro Thr Gly Leu
    1330                1335                1340
His Tyr Thr Pro Thr Pro Phe Gln Gln Asp Asp Tyr Phe Ser Asp
1345                1350                1355                1360
Ile Ser Ser Ile Glu Ser Pro Leu Arg Thr Pro Ser Arg Leu Ser Asp
                1365                1370                1375
Gly Leu Val Pro Ser Gln Gly Asn Ile Glu His Ser Ala Asp Gly Pro
            1380                1385                1390
Pro Val Val Thr Ala Glu Asp Ala Ser Leu Glu Asp Ser Lys Leu Glu
        1395                1400                1405
Asp Ser Val Pro Leu Thr Glu Met Pro Glu Ala Val Asp Val Asp Glu
    1410                1415                1420
```

-continued

```
Ser Gln Leu Glu Asn Val Cys Leu Ser Glu Tyr Pro Gln Tyr Leu Gly
1425                1430                1435                1440

Asn Leu Ala Gly Ser Pro Lys Asp Val Lys Pro Ala Glu Pro Arg Lys
            1445                1450                1455

Leu Gly Val Ser Ser Glu Gln Glu Lys Gly Lys Ser Gly Pro Asp
1460                1465                1470

Glu Glu Met Met Glu Glu Lys Leu Lys Ser Leu Phe Glu Asp Ile Gln
    1475                1480                1485

Leu Glu Glu Gly Val Glu Ser Glu Glu Met Thr Glu Glu Lys Val Gln
1490                1495                1500

Ala Ile Leu Lys Arg Val Gln Gln Ala Glu Leu Glu Met Ser Ser Ile
1505                1510                1515                1520

Thr Gly Trp Gln Asn Glu Thr Ser Ser Gly Asn Leu Glu Ser Cys Ala
            1525                1530                1535

Gln Ala Arg Arg Val Thr Gly Gly Leu Leu Asp Arg Leu Asp Asp Ser
        1540                1545                1550

Pro Asp Gln Cys Arg Asp Ser Ile Thr Ser Tyr Leu Lys Gly Glu Ala
    1555                1560                1565

Gly Lys Phe Glu Ala Asn Gly Ser His Thr Glu Ile Thr Pro Glu Ala
1570                1575                1580

Lys Thr Lys Ser Tyr Phe Pro Glu Ser Gln Asn Asp Val Gly Lys Gln
1585                1590                1595                1600

Ser Thr Lys Glu Thr Leu Lys Pro Lys Ile His Gly Ser Gly His Val
            1605                1610                1615

Glu Glu Pro Ala Ser Pro Leu Ala Ala Tyr Gln Lys Ser Leu Glu Glu
        1620                1625                1630

Thr Ser Lys Leu Ile Ile Glu Glu Thr Lys Pro Cys Val Pro Asp Leu
    1635                1640                1645

Lys Asp Ser Glu Ser Asp Ser Ser Glu Glu Glu Arg Arg Val Thr
1650                1655                1660

Thr Arg Val Ile Arg Arg Arg Leu Ile Ile Lys Gly Glu Glu Ala Lys
1665                1670                1675                1680

Asn Ile Pro Gly Glu Ser Val Thr Glu Glu Gln Phe Thr Asp Glu Glu
            1685                1690                1695

Gly Asn Leu Ile Thr Arg Lys Gly Glu Gly Phe Lys Val Lys Thr Lys
        1700                1705                1710

Lys Glu Ile Arg His Val Glu Lys Lys Ser His Ser
    1715                1720
```

<210> SEQ ID NO 44
<211> LENGTH: 1305
<212> TYPE: DNA
<213> ORGANISM: Homo Sapien

<400> SEQUENCE: 44

| | |
|---|---|
| atggaggagg cggcggcggg ggctacgaag gcgtcttcga gacgtgaagc cgaggagatg | 60 |
| aagctggagc cattacaaga gcgtgagccc gcgccggagg agaacttgac gtggagcagc | 120 |
| agcggcggcg acgagaagtt tatgacatca gggtttgaag acaagcaatc aacctgtgag | 180 |
| acaaaggaac aggagccaaa attggtgaaa cccaagaaaa agagaagaaa aaagtcagtc | 240 |
| tatactgtag gcctgagagg gctaatcaat cttgggaaca cttgtttat gaattgtatt | 300 |
| gtccaggcac ttacccatat tcctctactg aaagatttct tcctctctga caagcacaaa | 360 |
| tgtataatga caagccccag cttgtgtctg gtctgtgaaa tgtcttcgct ttttcatgct | 420 |

-continued

```
atgtactctg ggagccgaac tcctcacatt ccctataagt tactgcatct gatatggatc      480
catgcagaac atttagcagg gtacaggcag caggatgccc atgagttcct tattgcaata      540
ttagacgtgc tacatagaca cagcaaagat gatagtggtg ggcaggaggc caataacccc      600
aactgctgta actgcatcat agaccaaatc tttacaggtg gcctgcaatc agatgtcaca      660
tgtcaagcct gccatagtgt ttctaccacc atagacccat gctgggacat cagtttggac      720
ttgcctggct cttgtgccac attcgattcc cagaacccag agagggctga cagcacagtg      780
agcagggatg accacatacc aggaatcccc tcacttacag actgtctaca gtggtttaca      840
aggccagagc acctaggaag cagtgccaaa atcaaatgca atagttgcca aagctaccag      900
gagtctacta aacagctcac aatgaaaaaa ttacccattg tggcttgttt tcatctcaag      960
cggtttgagc atgtaggcaa acagaggcga aagattaata cctttatctc ctttcccttg     1020
gagctggaca tgactccgtt tttggcctct actaaagaga gcagaatgaa agaaggccag     1080
ccaccaacag attgtgtgcc caatgagaat aagtattcct tgtttgcagt gattaatcac     1140
catggaactt tggaaagtgg ccactatacc agcttcatcc ggcaacaaaa ggaccagtgg     1200
ttcagctgtg atgatgccat catcaccaag gctaccattg aggacttact ctacagtgaa     1260
gggtatttac tgttctatca caaacagggt ctagagaaag actag                     1305
```

<210> SEQ ID NO 45
<211> LENGTH: 434
<212> TYPE: PRT
<213> ORGANISM: Homo Sapien

<400> SEQUENCE: 45

| Met | Glu | Glu | Ala | Ala | Gly | Ala | Thr | Lys | Ala | Ser | Ser | Arg | Arg | Glu |
|---|---|---|---|---|---|---|---|---|---|---|---|---|---|---|
| 1 | | | | 5 | | | | | 10 | | | | | 15 |

| Ala | Glu | Glu | Met | Lys | Leu | Glu | Pro | Leu | Gln | Glu | Arg | Glu | Pro | Ala | Pro |
|---|---|---|---|---|---|---|---|---|---|---|---|---|---|---|---|
| | | | 20 | | | | | 25 | | | | | 30 | | |

| Glu | Glu | Asn | Leu | Thr | Trp | Ser | Ser | Gly | Gly | Asp | Glu | Lys | Phe | Met |
|---|---|---|---|---|---|---|---|---|---|---|---|---|---|---|
| | | | 35 | | | | | 40 | | | | | 45 | | |

| Thr | Ser | Gly | Phe | Glu | Asp | Lys | Gln | Ser | Thr | Cys | Glu | Thr | Lys | Glu | Gln |
|---|---|---|---|---|---|---|---|---|---|---|---|---|---|---|---|
| | 50 | | | | | 55 | | | | | 60 | | | | |

| Glu | Pro | Lys | Leu | Val | Lys | Pro | Lys | Lys | Arg | Arg | Lys | Lys | Ser | Val |
|---|---|---|---|---|---|---|---|---|---|---|---|---|---|---|
| 65 | | | | 70 | | | | | 75 | | | | | 80 |

| Tyr | Thr | Val | Gly | Leu | Arg | Gly | Leu | Ile | Asn | Leu | Gly | Asn | Thr | Cys | Phe |
|---|---|---|---|---|---|---|---|---|---|---|---|---|---|---|---|
| | | | | 85 | | | | | 90 | | | | | 95 | |

| Met | Asn | Cys | Ile | Val | Gln | Ala | Leu | Thr | His | Ile | Pro | Leu | Leu | Lys | Asp |
|---|---|---|---|---|---|---|---|---|---|---|---|---|---|---|---|
| | | | 100 | | | | | 105 | | | | | 110 | | |

| Phe | Phe | Leu | Ser | Asp | Lys | His | Lys | Cys | Ile | Met | Thr | Ser | Pro | Ser | Leu |
|---|---|---|---|---|---|---|---|---|---|---|---|---|---|---|---|
| | | 115 | | | | | 120 | | | | | 125 | | | |

| Cys | Leu | Val | Cys | Glu | Met | Ser | Ser | Leu | Phe | His | Ala | Met | Tyr | Ser | Gly |
|---|---|---|---|---|---|---|---|---|---|---|---|---|---|---|---|
| | 130 | | | | | 135 | | | | | 140 | | | | |

| Ser | Arg | Thr | Pro | His | Ile | Pro | Tyr | Lys | Leu | Leu | His | Leu | Ile | Trp | Ile |
|---|---|---|---|---|---|---|---|---|---|---|---|---|---|---|---|
| 145 | | | | | 150 | | | | | 155 | | | | | 160 |

| His | Ala | Glu | His | Leu | Ala | Gly | Tyr | Arg | Gln | Gln | Asp | Ala | His | Glu | Phe |
|---|---|---|---|---|---|---|---|---|---|---|---|---|---|---|---|
| | | | | 165 | | | | | 170 | | | | | 175 | |

| Leu | Ile | Ala | Ile | Leu | Asp | Val | Leu | His | Arg | His | Ser | Lys | Asp | Asp | Ser |
|---|---|---|---|---|---|---|---|---|---|---|---|---|---|---|---|
| | | | 180 | | | | | 185 | | | | | 190 | | |

| Gly | Gly | Gln | Glu | Ala | Asn | Asn | Pro | Asn | Cys | Cys | Asn | Cys | Ile | Ile | Asp |
|---|---|---|---|---|---|---|---|---|---|---|---|---|---|---|---|
| | | 195 | | | | | 200 | | | | | 205 | | | |

| Gln | Ile | Phe | Thr | Gly | Gly | Leu | Gln | Ser | Asp | Val | Thr | Cys | Gln | Ala | Cys |
|---|---|---|---|---|---|---|---|---|---|---|---|---|---|---|---|
| | 210 | | | | | 215 | | | | | 220 | | | | |

His Ser Val Ser Thr Thr Ile Asp Pro Cys Trp Asp Ile Ser Leu Asp
225                 230                 235                 240

Leu Pro Gly Ser Cys Ala Thr Phe Asp Ser Gln Asn Pro Glu Arg Ala
            245                 250                 255

Asp Ser Thr Val Ser Arg Asp Asp His Ile Pro Gly Ile Pro Ser Leu
            260                 265                 270

Thr Asp Cys Leu Gln Trp Phe Thr Arg Pro Glu His Leu Gly Ser Ser
        275                 280                 285

Ala Lys Ile Lys Cys Asn Ser Cys Gln Ser Tyr Gln Glu Ser Thr Lys
290                 295                 300

Gln Leu Thr Met Lys Lys Leu Pro Ile Val Ala Cys Phe His Leu Lys
305                 310                 315                 320

Arg Phe Glu His Val Gly Lys Gln Arg Arg Lys Ile Asn Thr Phe Ile
                325                 330                 335

Ser Phe Pro Leu Glu Leu Asp Met Thr Pro Phe Leu Ala Ser Thr Lys
            340                 345                 350

Glu Ser Arg Met Lys Glu Gly Gln Pro Pro Thr Asp Cys Val Pro Asn
355                 360                 365

Glu Asn Lys Tyr Ser Leu Phe Ala Val Ile Asn His Gly Thr Leu
370                 375                 380

Glu Ser Gly His Tyr Thr Ser Phe Ile Arg Gln Gln Lys Asp Gln Trp
385                 390                 395                 400

Phe Ser Cys Asp Asp Ala Ile Ile Thr Lys Ala Thr Ile Glu Asp Leu
                405                 410                 415

Leu Tyr Ser Glu Gly Tyr Leu Leu Phe Tyr His Lys Gln Gly Leu Glu
            420                 425                 430

Lys Asp

<210> SEQ ID NO 46
<211> LENGTH: 1337
<212> TYPE: DNA
<213> ORGANISM: Homo Sapien

<400> SEQUENCE: 46
gcagtaacag ccaccctcct gtcatcgcca ccaccgttgt gtccctcaag gctgcgaatc      60
tgacgtatat gccctcatcc agcggctctg cccgctcgct gaattgtgga tgcagcagtg     120
ccagctgctg cactgtggca acctacgaca aggacaatca ggcccagacc caagccattg     180
ccgctggcac caccaccact gccatcggaa cctctaccac ctgccctgct aaccagatgg     240
tcaacaataa tgagaataca ggctctctaa gtccatcaag tggggtgggc agccctgtgt     300
cagggacccc caagcagcta gccagcatca aaataatcta ccccaatgac ttggcaaaga     360
agatgaccaa atgcagcaag agtcacctgc cgagtcaggg ccctgtcatc attgactgca     420
ggcccttcat ggagtacaac aagagtcaca tccaaggagc tgtccacatt aactgtgccg     480
ataagatcag ccggcggaga ctgcagcagg gcaagatcac tgtcctagac ttgatttcct     540
gtagggaagg caaggactct ttcaagagga tcttttccaa agaaattata gtttatgatg     600
agaataccaa tgagccaagc cgagtgatgc cctcccagcc acttcacata gtcctcgagt     660
ccctgaagag agaaggcaaa gaacctctgg tgttgaaagg tggacttagt agttttaagc     720
agaaccatga aacctctgt gacaactccc tccagctcca agagtgccgg gaggtggggg     780
gcggcgcatc cgcggcctcg agcttgctac ctcagcccat ccccaccacc cctgacatcg     840
agaacgctga gctcacccc atcttgccct tcctgttcct tggcaatgag caggatgctc     900

-continued

```
aggacctgga caccatgcag cggctgaaca tcggctacgt catcaacgtc accactcatc    960
ttcccctcta ccactatgag aaaggcctgt tcaactacaa gcggctgcca gccactgaca   1020
gcaacaagca gaacctgcgg cagtactttg aagaggcttt tgagttcatt gaggaagctc   1080
accagtgtgg gaagggcttt ctcatccact gccaggctgg ggtgtcccgc tccgccacca   1140
tcgtcatcgc ttacttgatg aagcacactc ggatgaccat gactgatgct tataaatttg   1200
tcaaaggcaa acgaccaatt atctccccaa accttaactt catggggcag ttgctagagt   1260
tcgaggaaga cctaaacaac ggtgtgacac cgagaatcct tacaccaaag ctgatgggcg   1320
tggagacggt tgtgtga                                                   1337
```

<210> SEQ ID NO 47
<211> LENGTH: 444
<212> TYPE: PRT
<213> ORGANISM: Homo Sapien

<400> SEQUENCE: 47

```
Ser Asn Ser His Pro Val Ile Ala Thr Thr Val Ser Leu Lys
1               5                   10                  15

Ala Ala Asn Leu Thr Tyr Met Pro Ser Ser Gly Ser Ala Arg Ser
            20                  25                  30

Leu Asn Cys Gly Cys Ser Ser Ala Ser Cys Cys Thr Val Ala Thr Tyr
            35                  40                  45

Asp Lys Asp Asn Gln Ala Gln Thr Gln Ala Ile Ala Ala Gly Thr Thr
50                  55                  60

Thr Thr Ala Ile Gly Thr Ser Thr Thr Cys Pro Ala Asn Gln Met Val
65                  70                  75                  80

Asn Asn Asn Glu Asn Thr Gly Ser Leu Ser Pro Ser Ser Gly Val Gly
                85                  90                  95

Ser Pro Val Ser Gly Thr Pro Lys Gln Leu Ala Ser Ile Lys Ile Ile
                100                 105                 110

Tyr Pro Asn Asp Leu Ala Lys Lys Met Thr Lys Cys Ser Lys Ser His
            115                 120                 125

Leu Pro Ser Gln Gly Pro Val Ile Ile Asp Cys Arg Pro Phe Met Glu
    130                 135                 140

Tyr Asn Lys Ser His Ile Gln Gly Ala Val His Ile Asn Cys Ala Asp
145                 150                 155                 160

Lys Ile Ser Arg Arg Arg Leu Gln Gln Gly Lys Ile Thr Val Leu Asp
                165                 170                 175

Leu Ile Ser Cys Arg Glu Gly Lys Asp Ser Phe Lys Arg Ile Phe Ser
            180                 185                 190

Lys Glu Ile Ile Val Tyr Asp Glu Asn Thr Asn Glu Pro Ser Arg Val
        195                 200                 205

Met Pro Ser Gln Pro Leu His Ile Val Leu Glu Ser Leu Lys Arg Glu
    210                 215                 220

Gly Lys Glu Pro Leu Val Leu Lys Gly Gly Leu Ser Ser Phe Lys Gln
225                 230                 235                 240

Asn His Glu Asn Leu Cys Asp Asn Ser Leu Gln Leu Gln Glu Cys Arg
                245                 250                 255

Glu Val Gly Gly Gly Ala Ser Ala Ser Ser Leu Leu Pro Gln Pro
                260                 265                 270

Ile Pro Thr Thr Pro Asp Ile Glu Asn Ala Glu Leu Thr Pro Ile Leu
        275                 280                 285
```

```
Pro Phe Leu Phe Leu Gly Asn Glu Gln Asp Ala Gln Asp Leu Asp Thr
    290                 295                 300
Met Gln Arg Leu Asn Ile Gly Tyr Val Ile Asn Val Thr Thr His Leu
305                 310                 315                 320
Pro Leu Tyr His Tyr Glu Lys Gly Leu Phe Asn Tyr Lys Arg Leu Pro
                325                 330                 335
Ala Thr Asp Ser Asn Lys Gln Asn Leu Arg Gln Tyr Phe Glu Glu Ala
            340                 345                 350
Phe Glu Phe Ile Glu Glu Ala His Gln Cys Gly Lys Gly Leu Leu Ile
        355                 360                 365
His Cys Gln Ala Gly Val Ser Arg Ser Ala Thr Ile Val Ile Ala Tyr
    370                 375                 380
Leu Met Lys His Thr Arg Met Thr Met Thr Asp Ala Tyr Lys Phe Val
385                 390                 395                 400
Lys Gly Lys Arg Pro Ile Ile Ser Pro Asn Leu Asn Phe Met Gly Gln
                405                 410                 415
Leu Leu Glu Phe Glu Glu Asp Leu Asn Asn Gly Val Thr Pro Arg Ile
            420                 425                 430
Leu Thr Pro Lys Leu Met Gly Val Glu Thr Val Val
        435                 440

<210> SEQ ID NO 48
<211> LENGTH: 3378
<212> TYPE: DNA
<213> ORGANISM: Homo Sapien

<400> SEQUENCE: 48
ttgcaggaat catcggaatc cttcaccatg gcatccagcc cggcccagcg tcggcgaggc        60
aatgatcctc tcacctccag ccctggccga agctcccggc gtactgatgc cctcacctcc       120
agccctggcc gtgaccttcc accatttgag gatgagtccg aggggctcct aggcacagag       180
gggcccctgg aggaagaaga ggatggagag gagctcattg agatggcat ggaaagggac       240
taccgcgcca tcccagagct ggacgcctat gaggccgagg gactggctct ggatgatgag       300
gacgtagagg agctgacggc cagtcagagg gaggcagcag agcgggccat gcggcagcgt       360
gaccgggagc tggccgcggg cctgggccgc atgcgccgtg ggctcctgta tgacagcgat       420
gaggaggacg aggagcgccc tgcccgcaag cgccgccagg tggagcgggc cacggaggac       480
ggcgaggagg acgaggagat gattgagagc atcgagaacc tggaggatct caaaggccac       540
tctgtgcgcg agtgggtgag catggcgggc ccccggctgg agatccacca ccgcttcaag       600
aacttcctgc gcactcacgt cgacagccac ggccacaacg tcttcaagga gcgcatcagc       660
gacatgtgca aagagaaccg tgagagcctg gtggtgaact atgaggactt ggcagccagg       720
gagcacgtgc tggcctactt cctgcctgag gcaccggcgg agctgctgca gatctttgat       780
gaggctgccc tggaggtggt actggccatg taccccaagt acgaccgcat caccaaccac       840
atccatgtcc gcatctccca cctgcctctg gtggaggagc tgcgctcgct gaggcagctg       900
catctgaacc agctgatccg caccagtggg gtggtgacca gctgcactgg cgtcctgccc       960
cagctcagca tggtcaagta caactgcaac aagtgcaatt cgtcctgggg tcctttctgc      1020
cagtcccaga accaggaggt gaaccaggct cctgtcctg agtgccagtc ggccggcccc      1080
tttgaggtca catggagga gaccatctat cagaactacc agcgtatccg aatccaggag      1140
agtccaggca aagtggcggc tggcggctg ccccgctcca aggacgccat tctcctcgca      1200
gatctggtgg acagctgcaa gccaggagac gagatagagc tgactggcat ctatcacaac      1260
```

```
aactatgatg gctccctcaa cactgccaat ggcttccctg tctttgccac tgtcatccta   1320
gccaaccacg tggccaagaa ggacaacaag gttgctgtag gggaactgac cgatgaagat   1380
gtgaagatga tcactagcct ctccaaggat cagcagatcg gagagaagat ctttgccagc   1440
attgctcctt ccatctatgg tcatgaagac atcaagagag gcctggctct ggccctgttc   1500
ggaggggagc ccaaaaaccc agtgggcaag cacaaggtac gtggtgatat caacgtgctc   1560
ttgtgcggag accctggcac agcgaagtcg cagtttctca agtatattga gaaagtgtcc   1620
agccgagcca tcttcaccac tggccagggg gcgtcggctg tgggcctcac ggcgtatgtc   1680
cagcggcacc ctgtcagcag ggagtggacc ttggaggctg gggccctggt tctggctgac   1740
cgaggagtgt gtctcattga tgaatttgac aagatgaatg accaggacag aaccagcatc   1800
catgaggcca tggagcaaca gagcatctcc atctcgaagg ctggcatcgt cacctccctg   1860
caggctcgct gcacggtcat tgctgccgcc aaccccatag gagggcgcta cgaccccctcg  1920 ctgactttct ctgagaacgt ggacctcaca gagcccatca tctcacgctt tgacatcctg   1980
tgtgtggtga gggacaccgt ggacccagtc caggacgaga tgctggcccg cttcgtggtg   2040
ggcagccacg tcagacacca ccccagcaac aaggaggagg aggggctggc caatggcagc   2100
gctgctgagc ccgccatgcc caacacgtat ggcgtggagc ccctgcccca ggaggtcctg   2160
aagaagtaca tcatctacgc caaggagagg gtccacccga agctcaacca gatggaccag   2220
gacaaggtgg ccaagatgta cagtgacctg aggaaagaat ctatggcgac aggcagcatc   2280
cccattacgg tgcggcacat cgagtccatg atccgcatgg cggaggccca cgcgcgcatc   2340
catctgcggg actatgtgat cgaagacgac gtcaacatgg ccatccgcgt gatgctggag   2400
agcttcatag acacacagaa gttcagcgtc atgcgcagca tgcgcaagac ttttgcccgc   2460
tacctttcat tccggcgtga caacaatgag ctgttgctct tcatactgaa gcagttagtg   2520
gcagagcagg tgacatatca gcgcaaccgc tttggggccc agcaggacac tattgaggtc   2580
cctgagaagg acttggtgga taaggctcgt cagatcaaca tccacaacct ctctgcattt   2640
tatgacagtg agctcttcag gatgaacaag ttcagccacg acctgaaaag gaaaatgatc   2700
ctgcagcagt tctgaggccc tatgccatcc ataaggattc cttgggattc tggtttgggg   2760
tggtcagtgc cctctgtgct ttatggacac aaaaccagag cacttgatga actcggggta   2820
ctagggtcag ggcttatagc aggatgtctg gctgcacctg gcatgactgt ttgtttctcc   2880
aagcctgctt tgtgcttctc acctttgggt gggatgcctt gccagtgtgt cttacttggt   2940
tgctgaacat cttgccacct ccgagtgctt tgtctccact cagtaccttg gatcagagct   3000
gctgagttca ggatgcctgc gtgtggttta ggtgttagcc ttcttacatg gatgtcagga   3060
gagctgctgc cctcttggcg tgagttgcgt attcaggctg cttttgctgc ctttggccag   3120
agagctggtt gaagatgttt gtaatcgttt tcagtctcct gcaggtttct gtgcccctgt   3180
ggtggaagag ggcacgacag tgccagcgca gcgttctggg ctcctcagtc gcagggtgg    3240 gatgtgagtc atgcggatta tccactcgcc acagttatca gctgccattg ctccctgtct   3300
gtttccccac tctcttatttt gtgcattcgg tttggtttct gtagttttaa ttttttaataa  3360 agttgaataa aatataaa                                                  3378
```

<210> SEQ ID NO 49
<211> LENGTH: 904
<212> TYPE: PRT
<213> ORGANISM: Homo Sapien

<400> SEQUENCE: 49

```
Leu Gln Glu Ser Ser Glu Ser Phe Thr Met Ala Ser Ser Pro Ala Gln
1               5                   10                  15

Arg Arg Arg Gly Asn Asp Pro Leu Thr Ser Ser Pro Gly Arg Ser Ser
            20                  25                  30

Arg Arg Thr Asp Ala Leu Thr Ser Ser Pro Gly Arg Asp Leu Pro Pro
        35                  40                  45

Phe Glu Asp Glu Ser Glu Gly Leu Leu Gly Thr Glu Gly Pro Leu Glu
    50                  55                  60

Glu Glu Glu Asp Gly Glu Glu Leu Ile Gly Asp Gly Met Glu Arg Asp
65                  70                  75                  80

Tyr Arg Ala Ile Pro Glu Leu Asp Ala Tyr Glu Ala Glu Gly Leu Ala
                85                  90                  95

Leu Asp Asp Glu Asp Val Glu Glu Leu Thr Ala Ser Gln Arg Glu Ala
            100                 105                 110

Ala Glu Arg Ala Met Arg Gln Arg Asp Arg Glu Ala Gly Arg Gly Leu
        115                 120                 125

Gly Arg Met Arg Arg Gly Leu Leu Tyr Asp Ser Asp Glu Glu Asp Glu
130                 135                 140

Glu Arg Pro Ala Arg Lys Arg Gln Val Glu Arg Ala Thr Glu Asp
145                 150                 155                 160

Gly Glu Glu Asp Glu Glu Met Ile Glu Ser Ile Glu Asn Leu Glu Asp
                165                 170                 175

Leu Lys Gly His Ser Val Arg Glu Trp Val Ser Met Ala Gly Pro Arg
            180                 185                 190

Leu Glu Ile His His Arg Phe Lys Asn Phe Leu Arg Thr His Val Asp
        195                 200                 205

Ser His Gly His Asn Val Phe Lys Glu Arg Ile Ser Asp Met Cys Lys
210                 215                 220

Glu Asn Arg Glu Ser Leu Val Val Asn Tyr Glu Asp Leu Ala Ala Arg
225                 230                 235                 240

Glu His Val Leu Ala Tyr Phe Leu Pro Glu Ala Pro Ala Glu Leu Leu
                245                 250                 255

Gln Ile Phe Asp Glu Ala Ala Leu Glu Val Val Leu Ala Met Tyr Pro
            260                 265                 270

Lys Tyr Asp Arg Ile Thr Asn His Ile His Val Arg Ile Ser His Leu
        275                 280                 285

Pro Leu Val Glu Glu Leu Arg Ser Leu Arg Gln Leu His Leu Asn Gln
290                 295                 300

Leu Ile Arg Thr Ser Gly Val Val Thr Ser Cys Thr Gly Val Leu Pro
305                 310                 315                 320

Gln Leu Ser Met Val Lys Tyr Asn Cys Asn Lys Cys Asn Phe Val Leu
                325                 330                 335

Gly Pro Phe Cys Gln Ser Gln Asn Gln Glu Val Lys Pro Gly Ser Cys
            340                 345                 350

Pro Glu Cys Gln Ser Ala Gly Pro Phe Glu Val Asn Met Glu Glu Thr
        355                 360                 365

Ile Tyr Gln Asn Tyr Gln Arg Ile Arg Ile Gln Glu Ser Pro Gly Lys
370                 375                 380

Val Ala Ala Gly Arg Leu Pro Arg Ser Lys Asp Ala Ile Leu Leu Ala
385                 390                 395                 400

Asp Leu Val Asp Ser Cys Lys Pro Gly Asp Glu Ile Glu Leu Thr Gly
                405                 410                 415
```

-continued

```
Ile Tyr His Asn Asn Tyr Asp Gly Ser Leu Asn Thr Ala Asn Gly Phe
            420                 425                 430

Pro Val Phe Ala Thr Val Ile Leu Ala Asn His Val Ala Lys Lys Asp
            435                 440                 445

Asn Lys Val Ala Val Gly Glu Leu Thr Asp Glu Asp Val Lys Met Ile
    450                 455                 460

Thr Ser Leu Ser Lys Asp Gln Gln Ile Gly Glu Lys Ile Phe Ala Ser
465                 470                 475                 480

Ile Ala Pro Ser Ile Tyr Gly His Glu Asp Ile Lys Arg Gly Leu Ala
                485                 490                 495

Leu Ala Leu Phe Gly Glu Pro Lys Asn Pro Gly Gly Lys His Lys
            500                 505                 510

Val Arg Gly Asp Ile Asn Val Leu Leu Cys Gly Asp Pro Gly Thr Ala
            515                 520                 525

Lys Ser Gln Phe Leu Lys Tyr Ile Glu Lys Val Ser Ser Arg Ala Ile
530                 535                 540

Phe Thr Thr Gly Gln Gly Ala Ser Ala Val Gly Leu Thr Ala Tyr Val
545                 550                 555                 560

Gln Arg His Pro Val Ser Arg Glu Trp Thr Leu Glu Ala Gly Ala Leu
            565                 570                 575

Val Leu Ala Asp Arg Gly Val Cys Leu Ile Asp Glu Phe Asp Lys Met
            580                 585                 590

Asn Asp Gln Asp Arg Thr Ser Ile His Glu Ala Met Glu Gln Gln Ser
            595                 600                 605

Ile Ser Ile Ser Lys Ala Gly Ile Val Thr Ser Leu Gln Ala Arg Cys
            610                 615                 620

Thr Val Ile Ala Ala Asn Pro Ile Gly Gly Arg Tyr Asp Pro Ser
625                 630                 635                 640

Leu Thr Phe Ser Glu Asn Val Asp Leu Thr Glu Pro Ile Ile Ser Arg
            645                 650                 655

Phe Asp Ile Leu Cys Val Val Arg Asp Thr Val Asp Pro Val Gln Asp
            660                 665                 670

Glu Met Leu Ala Arg Phe Val Val Gly Ser His Val Arg His His Pro
            675                 680                 685

Ser Asn Lys Glu Glu Gly Leu Ala Asn Gly Ser Ala Ala Glu Pro
    690                 695                 700

Ala Met Pro Asn Thr Tyr Gly Val Glu Pro Leu Pro Gln Glu Val Leu
705                 710                 715                 720

Lys Lys Tyr Ile Ile Tyr Ala Lys Glu Arg Val His Pro Lys Leu Asn
                725                 730                 735

Gln Met Asp Gln Asp Lys Val Ala Lys Met Tyr Ser Asp Leu Arg Lys
            740                 745                 750

Glu Ser Met Ala Thr Gly Ser Ile Pro Ile Thr Val Arg His Ile Glu
            755                 760                 765

Ser Met Ile Arg Met Ala Glu Ala His Ala Arg Ile His Leu Arg Asp
770                 775                 780

Tyr Val Ile Glu Asp Asp Val Asn Met Ala Ile Arg Val Met Leu Glu
785                 790                 795                 800

Ser Phe Ile Asp Thr Gln Lys Phe Ser Val Met Arg Ser Met Arg Lys
                805                 810                 815

Thr Phe Ala Arg Tyr Leu Ser Phe Arg Arg Asp Asn Asn Glu Leu Leu
            820                 825                 830
```

-continued

```
Leu Phe Ile Leu Lys Gln Leu Val Ala Glu Gln Val Thr Tyr Gln Arg
        835                 840                 845

Asn Arg Phe Gly Ala Gln Asp Thr Ile Glu Val Pro Glu Lys Asp
        850                 855                 860

Leu Val Asp Lys Ala Arg Gln Ile Asn Ile His Asn Leu Ser Ala Phe
865                 870                 875                 880

Tyr Asp Ser Glu Leu Phe Arg Met Asn Lys Phe Ser His Asp Leu Lys
                885                 890                 895

Arg Lys Met Ile Leu Gln Gln Phe
            900

<210> SEQ ID NO 50
<211> LENGTH: 2815
<212> TYPE: DNA
<213> ORGANISM: Homo Sapien

<400> SEQUENCE: 50
```

| | | | | | |
|---|---|---|---|---|---|
| gcctggagcc | gacaccaccg | ccatcatgcc | ggccgtgtcc | aagggcgatg | ggatgcgggg | 60 |
| gctcgcggtg | ttcatctccg | acatccggaa | ctgtaagagc | aaagaggcgg | aaattaagag | 120 |
| aatcaacaag | gaactggcca | acatccgctc | caagttcaaa | ggagacaaag | ccttggatgg | 180 |
| ctacagtaag | aaaaaatatg | gttacctgtt | catttctgtg | ctggtgaact | cgaactcgga | 240 |
| gctgatccgc | ctcatcaaca | acgccatcaa | gaatgacctg | ccagccgca | accccacctt | 300 |
| catgtgcctg | ccctgcact | gcatcgccaa | cgtgggcagc | cgggagatgg | gcgaggcctt | 360 |
| tgccgctgac | atcccccgca | tcctggtggc | cggggacagc | atggacagtg | tcaagcagag | 420 |
| tgcggccctg | tgcctccttc | gactgtacaa | ggcctcgcct | gacctggtgc | ccatgggcga | 480 |
| gtggacggcg | cgtgtggtac | acctgctcaa | tgaccagcac | atgggtgtgg | tcacggccgc | 540 |
| cgtcagcctc | atcacctgtc | tctgcaagaa | gaacccagat | gacttcaaga | cgtgcgtctc | 600 |
| tctggctgtg | tcgcgcctga | gccggatcgt | ctcctctgcc | tccaccgacc | tccaggacta | 660 |
| cacctactac | ttcgtcccag | cacctggct | ctcggtgaag | ctcctgcggc | tgctgcagtg | 720 |
| ctaccccgcct | ccagaggatg | cggctgtgaa | ggggcggctg | gtggaatgtc | tggagactgt | 780 |
| gctcaacaag | gcccaggagc | cccccaaatc | caagaaggtg | cagcattcca | acgccaagaa | 840 |
| cgccatcctc | ttcgagacca | tcagcctcat | catccactat | gacagtgagc | ccaacctcct | 900 |
| ggttcgggcc | tgcaaccagc | tgggccagtt | cctgcagcac | cgggagacca | acctgcgcta | 960 |
| cctggccctg | gagagcatgt | gcacgctggc | cagctccgag | ttctcccatg | aagccgtcaa | 1020 |
| gacgcacatt | gacaccgtca | tcaatgccct | caagacggag | cgggacgtca | gcgtgcggca | 1080 |
| gcgggcggct | gacctcctct | acgccatgtg | tgaccggagc | aatgccaagc | agatcgtgtc | 1140 |
| ggagatgctg | cggtacctgg | agacggcaga | ctacgccatc | cgcgaggaga | tcgtcctgaa | 1200 |
| ggtggccatc | ctggccgaga | agtacgccgt | ggactacagc | tggtacgtgg | acaccatcct | 1260 |
| caacctcatc | cgcattgcgg | gcgactacgt | gagtgaggag | gtgtggtacc | gtgtgctaca | 1320 |
| gatcgtcacc | aaccgtgatg | acgtccaggg | ctatgccgcc | aagaccgtct | ttgaggcgct | 1380 |
| ccaggcccct | gcctgtcacg | agaacatggt | gaaggttggc | ggctacatcc | ttgggagtt | 1440 |
| tgggaacctg | attgctgggg | accccgctc | cagcgtggcc | acgcgggcgc | tgctgctgtc | 1500 |
| cacctacatc | aagttcatca | acctcttccc | cgagaccaag | gccaccatcc | agggcgtcct | 1560 |
| gcgggccggc | tcccagctgc | gcaatgctga | cgtggagctg | cagcagcgag | ccgtggagta | 1620 |
| cctcacccctc | agctcagtgg | ccagcaccga | cgtcctggcc | acggtgctgg | aggagatgcc | 1680 |

-continued

```
gcccttcccc gagcgcgagt cgtccatcct ggccaagctg aaacgcaaga aggggccagg      1740
ggccggcagc gccctggacg atggccggag ggaccccagc agcaacgaca tcaacggggg      1800
catggagccc accccagca ctgtgtcgac gccctcgccc tccgccgacc tcctggggct      1860
gcgggcagcc cctccccgg cagcaccccc ggcttctgca ggagcaggga accttctggt      1920
ggacgtcttc gatggcccgg ccgcccagcc cagcctgggg cccaccccg aggaggcctt      1980
cctcagccca ggtcctgagg acatcggccc tcccattccg gaagccgatg agttgctgaa      2040
taagtttgtg tgtaagaaca acggggtcct gttcgagaac cagctgctgc agatcggagt      2100
caagtcagag ttccgacaga acctgggccg catgtatctc ttctatggca acaagacctc      2160
ggtgcagttc cagaatttct cacccactgt ggttcacccg ggagacctcc agactcatat      2220
cctctcaggc ccggcccagc ctcctgcctc tccacgtcgg ccttcctcac cgtggggaag      2280
ccggctgacc cagctggctg tgcagaccaa gcgcgtggcg gcgcaggtgg acggcggcgc      2340
gcaggtgcag caggtgctca atatcgagtc cctgcgggac ttcctgacgc cccgctgct      2400
gtccgtgcgc ttccggtacg gtggcgcccc ccaggccctc accctgaagc tcccagtgac      2460
catcaacaag ttcttccagc ccaccgagat ggcggcccag gatttcttcc agcgctggaa      2520
gcagctgagc ctccctcaac aggaggcgca gaaaatcttc aaagccaacc accccatgga      2580
cgcagaagtt actaaggcca agcttctggg gtttggctct gctctcctgg acaatgtgga      2640
ccccaaccct gagaacttcg tgggggcggg gatcatccag actaaagccc tgcaggtggg      2700
ctgtctgctt cggctggagc ccaatgccca ggcccagatg taccggctga ccctgcgcac      2760
cagcaaggag cccgtctccc gtcacctgtg tgagctgctg gcacagcagt tctga          2815
```

<210> SEQ ID NO 51
<211> LENGTH: 937
<212> TYPE: PRT
<213> ORGANISM: Homo Sapien

<400> SEQUENCE: 51

```
Pro Gly Ala Asp Thr Thr Ala Ile Met Pro Ala Val Ser Lys Gly Asp
1               5                   10                  15

Gly Met Arg Gly Leu Ala Val Phe Ile Ser Asp Ile Arg Asn Cys Lys
                20                  25                  30

Ser Lys Glu Ala Glu Ile Lys Arg Ile Asn Lys Glu Leu Ala Asn Ile
            35                  40                  45

Arg Ser Lys Phe Lys Gly Asp Lys Ala Leu Asp Gly Tyr Ser Lys Lys
        50                  55                  60

Lys Tyr Gly Tyr Leu Phe Ile Ser Val Leu Val Asn Ser Asn Ser Glu
65                  70                  75                  80

Leu Ile Arg Leu Ile Asn Asn Ala Ile Lys Asn Asp Leu Ala Ser Arg
                85                  90                  95

Asn Pro Thr Phe Met Cys Leu Ala Leu His Cys Ile Ala Asn Val Gly
                100                 105                 110

Ser Arg Glu Met Gly Glu Ala Phe Ala Ala Asp Ile Pro Arg Ile Leu
            115                 120                 125

Val Ala Gly Asp Ser Met Asp Ser Val Lys Gln Ser Ala Ala Leu Cys
        130                 135                 140

Leu Leu Arg Leu Tyr Lys Ala Ser Pro Asp Leu Val Pro Met Gly Glu
145                 150                 155                 160

Trp Thr Ala Arg Val Val His Leu Leu Asn Asp Gln His Met Gly Val
                165                 170                 175
```

-continued

```
Val Thr Ala Ala Val Ser Leu Ile Thr Cys Leu Cys Lys Lys Asn Pro
            180                 185                 190

Asp Asp Phe Lys Thr Cys Val Ser Leu Ala Val Ser Arg Leu Ser Arg
            195                 200                 205

Ile Val Ser Ser Ala Ser Thr Asp Leu Gln Asp Tyr Thr Tyr Tyr Phe
            210                 215                 220

Val Pro Ala Pro Trp Leu Ser Val Lys Leu Leu Arg Leu Leu Gln Cys
225                 230                 235                 240

Tyr Pro Pro Pro Glu Asp Ala Ala Val Lys Gly Arg Leu Val Glu Cys
                245                 250                 255

Leu Glu Thr Val Leu Asn Lys Ala Gln Glu Pro Pro Lys Ser Lys Lys
            260                 265                 270

Val Gln His Ser Asn Ala Lys Asn Ala Ile Leu Phe Glu Thr Ile Ser
            275                 280                 285

Leu Ile Ile His Tyr Asp Ser Glu Pro Asn Leu Leu Val Arg Ala Cys
            290                 295                 300

Asn Gln Leu Gly Gln Phe Leu Gln His Arg Glu Thr Asn Leu Arg Tyr
305                 310                 315                 320

Leu Ala Leu Glu Ser Met Cys Thr Leu Ala Ser Ser Glu Phe Ser His
                325                 330                 335

Glu Ala Val Lys Thr His Ile Asp Thr Val Ile Asn Ala Leu Lys Thr
            340                 345                 350

Glu Arg Asp Val Ser Val Arg Gln Arg Ala Ala Asp Leu Leu Tyr Ala
            355                 360                 365

Met Cys Asp Arg Ser Asn Ala Lys Gln Ile Val Ser Glu Met Leu Arg
            370                 375                 380

Tyr Leu Glu Thr Ala Asp Tyr Ala Ile Arg Glu Glu Ile Val Leu Lys
385                 390                 395                 400

Val Ala Ile Leu Ala Glu Lys Tyr Ala Val Asp Tyr Ser Trp Tyr Val
                405                 410                 415

Asp Thr Ile Leu Asn Leu Ile Arg Ile Ala Gly Asp Tyr Val Ser Glu
            420                 425                 430

Glu Val Trp Tyr Arg Val Leu Gln Ile Val Thr Asn Arg Asp Asp Val
            435                 440                 445

Gln Gly Tyr Ala Ala Lys Thr Val Phe Glu Ala Leu Gln Ala Pro Ala
            450                 455                 460

Cys His Glu Asn Met Val Lys Val Gly Gly Tyr Ile Leu Gly Glu Phe
465                 470                 475                 480

Gly Asn Leu Ile Ala Gly Asp Pro Arg Ser Ser Val Ala Thr Arg Ala
                485                 490                 495

Leu Leu Leu Ser Thr Tyr Ile Lys Phe Ile Asn Leu Phe Pro Glu Thr
            500                 505                 510

Lys Ala Thr Ile Gln Gly Val Leu Arg Ala Gly Ser Gln Leu Arg Asn
            515                 520                 525

Ala Asp Val Glu Leu Gln Gln Arg Ala Val Glu Tyr Leu Thr Leu Ser
            530                 535                 540

Ser Val Ala Ser Thr Asp Val Leu Ala Thr Val Leu Glu Glu Met Pro
545                 550                 555                 560

Pro Phe Pro Glu Arg Glu Ser Ser Ile Leu Ala Lys Leu Lys Arg Lys
                565                 570                 575

Lys Gly Pro Gly Ala Gly Ser Ala Leu Asp Asp Gly Arg Arg Asp Pro
            580                 585                 590

Ser Ser Asn Asp Ile Asn Gly Gly Met Glu Pro Thr Pro Ser Thr Val
```

```
                595                600                605
Ser Thr Pro Ser Pro Ser Ala Asp Leu Leu Gly Leu Arg Ala Ala Pro
    610                615                620
Pro Pro Ala Ala Pro Pro Ala Ser Ala Gly Ala Gly Asn Leu Leu Val
625                630                635                640
Asp Val Phe Asp Gly Pro Ala Ala Gln Pro Ser Leu Gly Pro Thr Pro
                645                650                655
Glu Glu Ala Phe Leu Ser Pro Gly Pro Glu Asp Ile Gly Pro Pro Ile
                660                665                670
Pro Glu Ala Asp Glu Leu Leu Asn Lys Phe Val Cys Lys Asn Asn Gly
                675                680                685
Val Leu Phe Glu Asn Gln Leu Leu Gln Ile Gly Val Lys Ser Glu Phe
690                695                700
Arg Gln Asn Leu Gly Arg Met Tyr Leu Phe Tyr Gly Asn Lys Thr Ser
705                710                715                720
Val Gln Phe Gln Asn Phe Ser Pro Thr Val Val His Pro Gly Asp Leu
                725                730                735
Gln Thr His Ile Leu Ser Gly Pro Ala Gln Pro Pro Ala Ser Pro Arg
                740                745                750
Arg Pro Ser Ser Pro Trp Gly Ser Arg Leu Thr Gln Leu Ala Val Gln
                755                760                765
Thr Lys Arg Val Ala Ala Gln Val Asp Gly Gly Ala Gln Val Gln Gln
        770                775                780
Val Leu Asn Ile Glu Cys Leu Arg Asp Phe Leu Thr Pro Pro Leu Leu
785                790                795                800
Ser Val Arg Phe Arg Tyr Gly Gly Ala Pro Gln Ala Leu Thr Leu Lys
                805                810                815
Leu Pro Val Thr Ile Asn Lys Phe Phe Gln Pro Thr Glu Met Ala Ala
                820                825                830
Gln Asp Phe Phe Gln Arg Trp Lys Gln Leu Ser Leu Pro Gln Gln Glu
                835                840                845
Ala Gln Lys Ile Phe Lys Ala Asn His Pro Met Asp Ala Glu Val Thr
    850                855                860
Lys Ala Lys Leu Leu Gly Phe Gly Ser Ala Leu Leu Asp Asn Val Asp
865                870                875                880
Pro Asn Pro Glu Asn Phe Val Gly Ala Gly Ile Ile Gln Thr Lys Ala
                885                890                895
Leu Gln Val Gly Cys Leu Leu Arg Leu Glu Pro Asn Ala Gln Ala Gln
            900                905                910
Met Tyr Arg Leu Thr Leu Arg Thr Ser Lys Glu Pro Val Ser Arg His
            915                920                925
Leu Cys Glu Leu Leu Ala Gln Gln Phe
    930                935

<210> SEQ ID NO 52
<211> LENGTH: 3313
<212> TYPE: DNA
<213> ORGANISM: Homo sapiens

<400> SEQUENCE: 52
tcacatcccc ttgaccctcc aatcaccctcg ggctcccatt tgattggaag gcggcaaagg       60
ctttaatctc cccttggtg cagctgcttt tgaagtgagt ttcctcgcca gagccccggc        120
tggacacgca gcggctcgca tcgcagagcg cagcgccggc gcggggccgc gagaacgcag       180
```

-continued

```
cgcaggggag cagcccgagg cggacaccgc gagccgcccg gcactcccgc agtccagccg    240
gctcctctag cccggccacg gctccgctgc gggccaccca ggattactcg cgtctggctc    300
caggcgccga gaaggcgcgc tgggcgcccg tggccgccgc gccagctcct cctcctcccg    360
ctgctcctgc tcccggggcg agcgcgcagc cccgagcccg ccccgcgcct cccggagccc    420
tcccccccgc tgctcccatg cgcgcgggtg gtcatgagc acagcgccct cgctttctgc     480
cctaagaagc agtaagcaca gcggcggcgg cggcggcgga ggcggaggcg gcggtgcaga    540
ccctgcctgg accagcgcgc tctctggaaa tagctccggc cccggcccag gctcgtcccc    600
ggccggcagc accaagcctt ttgtgcacgc cgtgccccc tctgacccc tgcgccaggc      660 caaccgcctg ccaatcaagg tgctgaagat gctgacggca cgaactggcc acattttgca    720
ccccgagtac ctgcagcccc tgccttccac gccggtcagc cccatcgagc tcgatgccaa    780
gaagagcccg ctggcgctgt tggcgcaaac atgttcgcag atcgggaagc ccgacccctc    840
gccctcctcc aaactctcct cggttgcctc aacggggc ggcgcgggcg gtgccggcgg      900
cggtgctgcg ggcgacaagg acaccaaatc gggcccctg aagctgagcg acatcggcgt     960
ggaggacaag tcgagtttca gccgtactc caaacccgc tcggataaga aggagccggg     1020
aggcggcggt ggaggcggtg gcggtggcgg gggcggcggc ggggtgtttt cgtcggagaa   1080
gtcgggattc cgggtaccga gcgccacctg ccagccattc acgcccagga caggcagccc   1140
gagctccagc gcctcggcct gctcgccggg aggtatgctg tcctcggccg ggggtgcccc   1200
ggagggcaag gacgacaaga aagacaccga cgtgggcggc ggtggcaagg gcaccggggg   1260
cgcctcggcc gaaggggac ccacggggct ggcacacggc cggattagct gcggcggcgg    1320
gattaatgtg gatgtgaacc agcatccgga tggggcccg ggaggcaagg ctctgggctc    1380
ggactgcggc ggttcatcgg gctccagctc cggctccggc cccagcgcgc ccacctcctc   1440
ctcagtgttg ggctctgggc tggtggctcc cgtgtcaccc tacaagccgg gccagacagt   1500
gttccctctg cctcccgcgg gtatgaccta cccaggcagc ctggccgggg cctacgccgg   1560
ctacccgccc cagttcctgc cacacggcgt ggcacttgac cccaccaagc cgggcagcct   1620
ggtgggggcg cagctggcgg cggccgcggc cgggtctctg ggctgcagta agccggccgg   1680
ctccagccct ttggccggag cgtctccgcc gtccgtgatg acagccagtt tgtgccggga   1740
cccttactgc ctcagctacc actgcgctag ccacctggca ggggcggcgg ccgccagcgc   1800
ttcttgcgca catgatccgg ctgctgcggc tgcggcgctg aagtccggat acccgctggt   1860
gtaccccacg cacccgctgc acggtgtgca ctcctcgcta acggccgccg cggctgctgg   1920
cgccacaccg ccctcctgg ccggccaccc cctctacccc tacggctttta tgctccctaa    1980 cgacccactc ccccacatct gcaactgggt gtcggccaac gggccgtgcg acaagcgctt   2040
cgccacgtcc gaagagctgc tgagccactt gcggacccat acggcatttc ccgggacaga   2100
caaactgctg tcgggctacc ccagctcgtc gtctctggcc agcgctgccg cggccgccat   2160
ggcttgccac atgcacatcc ccacctcggg cgcaccgggc agccctggga cgctggcgct   2220
gcgcagcccc caccacgcgc tgggactcag cagccgctac caccctact ccaagagccc    2280 gcttcccacg cctggcgccc ccgtgccggt gccgccgcc accggaccgt actactcccc    2340
ctacgccctc tacggacaga gactgaccac cgcctcggcg ctggggtatc agtgagggcg   2400
gccgggaggg cgagcgaggg agaggaggga gaggggagg ggaggagtcc agggagaggc    2460
gggatcacgg cccaggctgc tgacacccgc gcgtggggag gactcgggcc acgaaaggaa   2520
agaaatgtat accgtatcta tctacccgac agcagcgacc gagacccggt gggacactcc   2580
```

-continued

```
ccttctcccc actttcacct ccccacccaa actttataaa agttgaaaaa atatcatttg    2640 acttttata gaaaaaaaaa ggaaaaaata attgagaaag tgttcatctg aggactgcat    2700
cggtggacac tggtatttat ttatgttagc tccaagcgga ccggtggttc aaaagtgcat    2760
tatttagttt gagctctgta ggtaaaaagg aggtgggaaa aattttaaaa cttgagggta    2820
aaaatgtgga aaacaaaccc tcccatccct tgtagattat aaataaaagc aaaaccgcca    2880
cagaactaga ggtcttctct ttaatgttac tttaaaattg ctatgattgt attgtacgtt    2940
atttaatgtc tgattgaaac acaaatttac atgcatgttt gttacaaaaa aaatgaaaaa    3000
aaaagtcaca atttgtcagc tctgatttca aattgcaatt attttttaagg tgtataccat    3060 cgaagagaat gggtattttt ttgtatgtat tctggaagaa aacaacaaaa aaaaaagaaa    3120
aagaaaaaat tctattccaa aacctcattt gccttatttt gttctttaaa aggaacactt    3180
aactattttt aatttttaag tccacccgct gagaagggga caaggtttac gtcatgtact    3240
aaaataatag acaatgtatc gctttaaaga ttaaaattcc gtatatttga tgtattaaag    3300
ggttttactt ctt                                                      3313
```

<210> SEQ ID NO 53
<211> LENGTH: 646
<212> TYPE: PRT
<213> ORGANISM: Homo sapiens

<400> SEQUENCE: 53

```
Met Ser Thr Ala Pro Ser Leu Ser Ala Leu Arg Ser Ser Lys His Ser
 1               5                  10                  15

Gly Gly Gly Gly Gly Gly Gly Gly Gly Gly Ala Asp Pro Ala Trp
                20                  25                  30

Thr Ser Ala Leu Ser Gly Asn Ser Ser Gly Pro Gly Pro Gly Ser Ser
            35                  40                  45

Pro Ala Gly Ser Thr Lys Pro Phe Val His Ala Val Pro Pro Ser Asp
        50                  55                  60

Pro Leu Arg Gln Ala Asn Arg Leu Pro Ile Lys Val Leu Lys Met Leu
    65                  70                  75                  80

Thr Ala Arg Thr Gly His Ile Leu His Pro Glu Tyr Leu Gln Pro Leu
                85                  90                  95

Pro Ser Thr Pro Val Ser Pro Ile Glu Leu Asp Ala Lys Lys Ser Pro
               100                 105                 110

Leu Ala Leu Leu Ala Gln Thr Cys Ser Gln Ile Gly Lys Pro Asp Pro
           115                 120                 125

Ser Pro Ser Ser Lys Leu Ser Ser Val Ala Ser Asn Gly Gly Ala
       130                 135                 140

Gly Gly Ala Gly Gly Ala Ala Gly Asp Lys Asp Thr Lys Ser Gly
   145                 150                 155                 160

Pro Leu Lys Leu Ser Asp Ile Gly Val Glu Asp Lys Ser Ser Phe Lys
                165                 170                 175

Pro Tyr Ser Lys Pro Gly Ser Asp Lys Lys Glu Pro Gly Gly Gly Gly
            180                 185                 190

Gly Gly Gly Gly Gly Gly Gly Gly Gly Gly Val Ser Ser Glu
        195                 200                 205

Lys Ser Gly Phe Arg Val Pro Ser Ala Thr Cys Gln Pro Phe Thr Pro
    210                 215                 220

Arg Thr Gly Ser Pro Ser Ser Ala Ser Ala Cys Ser Pro Gly Gly
225                 230                 235                 240
```

-continued

```
Met Leu Ser Ser Ala Gly Gly Ala Pro Glu Gly Lys Asp Lys Lys
                245                 250                 255

Asp Thr Asp Val Gly Gly Gly Lys Gly Thr Gly Ala Ser Ala
            260                 265                 270

Glu Gly Gly Pro Thr Gly Leu Ala His Gly Arg Ile Ser Cys Gly Gly
            275                 280                 285

Gly Ile Asn Val Asp Val Asn Gln His Pro Asp Gly Pro Gly Gly
290                 295                 300

Lys Ala Leu Gly Ser Asp Cys Gly Gly Ser Ser Gly Ser Ser Ser Gly
305                 310                 315                 320

Ser Gly Pro Ser Ala Pro Thr Ser Ser Ser Val Leu Gly Ser Gly Leu
                325                 330                 335

Val Ala Pro Val Ser Pro Tyr Lys Pro Gly Gln Thr Val Phe Pro Leu
                340                 345                 350

Pro Pro Ala Gly Met Thr Tyr Pro Gly Ser Leu Ala Gly Ala Tyr Ala
                355                 360                 365

Gly Tyr Pro Pro Gln Phe Leu Pro His Gly Val Ala Leu Asp Pro Thr
370                 375                 380

Lys Pro Gly Ser Leu Val Gly Ala Gln Leu Ala Ala Ala Ala Gly
385                 390                 395                 400

Ser Leu Gly Cys Ser Lys Pro Ala Gly Ser Ser Pro Leu Ala Gly Ala
                405                 410                 415

Ser Pro Pro Ser Val Met Thr Ala Ser Leu Cys Arg Asp Pro Tyr Cys
                420                 425                 430

Leu Ser Tyr His Cys Ala Ser His Leu Ala Gly Ala Ala Ala Ser
        435                 440                 445

Ala Ser Cys Ala His Asp Pro Ala Ala Ala Ala Ala Leu Lys Ser
    450                 455                 460

Gly Tyr Pro Leu Val Tyr Pro Thr His Pro Leu His Gly Val His Ser
465                 470                 475                 480

Ser Leu Thr Ala Ala Ala Ala Ala Gly Ala Thr Pro Pro Ser Leu Ala
                485                 490                 495

Gly His Pro Leu Tyr Pro Tyr Gly Phe Met Leu Pro Asn Asp Pro Leu
                500                 505                 510

Pro His Ile Cys Asn Trp Val Ser Ala Asn Gly Pro Cys Asp Lys Arg
            515                 520                 525

Phe Ala Thr Ser Glu Glu Leu Leu Ser His Leu Arg Thr His Thr Ala
            530                 535                 540

Phe Pro Gly Thr Asp Lys Leu Leu Ser Gly Tyr Pro Ser Ser Ser Ser
545                 550                 555                 560

Leu Ala Ser Ala Ala Ala Ala Met Ala Cys His Met His Ile Pro
                565                 570                 575

Thr Ser Gly Ala Pro Gly Ser Pro Gly Thr Leu Ala Leu Arg Ser Pro
                580                 585                 590

His His Ala Leu Gly Leu Ser Ser Arg Tyr His Pro Tyr Ser Lys Ser
                595                 600                 605

Pro Leu Pro Thr Pro Gly Ala Pro Val Pro Val Pro Ala Ala Thr Gly
610                 615                 620

Pro Tyr Tyr Ser Pro Tyr Ala Leu Tyr Gly Gln Arg Leu Thr Thr Ala
625                 630                 635                 640

Ser Ala Leu Gly Tyr Gln
                645
```

TRANSGENIC *DROSOPHILA MELANOGASTER* EXPRESSING A β42 IN THE EYE

This application claims priority from U.S. Provisional Application 60/236,893, filed Sep. 29, 2000, and U.S. Provisional Application 60/298,309, filed Jun. 14, 2001, the disclosures of which are herein incorporated by reference.

BACKGROUND OF THE INVENTION

Alzheimer's disease (AD) is a neurological disorder resulting in the degeneration and eventual death of neurons in brain centers controlling memory, cognition and behavior. The hallmark of the disease is the formation of insoluble amyloid deposits (senile plaques), the major component of which is the 40–42 amino acid amyloid beta (Aβ) peptide, a proteolytic product of the amyloid precursor protein (APP). These plaques are widely believed to be the major causative agents leading to the degeneration and death of neuronal cells.

The three major known genes associated with inheritance of familial Alzheimer's disease (FAD) in humans are the transmembrane receptor amyloid precursor protein (APP) and the two presenilin (PS1 and PS2) genes. Missense mutations in these genes result in the increased production of the Aβ peptide, underscoring the importance of this peptide in contributing to the disease state. APP is cleaved at two sites, beta and gamma, to release a 40–42 amino acid peptide, Aβ (reviewed in Mills, J. and Reiner, P. B. (1999) *J. Neurochem* 72: 443–460). Missense mutations in APP near the gamma site (Goate, A. et al., (1991). *Nature* 349: 704–706.), where the C-terminal end of the peptide is cleaved, result in production of more Aβ 42, by altering the 40/42 ratio (Suzuki, N., et al. (1994). *Science* 264: 1336–1340). Mutations around the beta site result in more overall production of both forms (Mullan, M., et al. (1992). *Nat. Genet.* 1: 345–347.); Citron, M. et al. (1995). *Neuron* 14: 661–670).

The presenilins are multiple pass transmembrane proteins, the functions of which are currently a matter of debate. Missense mutations in presenilins increase the release of the Aβ 42 form (Borchelt, D. R., et al. (1996). *Neuron* 17: 1005–1013); Citron, M., et al. (1997). *Nat. Med.* 3: 67–72; Murayama, O. et al. (1999). *Neurosci. Lett.* 265: 61–63) and account for the majority of FAD cases (Sherrington, R., et al. (1995). *Nature* 375: 754–760).

Many studies have examined the roles of both the soluble and insoluble (aggregated) forms of Aβ and it is widely believed that the aggregated form of the peptide is responsible for the observed toxic effects (Pike, C. J., et al. (1993). *J. Neurosci.* 13: 1676–1687; Lorenzo, A. and Yankner, B. A. (1994). *Proc. Natl. Acad. Sci. USA* 91: 12243–12247; Giovannelli, L., et al (1998). *Neurosci.* 87: 349–357). There are a number of mechanisms that contribute to Aβ-induced death of neurons, including the disruption of intracellular calcium levels (for reviews, see Fraser, S. P., et al. (1997). *Trends Neurosci.* 20: 67–72; Mattson, M. P. (1997). *Physiol. Rev.* 77: 1081–1132; Coughlan, C. M. and Breen, K. C. (2000). *Pharmacol. and Ther.* 86: 111–144), the induction of an inflammatory response caused by activation of microglial cells (reviewed in Coughlan, C. M. and Breen, K. C. (2000). *Pharmacol. and Ther.* 86: 111–144) and the marked degeneration and/or disruption of the basal-forebrain cholinergic system, which is involved in learning and memory (reviewed in Hellstrom-Lindahl and Court, 2000, Behav. Brain Res. 113 (1–2): 159–68). Thus, it is clear that the deleterious effects of Aβ overproduction and its contribution to AD are numerous and complex.

Although a great amount of research has been dedicated to the study of Alzheimer's Disease and its general pathology, the genetic analysis of human neurodegenerative disorders is limited. As a result, the events that trigger the accumulation of beta amyloid, as well as the precise role of genes such as APP and others suspected to play a part in Alzheimer's Disease, is poorly understood.

Numerous contributions to the establishment of the central role of Aβ in the manifestation and progression of AD have come from studies in model systems. Transgenic mice expressing either wild type or mutant forms of APP exhibit AD pathology, in many cases developing amyloid plaques in an age-dependent fashion and in some cases displaying altered behavior and cognition (for reviews, see Price, D. L., et al (1998). *Annu. Rev. Genet.* 32: 461–493; van Leuven, F. (2000). *Progress in Neurobiol.* 61: 305–312). Transgenic mice expressing only the Aβ 42 peptide exhibit extensive neuronal degeneration in brain regions normally affected in AD, and 50% die at 12 months of age (LaFerla, F. M. et al. (1995). *Nature Genet.* 9: 21–30). The neural cells in these mice eventually apoptose, followed by astrogliosis and spongiosis. This demonstrates that Aβ 42 expression is toxic in vivo, and results in neuronal degeneration and apoptosis.

The use of *Drosophila* as a model organism has proven to be an important tool in the elucidation of human neurodegenerative disease pathways (reviewed in Fortini, M and Bonini, N. (2000). *Trends Genet.* 16: 161–167), as the *Drosophila* genome contains many relevant human orthologs that are extremely well conserved in function (Rubin, G. M., et al. (2000). *Science* 287: 2204–15). For example, *Drosophila melanogaster* carries a gene that is homologous to human APP which is involved in nervous system function. The gene, APP-like (Appl), is approximately 40% identical to the neurogenic isoform (695) of the human APP gene over three large domains (Rosen et al., PNAS USA 86:2478–2482 (1988)) and, like human APP695, is exclusively expressed in the nervous system. Flies deficient for the Appl gene show behavioral defects which can be rescued by the human APP gene, suggesting that the two genes have similar functions in the two organisms (Luo et al., Neuron 9:595–605 (1992)).

In addition, *Drosophila* models of polyglutamine repeat diseases (Jackson, G. R., et al (1998). *Neuron* 21: 633–642; Kazemi-Esfarani, P. and Benzer, S. (2000). *Science* 287: 1837–1840; Fernandez-Funez et al. (2000) *Nature* 408 (6808):101–6, and Parkinson's disease (Feany, M. B. and Bender, W. W. (2000). *Nature* 404: 394–398) closely mimic the disease state in humans, both at the cellular as well as the physiological level and have been used successfully to identify other genes that play a role in these diseases. Thus, the power of *Drosophila* as a model system is demonstrated in the ability to represent the disease state and to perform large scale genetic screens. This invention generally relates to a method to identify compounds and genes acting on the APP pathway in transgenic *Drosophia melanogaster* ectopically expressing genes related to AD. Expression of these transgenes can induce visible phenotypes and it is contemplated herein that genetic screens disclosed herein may be used to identify genes involved in the APP pathway by the identification of mutations that modify the induced visible phenotypes. The genes affected by these mutations will be called herein "genetic modifiers". It is contemplated herein that human homologs of genetic modifiers thus identified would be useful targets for development of therapeutics to treat conditions associated with abnormalities in the APP pathway, including, but not limited to, the development of Alzheimer Disease (AD) therapeutics. It is also contemplated herein that some of these human homologs might be occurring on an area of human chromosome 10, shown to be linked to Alzheimer's disease (Bertram et al., Ertekin-Taner et al., Myers et al., *Science* 290, 2302–2305, 2000). Such human homologs might have the potential to be genetically linked to AD and serve as markers for AD or as targets for the development of therapeutics to treat conditions associated with abnormalities in the APP pathway, including, but not limited to, the development of Alzheimer Disease (AD) therapeutics. Such human homologs might also be acting in cellular pathways involving genes linked to AD and these human homologs might be used to identify the genes in these pathways.

SUMMARY OF THE INVENTION

The present invention pertains to a transgenic fly whose genome comprises a DNA sequence encoding a polypeptide comprising the Abeta portion of human APP wherein said DNA sequence encodes Abeta40 (SEQ ID: NO 1) or Abeta42 (SEQ ID:NO 2), fused to a signal sequence, said DNA sequence operably linked to a tissue-specific expression control sequence; and expressing said DNA sequence, wherein expression of said DNA sequence results in said fly displaying an altered phenotype. In one particular embodiment, the DNA sequence encodes Abeta42, the tissue specific expression control sequence comprises the eye-specific promoter GMR and expression of the DNA sequence results in an altered phenotype referred to as the "rough eye" phenotype.

In a further aspect, the invention pertains to a transgenic fly whose genome comprises a DNA sequence encoding a polypeptide comprising the wild type C99 portion of human APP (SEQ. ID NO:3) or C99 portion of human APP with the London Mutation (SEQ ID NO: 4) fused to a signal sequence, said DNA sequence operably linked to a tissue-specific expression control sequence; and expressing said DNA sequence, wherein expression of said DNA sequence results in said fly displaying an altered phenotype. In one embodiment, the DNA sequence encodes the wild type C99, the tissue-specific expression control sequence is the UAS control element, which is activated by Gal4 protein produced in the brain by the 7B-Gal4 transgene and expression of the DNA sequence results in an altered phenotype characterized by a locomotory defect. In another particular embodiment, the DNA sequence encodes either the wild type C99 or the C99 portion of human APP with the London Mutation, the tissue-specific expression control sequence is UAS control element activated by Gal4 protein produced by the apterous-Gal4 transgene and expression of the DNA sequence results in an altered phenotype referred to as the "concave wing" phenotype.

In a further aspect, the invention pertains to a method to identify genetic modifiers of the APP pathway, said method comprising providing a transgenic fly whose genome comprises a DNA sequence encoding a polypeptide comprising the Abeta portion of human APP wherein said DNA sequence encodes Abeta40 (SEQ ID NO: 1) or Abeta42 (SEQ ID NO: 2), fused to a signal sequence, said DNA sequence operably linked to a tissue-specific expression control sequence; and expressing said DNA sequence, wherein expression of said DNA sequence results in said fly displaying an altered phenotype; crossing said transgenic fly with a fly containing a mutation in a known or predicted gene; and screening progeny of said crosses for flies that carry said DNA sequence and said mutation and display modified expression of the transgenic phenotype as compared to controls. In one embodiment, the DNA sequence encodes Abeta42, the tissue specific expression control sequence comprises the eye-specific promoter GMR and expression of said DNA sequence results in said fly displaying an altered phenotype referred to as the "rough eye" phenotype.

In a further aspect, the invention pertains to a method to identify genetic modifiers of the APP pathway, said method comprising: providing a transgenic fly whose genome comprises a DNA sequence encoding a polypeptide comprising the wild type C99 portion of human APP (SEQ. ID NO:3) or C99 portion of human APP with the London Mutation (SEQ ID NO: 4) fused to a signal sequence, said DNA sequence operably linked to a tissue-specific expression control sequence; and expressing said DNA sequence, wherein expression of said DNA sequence results in said fly displaying an altered phenotype; crossing said transgenic fly with a fly containing a mutation in a known or predicted gene; and, screening progeny of said crosses for flies that carry said DNA sequence and said mutation and display modified expression of the transgenic phenotype as compared to controls. In one embodiment, the DNA sequence encodes the wild type C99, the tissue-specific expression control sequence is the UAS control element, activated by Gal4 protein produced in the brain by the 7B-Gal4 transgene and expression of said DNA sequence results in said fly displaying an altered phenotype characterized by a locomotory defect. In another embodiment, the DNA sequence encodes either the wild type C99 or the C99 portion of human APP with the London Mutation, the tissue-specific expression control sequence is UAS control element activated by Gal4 protein produced by the apterous-Gal4 transgene and expression of said DNA sequence results in said fly displaying an altered phenotype referred to as the "concave wing" phenotype.

A further aspect of the invention pertains to a method to identify compounds that act on gene products involved in the APP pathway by assaying for compounds that can modify the phenotypes induced by expression of Abeta, said method comprising: providing a transgenic fly whose genome comprises a DNA sequence encoding a polypeptide comprising the Abeta portion of human APP wherein said DNA sequence encodes Abeta40 (SEQ ID NO: 1) or Abeta42 (SEQ ID NO: 2), fused to a signal sequence, said DNA sequence operably linked to a tissue-specific expression control sequence; and expressing said DNA sequence, wherein expression of said DNA sequence results in said fly displaying an altered phenotype; administering to said fly a candidate compound; and, assaying for changes in the phenotype of said fly as compared to the phenotype of a similar transgenic fly not administered the candidate compound. In one embodiment, the DNA sequence encodes Abeta42, the tissue specific expression control sequence is the eye-specific promoter GMR and expression of said DNA sequence results in said fly displaying an altered phenotype referred to as the "rough eye" phenotype.

Yet another aspect of the invention pertains to a method to identify compounds that act on gene products involved in the APP pathway by assaying for compounds that can modify the phenotypes induced by expression of C99, said method comprising: providing a transgenic fly whose genome comprises a DNA sequence encoding a polypeptide comprising the wild type C99 portion of human APP (SEQ. ID NO:3) or C99 portion of human APP with the London Mutation (SEQ ID NO: 4) fused to a signal sequence, said DNA sequence operably linked to a tissue-specific expression control sequence; and expressing said DNA sequence, wherein expression of said DNA sequence results in said fly displaying an altered phenotype; administering to said fly a candidate compound; and, assaying for changes in the phenotype of said fly as compared to the phenotype of a similar transgenic fly not administered the candidate compound. In one embodiment, the DNA sequence encodes wild type C99, the tissue-specific expression control sequence is the UAS control element activated by Gal4 protein produced in the brain by the 7B-Gal4 transgene and expression of said DNA sequence results in said fly displaying a phenotype characterized as a locomotory defect. In another embodiment, the DNA sequence encodes either wild type C99 or the C99 portion of human APP with the London Mutation, the tissue-specific expression control sequence is UAS control element activated by Gal4 protein produced by the apterous-Gal4 transgene and expression of said DNA sequence results in said fly displaying an altered phenotype referred to as the "concave wing" phenotype.

In yet another aspect, the invention pertains to a method for identifying genes involved in the onset or progression of conditions associated with abnormal regulation of the APP pathway, including but not limited to Alzheimer's Disease, and whose protein products might serve as potential markers for Alzheimer's Disease, said method comprising identifying the human homologs of fly genes that have been identified as genetic modifiers according to the methods of the present invention.

In yet another aspect, the invention pertains to a method for identifying genes involved in the onset or progression of conditions associated with abnormal regulation of the APP pathway, including but not limited to Alzheimer's Disease, and whose protein products might serve as potential markers for Alzheimer's Disease, said method comprising identifying human homologs of fly genetic modifier genes that are located close to the area of human chromosome 10 that is shown to have genetic linkage to Alzheimer's Disease.

In yet another aspect, the invention pertains to a method for identifying genes involved in the onset or progression of Alzheimer's Disease and whose protein products might serve as potential markers for AD, said method comprising identifying genes that are involved in the pathways regulated by the transcription factors encoded by the human sequences hCP50765 (SEQ ID NO. 35, encoded by the EGR2 gene), and hCP41313 (Seq ID NO 15, SEQ ID NO17 or SEQ ID NO 53, encoded by the human homolog of the Drosophila nocA gene), which human sequences are located close to the area of human chromosome 10 that is shown to have genetic linkage to Alzheimer's Disease.

In yet another aspect, the invention pertains to a method for identifying compounds useful for the treatment, prevention or amelioration of pathological conditions associated with defects in the APP pathway, including but not limited Alzheimer's Disease, comprising administering candidate compounds to an in vitro or in vivo model of Alzheimer's Disease; and assaying for changes in expression of a genetic homolog of a genetic modifier, wherein altered expression of any one of said homologs compared to levels in a control to which a candidate compound has not been administered indicates a compound of potential therapeutic value.

The invention also pertains to a method for the treatment, prevention or amelioration of pathological conditions associated with defects in the APP pathway, including, but not limited to Alzheimer's Disease, comprising administering to a subject in need thereof a therapeutically effective amount of a compound that may inhibit or promote the function of any one or more of the polypeptide encoded by the human homologs of the genetic modifiers identified herein.

The invention also pertains to a method for the treatment, prevention or amelioration of pathological conditions associated with defects in the regulation of the APP pathway, including but not limited to Alzheimer's Disease, comprising administering to a subject in need thereof a therapeutically effective amount of a pharmaceutical composition comprising any one or more substances selected from the group consisting of: triple helix DNA, antisense oligonucleotides or ribozymes, all complementary to the appropriate sequence of a mRNA deriving from any one or more of the human homologs of genetic modifier genes identified according to the methods of the present invention.

The invention also pertains to a method for the treatment, prevention or amelioration of pathological conditions associated with defects in the regulation of the APP pathway, including but not limited to Alzheimer's Disease, comprising administering to a subject in need thereof a therapeutically effective amount of a pharmaceutical composition comprising double stranded RNA molecules directed to one or more of the human homologs of the genetic modifiers identified according to the methods of the present invention.

In a further aspect, the invention pertains to a method for the treatment, prevention or amelioration of pathological conditions associated with defects in the APP pathway, including but not limited to Alzheimer's Disease, comprising administering to a subject in need thereof a therapeutically effective amount of a pharmaceutical composition comprising an antibody or antibodies and/or fragments thereof directed to the polypeptide encoded by any one or more of the human homolog of the genetic modifiers identified according to the methods of the present invention.

In a further aspect, the invention also pertains to a method for the diagnosis of pathological conditions associated with abnormalities in the APP pathway in a subject, including but not limited to Alzheimer's Disease, which comprises measuring the mRNA level or the level or activity of the polypeptides encoded by any one or more of the human homologs of a genetic modifier in a biological sample from a subject, wherein an abnormal level relative to the level thereof in a control subject is diagnostic of said conditions.

In a still further aspect, the invention pertains to a kit comprising the components necessary to detect expression levels of polypeptides encoded by any one or more of the human homologs of a genetic modifier or fragments thereof or polynucleotides encoding any one or more of said polypeptides or fragments thereof, in a biological sample from a subject, such kits comprising antibodies that bind to said polypeptides or to said fragments thereof, or oligonucleotide probes that hybridize with said polynucleotides or to said fragments thereof and instructions for using said kit.

In yet another aspect, the invention pertains to a pharmaceutical composition comprising substances selected from the group consisting of: antisense, ribozyme, double stranded RNA or triple helix nucleic acids directed to any one or more of the human homologs of a genetic modifier or fragments thereof, polypeptides encoded by any one or more of the human homologs of a genetic modifiers or fragments thereof, polynucleotides encoding said polypeptides or fragments thereof, and antibodies that bind to said polypeptides or fragments thereof, in conjunction with a suitable pharmaceutical carrier, excipient or diluent, for the treatment of pathological conditions associated with abnormalities in the APP pathway, including but not limited to, Alzheimer's Disease.

The invention also pertains to a method for the treatment of pathological conditions associated with abnormalities in APP pathway including but not limited to, Alzheimer's Disease, comprising introducing nucleic acids encoding any one or more of the human homologs of a genetic modifier into one or more tissues of a subject in need thereof resulting in that one or more proteins encoded by the nucleic acids are expressed and or secreted by cells within the tissue.

DETAILED DESCRIPTION OF THE INVENTION

All patent applications, patents, literature and website references cited herein are hereby incorporated by reference in their entirety.

In practicing the present invention, many conventional techniques in molecular biology and recombinant DNA are used. These techniques are well known and are explained in, for example, Current Protocols in Molecular Biology, Volumes I, II, and III, 1997 (F. M. Ausubel ed.); Sambrook et al., 1989, Molecular Cloning: A Laboratory Manual, Second Edition, Cold Spring Harbor Laboratory Press, Cold Spring Harbor, N.Y.; DNA Cloning: A Practical Approach, Volumes I and II, 1985 (D. N. Glover ed.); A Practical Guide to Molecular Cloning; the series, Methods in Enzymology (Academic Press, Inc.); Gene Transfer Vectors for Mammalian Cells, 1987 (J. H. Miller and M. P. Calos eds., Cold Spring Harbor Laboratory); and Methods in Enzymology Vol. 154 and Vol. 155 (Wu and Grossman, and Wu, eds., respectively). Well known Drosophila molecular genetics techniques can be found, for example, in Robert, D. B., Drosophila, A Practical Approach (IRL Press, Washington, D.C., 1986). Descriptions of flystocks can be found in the Flybase data base at http://flybase.bio.indiana.edu.

A "transgenic" organism as used herein refers to an organism that has had extra genetic material inserted into its genome. As used herein, a "transgenic fly" includes embryonic, larval and adult forms of Drosophia melanogaster that contain a DNA sequence from the same or another organism randomly inserted into their genome. Although Drosophia melanogaster is preferred, it is contemplated that any fly of the genus Drosophia may be used in the present invention.

As used herein, "ectopic" expression of the transgene refers to expression of the transgene in a tissue or cell or at a specific developmental stage where it is not normally expressed.

As used herein, "phenotype" refers to the observable physical or biochemical characteristics of an organism as determined by both genetic makeup and environmental influences.

As used herein, a compound that may "inhibit or promote the function of any or more of the polypeptides encoded by the human homolog of a genetic modifier" includes compounds that may do so indirectly (via down stream effects) or directly, by binding to or otherwise interacting with the protein and includes, but is not limited to, antagonists or agonists of the protein.

As used herein, a "stringent ortholog" is defined as meeting the following criteria: fly protein X has best match with human protein Y and fly protein X does not have a better match with another fly protein than with human protein Y and human protein Y has best match with fly protein X and human protein Y has no better match with another human protein than with fly protein X, wherein "X" and "Y" stand for any two fly and human proteins being compared.

A "putative ortholog" is defined herein as meeting only the following two criteria: fly protein X has best match with human protein Y and human protein Y has best match with fly protein X, regardless of whether fly protein X had a better match with another fly protein and/or whether human protein Y had a better match with another human protein. As disclosed herein, all other human/fly protein matches are deemed "homologs".

As used herein, the term "expression control sequence" refers to promoters and enhancers. The term "promoter" refers to DNA sequences which are recognized directly or indirectly and bound by a DNA-dependent RNA polymerase during the initiation of transcription and includes enhancer elements. Enhancers used in the present invention include the UAS element which is activated by the yeast Gal4 transcriptional regulator.

The term "transcription factor" refers to any protein required to initiate or regulate transcription in eukaryotes. For example, the eye-specific promoter GMR is a binding site for the eye-specific transcription factor, GLASS (Moses, K and Rubin, G M Genes Dev. 5(4):583–93 (1991)).

As used herein, the term "Abeta" (Aβ) refers to beta amyloid peptide which is a short (40–42 amino acid) peptide produced by proteolytic cleavage of APP by beta and gamma secretases. It is the primary component of amyloid depositions, the hallmark of AD and the cause of neuronal cell death and degeneration. Abeta peptide of the present invention includes, but is not limited to, peptides of 40 and 42 amino acids and are referred to, respectively, as Abeta40 (or Aβ40) (SEQ ID NO: 1) and Abeta42 (or Aβ42) (SEQ ID NO: 2).

"C99" refers to a peptide that contains the Abeta region plus the cytoplasmic tail of APP (SEQ ID NO: 3). As used herein, the term also includes the C99 London sequence, which carries the London FAD Alzheimer's associated mutation (SEQ ID NO: 4) (Goate, A., et al (1991). Nature 349: 704–706). Abeta and C99 peptides are well known to one of skill in the art (see, for example, Golde et al., Science 255:728–730 (1992); Coughlan, C. M. and Breen, K. C. (2000). Pharmacol. and Ther. 86: 111–144).

"UAS" region as used herein refers to an upstream activating sequence recognized by the GAL-4 transcriptional activator.

As used herein, a "signal sequence" refers to a short sequence of amino acids that determines the eventual location of a protein in a cell, for example, the N-terminal sequence or 20 or so amino acids that directs nascent secretory and transmembrane proteins to the endoplasmic reticulum. It is contemplated herein that any conventional signal sequence familiar to one of skill in the art may be used to ensure transfer of the encoded C99 or Abeta proteins through the secretory pathway, including, but not limited to, the signal sequence of endogenous Drosophia Appl or presenilin, or of the windbeutel gene, encoding for a ER (endoplasmic reticulum) resident protein (Konsolaki and Schupbach, Genes & Dev. 12: 120–131 (1998)), or the human pre-proenkephaline gene signal (SEQ ID NO: 5).

As used herein, a "control" fly refers to a larva or fly that is of the same genotype as larvae or flies used in the methods of the present invention except that the control larva or fly does not carry the mutation being tested for modification of phenotype, or is not administered candidate compounds.

As used herein, a "control subject" refers to an organism that does not suffer from a condition associated with abnormalities in the APP pathway.

As used herein, a "Drosophia transformation vector" is a DNA plasmid that contains transposable element sequences and can mediate integration of a piece of DNA in the genome of the organism. This technology is familiar to one of skill in the art.

As the term is used herein, the "rough eye" phenotype is characterized by disorganization of ommatidia and interommatidial bristles and can be caused by degeneration of neuronal cells. This phenotype is visible through a dissecting stereo-microscope.

As the term is used herein, the "concave wing" phenotype is characterized by abnormal folding of the fly wing such that the wings are bent upwards along their long margins.

As used herein, a "locomotory defect" refers to a phenotype wherein flies display impaired responses to mechanical agitation compared to wild type flies in conventional locomotory activity assays.

As used herein, the following and related phrases, pathological conditions associated with abnormalities in the APP pathway, conditions associated with abnormal regulation of the APP pathway, conditions related to Alzheimer's Disease, pathological conditions associated with defects in the APP pathway, all include, but are not limited to, Alzheimer's Disease, and include those conditions characterized by degeneration and eventual death of neurons in brain clusters controlling memory, cognition and behavior.

"Therapeutically effective amount" refers to that amount of active ingredient, for example compound or gene product which ameliorates the symptoms of the condition being treated.

Methods of obtaining transgenic organisms, including transgenic *Drosophila,* are well known to one skilled in the art. For example, a commonly used reference for P-element mediated transformation is Spradling, 1986. P element mediated transformation. In *Drosophila: A practical approach* (ed. D. B. Roberts), pp175–197. IRL Press, Oxford, UK)). The EP element technology refers to a binary system, utilizing the yeast Gal4 transcriptional activator, that is used to ectopically regulate the transcription of endogenous *Drosophia* genes. This technology is described in: Brand and Perrimon, 1993. Targeted gene expression as a means of altering cell fates and generating dominant phenotypes. Development 118, pp401–415 and in : Rorth et al, 1998. Systematic gain-of-function genetics in *Drosophila.* Development, 125(6), pp1049–1057.

The present invention discloses a transgenic fly, *Drosophia melanogaster,* that contains in its genome a DNA sequence encoding a polypeptide comprising the beta amyloid portion (SEQ ID NO:1 or SEQ ID NO: 2) or C99 portion of the human APP gene (SEQ ID NO: 3 or SEQ ID NO: 4) which is fused at its N-terminus according to conventional methods to a signal peptide sequence, for example, SEQ ID NO:5, to ensure transfer of the encoded polypeptide through the secretory pathway. The fused DNA sequences are operably linked to tissue-specific expression control sequences such as promoter regions or upstream activating sequences (UAS), depending on the expression system utilized. These expression control sequences include those that are specific for neural tissue in the fly and include organs such as the eye, wing, notum, brain, CNS and PNS. Under the control of these tissue specific control sequences, encoded peptides are transcribed to form mRNA which is translated into detectable levels of beta amyloid or C99 peptide and which causes altered phenotypes in the flies. By assaying for changes in these phenotypes, these flies can be used to identify genes or compounds that may affect the APP pathway and may provide insight into the molecular and biochemical mechanisms of the APP pathway and Alzheimer's Disease.

Conventional expression control systems may be used to achieve ectopic expression of proteins of interest, including the beta amyloid and C99 peptides of the present invention. Such expression may result in the disturbance of biochemical pathways and the generation of altered phenotypes. One such expression control system involves direct fusion of the DNA sequence to expression control sequences of tissue-specifically expressed genes, such as promoters or enhancers. Another expression control system that may be used is the binary Gal4-transcriptional activation system (Brand and Perrimon, *Development* 118:401–415 (1993)).

The Gal4 system uses the yeast transcriptional activator Gal4, to drive the expression of a gene of interest in a tissue specific manner. The Gal4 gene has been randomly inserted into the fly genome, using a conventional transformation system, so that it has come under the control of genomic enhancers that drive expression in a temporal and tissue-specific manner. Individual strains of flies have been established, called "drivers", that carry those insertions (Brand and Perrimon, *Development* 118:401–415 (1993)).

In the Gal4 system, a gene of interest is cloned into a transformation vector, so that its transcription is under the control of the UAS sequence (Upstream Activating Sequence), the Gal4-responsive element. When a fly strain that carries the UAS-gene of interest sequence is crossed to a fly strain that expresses the Gal4 gene under the control of a tissue specific enhancer, the gene will be expressed in a tissue specific pattern.

In order to generate phenotypes that are easily visible in adult tissues and can thus be used in genetic screens, Gal4 "drivers" that drive expression in later stages of the fly development may be used in the present invention. Using these drivers, expression would result in possible defects in the wings, the eyes, the legs, different sensory organs and the brain. These "drivers" include, for example, apterous-Gal4 (wings), elav-Gal4 (CNS), sevenless-Gal4, eyeless-Gal4 and pGMR-Gal4 (eyes). In addition, since Appl, the fly homologue of APP, is exclusively expressed in neural tissue, "driver" strains in which at least a subset of expression is directed to a part of the nervous system, are preferred. This includes the brain specific 7B-Gal4 driver. Descriptions of the Gal4 lines and notes about their specific expression patterns is available in Flybase (http://flybase.bio.indiana.edu).

Various DNA constructs may be used to generate the transgenic *Drosophila melanogaster* of the present invention. For example, the construct may contain the beta amyloid or C99 portion of the human APP gene fused to the pre-proenkephaline gene signal peptide sequence and operably linked to the eye-specific promoter, GMR. In another example, the construct may contain the beta amyloid portion or C99 of the human APP gene fused to the human pre-proenkephaline gene signal peptide sequence cloned into the pUAST vector (Brand and Perrimon, *Development* 118:401–415 (1993)) which places the UAS sequence upstream of the transcribed region. Insertion of these constructs into the fly genome may occur through P-element recombination, Hobo element recombination (Blackman et al., EMBO J. 8:211–217 (1989)), homologous recombination (Rong and Golic, Science 288:2013–2018 (2000)) or other standard techniques known to one of skill in the art.

As discussed above, an ectopically expressed gene may result in an altered phenotype by disruption of a particular biochemical pathway. Mutations in genes acting in the same biochemical pathway are expected to cause modification of the altered phenotype. Thus, the flies of the present invention can be used to identify genes acting in the APP pathway by crossing a C99 or Abeta transgenic fly with a fly containing a mutation in a known or predicted gene; and screening progeny of the crosses for flies that display quantitative or qualitative modification of the altered phenotype of the C99 or Abeta transgenic fly, as compared to controls. Thus, this system is extremely beneficial for the elucidation of the function of processed APP gene products, as well as the identification of other genes that directly or indirectly interact with them. Mutations that can be screened include, but are not limited to, loss-of-function alleles of known genes, deletion strains, "enhancer-trap" strains generated by the P-element and gain-of-function mutations generated by random insertions into the *Drosophia* genome of a Gal4-inducible construct that can activate the ectopic expression of genes in the vicinity of its insertion. It is contemplated herein that genes involved in the APP pathway can be identified in this manner and these genes can then serve as targets for the development of therapeutics to treat conditions associated with abnormalities in the APP pathway, leading to diseases, including but not limited to, Alzheimer's Disease.

The C99 and Abeta transgenic flies of the present invention may also be used in a method to identify compounds that may modify the APP pathway and may thus prove useful for the treatment of conditions discussed above. Said method may comprise administering candidate compounds to C99 or Abeta transgenic flies and then assaying for changes in the phenotype of the C99 or Abeta transgenic fly as compared to the phenotype of control C99 or Abeta transgenic flies that have not been administered the compound. For example, using conventional methods, candidate compounds can be fed to larvae expressing a beta amyloid or C99. The larvae can then be grown to the adult stage and modification of the C99 or Abeta-induced phenotype assayed. Candidate compounds may also be fed to adult flies and modifications of phenotype assayed.

The mechanism of action of compounds thus identified may be examined by comparing the phenotypes produced by genetic manipulation with those induced by the administration of a compound of interest. Such compounds include those that may ameliorate or worsen the altered phenotype created in the transgenic flies. Expression of a compound-induced phenotype similar to one associated with a known genetic modification would suggest that the compound has an effect on the same pathway that the genetic modification is affecting.

In addition to screening compounds in the transgenic flies of the present invention, such compounds may also be further assayed by employing in vitro and other in vivo models of AD using conventional methods. For example, numerous cell lines may be used as in vitro models of AD and are familiar to one of skill in the art, including, for example, the cell lines described in Xia et al, 1997 PNAS USA 94 (15):8208–13. In vivo models also exist and include, for example, the mouse model of AD disclosed in WO 94/00569.

Elucidation of the mechanism of action of compounds which affect the action of beta amyloid or C99 in the transgenic flies disclosed herein may also be performed using RNA profiling on chips (Affymetrix, Santa Clara) or using other conventional methods. For example, the RNA profiles of flies which have been administered candidate compounds may be assayed and compared to those of flies which have been genetically modified. Similar profiles would suggest that the compound acts in some way on the beta amyloid or C99 affected pathway.

It is contemplated herein that, in yet another aspect, the invention pertains to a method for identifying genes involved in the onset or progression of Alzheimer's Disease and whose protein products might serve as potential markers for AD, said method comprising identifying genes that are involved in the pathways regulated by the transcription factors encoded by the human sequences hCP50765 (SEQ ID NO. 35, encoded by the EGR2 gene), and hCP41313 (Seq ID NO 15, SEQ ID NO17 or SEQ ID NO 53, encoded by the human homolog of the *Drosophia* nocA gene), which human sequences are homologs of *Drosophia* genetic modifiers identified as described herein and are located close to the area of human chromosome 10 that is shown to have genetic linkage to Alzheimer's Disease. Identification of such genes, regulated by the above mentioned transcription factors, may be achieved using conventional methods, including but not limited to, a technology called SELEX, referenced in Tuerk and Gold, 1990, Science 249, 505–510 and Brown and Gold, 1995, Biochemistry 34, 14765–14774. For example, genes that are regulated by a specific transcription factor can be identified by determining the target DNA sequence of the specific transcription factor. Such target sequence identification can be achieved by different methods, including but not limited to SELEX. Once the target sequence is identified, the presence of this sequence in the upstream regulatory regions of known and predicted genes can be determined, using bio-informatics tools well known to one of skill in the art. Genes containing the target sequence in their upstream regulatory regions can be expected to be regulated by the specific transcription factor.

It is contemplated that compounds which can affect (e.g. inhibit or promote) the function or expression of proteins encoded by the human homologs of genetic modifiers identified according to the present invention may be useful to treat Alzheimer's Disease or other conditions associated with defects in the regulation of the APP pathway. In addition, it is also contemplated that, using conventional methods, antisense oligonucleotides, ribozymes, triple helix DNA and/or double stranded RNA of therapeutic value may be created based on the nucleotide sequences of these human homologs of genetic modifiers. The therapeutic use of antibodies directed to the polypeptides encoded by human homologs of genetic modifiers and created using conventional methods is also contemplated herein. Thus, an additional aspect of the invention relates to the administration of a pharmaceutical composition, in conjunction with a pharmaceutically acceptable carrier, excipient or diluent, for the treatment of Alzheimer's Disease and related conditions. Such pharmaceutical compositions may comprise the compounds, antisense oligonucleotides, ribozymes, triple helix DNA, double stranded RNA and/or antibodies discussed above. The compositions may also contain expression products of human homologs of the genetic modifiers (e.g. polypeptides or fragments thereof) identified according to the present invention. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a subject in need thereof alone, or in combination with other agents, drugs or hormones.

The pharmaceutical compositions encompassed by the invention may be administered by any number of routes including, but not limited to, oral, intravenous, intramuscular, intra-articular, intra-arterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of Remington's Pharmaceutical Sciences (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethyl cellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated m aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers may also be used for delivery. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of the compounds or gene products identified according to the present invention, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A "therapeutically effective dose" refers to that amount of active ingredient, for example compound or gene product which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between toxic and therapeutic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc. Pharmaceutical formulations suitable for oral administration of proteins are described, e.g., in U.S. Pat. Nos. 5,008,114; 5,505,962; 5,641,515; 5,681,811; 5,700,486; 5,766,633; 5,792,451; 5,853,748; 5,972,387; 5,976,569; and 6,051,561.

It is also contemplated herein that a method for the diagnosis of pathological conditions associated with abnormalities in the APP pathway in a subject, including but not limited to Alzheimer's Disease, is possible given the data of Table 1 For example, the method may comprise measuring the level of polypeptides encoded by any one or more of the human genetic homologs of the genes of Table 1 in a biological sample from a subject, wherein an abnormal level of any one or more of said polypeptides relative to the level thereof in a normal subject is diagnostic of said conditions. Such an assay could be performed using conventional technologies familiar to one of skill in the art.

In another embodiment, nucleic acids comprising a sequence encoding a human homolog of a genetic modifier or functional derivative thereof are administered to promote APP pathway function, by way of gene therapy. Gene therapy refers to therapy performed by the administration of a nucleic acid to a subject. In this embodiment of the invention, the nucleic acid produces its encoded protein that mediates a therapeutic effect by promoting normal APP pathway function.

Any of the methods for gene therapy available in the art can be used according to the present invention. Exemplary methods are described below.

In a preferred aspect, the therapeutic comprises the nucleic acid for a genetic modifier that is part of an expression vector that expresses a genetic modifier protein or fragment or chimeric protein thereof in a suitable host. In particular, such a nucleic acid has a promoter operably linked to the specific genetic modifier protein coding region, said promoter being inducible or constitutive, and, optionally, tissue-specific. In another particular embodiment, a nucleic acid molecule is used in which the modifier protein coding sequences and any other desired sequences are flanked by regions that promote homologous recombination at a desired site in the genome, thus providing for intrachromosomal expression of the modifier nucleic acid (Koller and Smithies, 1989, Proc. Natl. Acad. Sci. USA 86:8932–8935; Zijlstra et al., 1989, Nature 342:435–438).

Delivery of the nucleic acid into a patient may be either direct, in which case the patient is directly exposed to the nucleic acid or nucleic acid-carrying vector, or indirect, in which case, cells are first transformed with the nucleic acid in vitro, then transplanted into the patient. These two approaches are known, respectively, as in vivo or ex vivo gene therapy.

In a specific embodiment, the nucleic acid is directly administered in vivo, where it is expressed to produce the encoded product. This can be accomplished by any of numerous methods known in the art, e.g., by constructing it as part of an appropriate nucleic acid expression vector and administering it so that it becomes intracellular, e.g., by infection using a defective or attenuated retroviral or other viral vector (see, e.g., U.S. Pat. No. 4,980,286 and others mentioned infra), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering it in linkage to a peptide which is known to enter the nucleus, by administering it in linkage to a ligand subject to receptor-mediated endocytosis (see e.g., U.S. Pat. Nos. 5,166,320; 5,728,399; 5,874,297; and 6,030,954, all of which are incorporated by reference herein in their entirety) (which can be used to target cell types specifically expressing the receptors), etc. In another embodiment, a nucleic acid-ligand complex can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180; WO 92/22635; WO92/20316; WO93/14188; and WO 93/20221). Alternatively, the nucleic acid can be introduced intracellularly and incorporated within host cell DNA for expression, by homologous recombination (see, e.g., U.S. Pat. Nos. 5,413,923; 5,416,260; and 5,574,205; and Zijlstra et al., 1989, Nature 342:435–438).

In a specific embodiment, a viral vector that contains a modifier nucleic acid is used. For example, a retroviral vector can be used (see, e.g., U.S. Pat. Nos. 5,219,740; 5,604,090; and 5,834,182). These retroviral vectors have been modified to delete retroviral sequences that are not necessary for packaging of the viral genome and integration into host cell DNA. The modifier nucleic acid to be used in gene therapy is cloned into the vector, which facilitates delivery of the gene into a patient.

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Methods for conducting adenovirus-based gene therapy are described in, e.g., U.S. Pat. Nos. 5,824,544; 5,868,040; 5,871,722; 5,880,102; 5,882,877; 5,885,808; 5,932,210; 5,981,225; 5,994,106; 5,994,132; 5,994,134; 6,001,557; and 6,033,8843, all of which are incorporated by reference herein in their entirety.

Adeno-associated virus (AAV) has also been proposed for use in gene therapy. Methods for producing and utilizing AAV are described, e.g., in U.S. Pat. Nos. 5,173,414; 5,252,479; 5,552,311; 5,658,785; 5,763,416; 5,773,289; 5,843,742; 5,869,040; 5,942,496; and 5,948,675, all of which are incorporated by reference herein in their entirety.

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc.

Numerous techniques are known in the art for the introduction of foreign genes into cells and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. In a preferred embodiment, epithelial cells are injected, e.g., subcutaneously. In another embodiment, recombinant skin cells may be applied as a skin graft onto the patient. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the patient.

In an embodiment in which recombinant cells are used in gene therapy, a modifier nucleic acid is introduced into the cells such that it is expressible by the cells or their progeny, and the recombinant cells are then administered in vivo for therapeutic effect. In a specific embodiment, stem or progenitor cells are used. Any stem-and/or progenitor cells that can be isolated and maintained in vitro can potentially be used in accordance with this embodiment of the present invention. Such stem cells include but are not limited to hematopoietic stem cells (HSC), stem cells of epithelial tissues such as the skin and the lining of the gut, embryonic heart muscle cells, liver stem cells (see, e.g., WO 94/08598), and neural stem cells (Stemple and Anderson, 1992, Cell 71:973–985).

Epithelial stem cells (ESCs) or keratinocytes can be obtained from tissues such as the skin and the lining of the gut by known procedures (Rheinwald, 1980, Meth. Cell Bio. 21A:229). In stratified epithelial tissue such as the skin, renewal occurs by mitosis of stem cells within the germinal layer, the layer closest to the basal lamina. Stem cells within the lining of the gut provide for a rapid renewal rate of this tissue. ESCs or keratinocytes obtained from the skin or lining of the gut of a patient or donor can be grown in tissue culture (Pittelkow and Scott, 1986, Mayo Clinic Proc. 61:771). If the ESCs are provided by a donor, a method for suppression of host versus graft reactivity (e.g., irradiation, drug or antibody administration to promote moderate immunosuppression) can also be used.

With respect to hematopoietic stem cells (HSC), any technique that provides for the isolation, propagation, and maintenance in vitro of HSC can be used in this embodiment of the invention. Techniques by which this may be accomplished include (a) the isolation and establishment of HSC cultures from bone marrow cells isolated from the future host, or a donor, or (b) the use of previously established long-term HSC cultures, which may be allogeneic or xenogeneic. Non-autologous HSC are used preferably in conjunction with a method of suppressing transplantation immune reactions of the future host/patient. In a particular embodiment of the present invention, human bone marrow cells can be obtained from the posterior iliac crest by needle aspiration (see, e.g., Kodo et al., 1984, J. Clin. Invest. 73:1377–1384). In a preferred embodiment of the present invention, the HSCs can be made highly enriched or in substantially pure form. This enrichment can be accomplished before, during, or after long-term culturing, and can be done by any techniques known in the art. Long-term cultures of bone marrow cells can be established and maintained by using, for example, modified Dexter cell culture techniques (Dexter et al., 1977, J. Cell Physiol. 91:335) or Witlock-Witte culture techniques (Witlock and Witte, 1982, Proc. Natl. Acad. Sci. USA 79:3608–3612).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

A further embodiment of the present invention relates to the therapeutic use of a purified antibody or a fragment thereof for the treatment of conditions associated with abnormalities in the APP pathway, including but not limited to, AD. It is contemplated that the purified antibody or a fragment thereof specifically binds to a polypeptide that comprises the amino acid sequence of any of the human homologs of the genetic modifiers identified in Table 1, preferably, the polypeptides of human homologs located on chromosome 10 disclosed herein, most preferably, the polypeptide encoded by SEQ ID NO: 15, SEQ ID NO: 17 or SEQ ID NO 53, i.e. the curated noc A sequences, or to a fragment of said polypeptides. A preferred embodiment relates to a fragment of such an antibody, which fragment is an Fab or F(ab')$_2$ fragment. In particular, the antibody can be a polyclonal antibody or a monoclonal antibody.

Described herein are methods for the production of antibodies capable of specifically recognizing one or more differentially expressed gene epitopes. Such antibodies may include, but are not limited to polyclonal antibodies, monoclonal antibodies (mAbs), humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above. Such antibodies may be used, for example, in the detection of a fingerprint, target, gene in a biological sample, or, alternatively, as a method for the inhibition of abnormal target gene activity. Thus, such antibodies may be utilized as part of Alzheimer's disease treatment methods, and/or may be used as part of diagnostic techniques whereby patients may be tested for abnormal levels of a modifier polypeptide, or for the presence of abnormal forms of a modifier polypeptide.

For the production of antibodies to a specific modifier polypeptide, various host animals may be immunized by injection with the polypeptide, or a portion thereof. Such host animals may include but are not limited to rabbits, mice, and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum.*

Polyclonal antibodies are heterogeneous populations of antibody molecules derived from the sera of animals immunized with an antigen, such as target gene product, or an antigenic functional derivative thereof. For the production of polyclonal antibodies, host animals such as those described above, may be immunized by injection with a modifier polypeptide, or a portion thereof, supplemented with adjuvants as also described above.

Monoclonal antibodies, which are homogeneous populations of antibodies to a particular antigen, may be obtained by any technique that provides for the production of antibody molecules by continuous cell lines in culture. These include, but are not limited to the hybridoma technique of Kohler and Milstein, (1975, Nature 256:495≧497; and U.S. Pat. No. 4,376,110), the human B-cell hybridoma technique (Kosbor et al., 1983, Immunology Today 4:72; Cole et al., 1983, Proc. Natl. Acad. Sci. USA 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable or hypervariable region derived from a murine mAb and a human immunoglobulin constant region.

Alternatively, techniques described for the production of single chain antibodies (U.S. Pat. No. 4,946,778; Bird, 1988, Science 242:423–426; Huston et al., 1988, Proc. Natl. Acad. Sci. USA 85:5879–5883; and Ward et al., 1989, Nature 334:544–546) can be adapted to produce differentially expressed gene-single chain antibodies. Single chain antibodies are formed by linking the heavy and light chain fragments of the Fv region via an amino acid bridge, resulting in a single chain polypeptide.

Most preferably, techniques useful for the production of "humanized antibodies" can be adapted to produce antibodies to the polypeptides, fragments, derivatives, and functional equivalents disclosed herein. Such techniques are disclosed in U.S. Pat. Nos. 5,932,448; 5,693,762; 5,693,761; 5,585,089; 5,530,101; 5,910,771; 5,569,825; 5,625,126; 5,633,425; 5,789,650; 5,545,580; 5,661,016; and 5,770,429, the disclosures of all of which are incorporated by reference herein in their entirety.

Antibody fragments that recognize specific epitopes may be generated by known techniques. For example, such fragments include but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al., 1989, Science, 246:1275–1281) to allow rapid and easy identification of monoclonal Fab fragments with the desired specificity.

An antibody of the present invention can be preferably used in a method for the diagnosis of a condition associated with abnormal APP pathway regulation and/or Alzheimer's Disease in a subject, or to identify a subject with a predisposition to said conditions, which comprises: measuring the amount of a polypeptide comprising the amino acid sequence of any of the human homologs of the genetic modifiers identified in Table 1, preferably, the polypeptides of human homologs located on chromosome 10 disclosed herein, most preferably, the polypeptide encoded by SEQ ID NO: 15, SEQ ID NO: 17 or SEQ ID NO 53, i.e. the curated noc A sequences, or fragments thereof, in an appropriate tissue or cell from a subject wherein the presence of an elevated amount of said polypeptide or fragments thereof, relative to the amount of said polypeptide or fragments thereof in the respective tissue from a control subject is diagnostic of said condition. Such a method forms a further embodiment of the present invention. Preferably, said detecting step comprises contacting said appropriate tissue or cell with an antibody which specifically binds to a polypeptide that comprises the amino acid sequence of any one or more of the polypeptides discussed above or a fragment thereof and detecting specific binding of said antibody with a polypeptide in said appropriate tissue or cell, wherein detection of specific binding to a polypeptide indicates the presence of any one or more of said polypeptides or a fragment thereof.

Particularly preferred, for ease of detection, is the sandwich assay, of which a number of variations exist, all of which are intended to be encompassed by the present invention.

For example, in a typical forward assay, unlabeled antibody is immobilized on a solid substrate and the sample to be tested brought into contact with the bound molecule. After a suitable period of incubation, for a period of time sufficient to allow formation of an antibody-antigen binary complex. At this point, a second antibody, labeled with a reporter molecule capable of inducing a detectable signal, is then added and incubated, allowing time sufficient for the formation of a ternary complex of antibody-antigen-labeled antibody. Any unreacted material is washed away, and the presence of the antigen is determined by observation of a signal, or may be quantitated by comparing with a control sample containing known amounts of antigen. Variations on the forward assay include the simultaneous assay, in which both sample and antibody are added simultaneously to the bound antibody, or a reverse assay in which the labeled antibody and sample to be tested are first combined, incubated and added to the unlabeled surface bound antibody. These techniques are well known to those skilled in the art, and the possibility of minor variations will be readily apparent. As used herein, "sandwich assay" is intended to encompass all variations on the basic two-site technique. For the immunoassays of the present invention, the only limiting factor is that the labeled antibody be an antibody that is specific for modifier polypeptide or a fragment thereof.

The most commonly used reporter molecules in this type of assay are either enzymes, fluorophore- or radionuclide-containing molecules. In the case of an enzyme immunoassay an enzyme is conjugated to the second antibody, usually by means of glutaraldehyde or periodate. As will be readily recognized, however, a wide variety of different ligation techniques exist, which are well-known to the skilled artisan. Commonly used enzymes include horseradish peroxidase, glucose oxidase, beta-galactosidase and alkaline phosphatase, among others. The substrates to be used with the specific enzymes are generally chosen for the production, upon hydrolysis by the corresponding enzyme, of a detectable color change. For example, p-nitrophenyl phosphate is suitable for use with alkaline phosphatase conjugates; for peroxidase conjugates, 1,2-phenylenediamine or toluidine are commonly used. It is also possible to employ fluorogenic substrates, which yield a fluorescent product rather than the chromogenic substrates noted above. A solution containing the appropriate substrate is then added to the tertiary complex. The substrate reacts with the enzyme linked to the second antibody, giving a qualitative visual signal, which may be further quantitated, usually spectrophotometrically, to give an evaluation of the amount of modifier protein which is present in the serum sample.

Alternately, fluorescent compounds, such as fluorescein and rhodamine, may be chemically coupled to antibodies without altering their binding capacity. When activated by illumination with light of a particular wavelength, the fluorochrome-labeled antibody absorbs the light energy, inducing a state of excitability in the molecule, followed by emission of the light at a characteristic longer wavelength. The emission appears as a characteristic color visually detectable with a light microscope. Immunofluorescence and EIA techniques are both very well established in the art and are particularly preferred for the present method. However, other reporter molecules, such as radioisotopes, chemiluminescent or bioluminescent molecules may also be employed. It will be readily apparent to the skilled artisan how to vary the procedure to suit the required use.

Polynucleotides encoding human homologs of genetic modifiers identified according to the methods of the present invention may be used in a method to diagnose conditions associated with defects in the regulation of the APP pathway, including but not limited to Alzheimer's Disease or to identify individuals with a genetic predisposition to such conditions. For example, said method comprises detecting the level of transcription of mRNA transcribed from the gene encoding a human homolog of a genetic modifier disclosed herein in an appropriate tissue or cell from a human, wherein abnormal transcription compared to control levels is diagnostic of said condition or a predisposition to said condition. In particular, said genetic modifier comprises the nucleotide sequence of any of the human homologs of the genetic modifiers identified in Table 1, preferably, the polypeptides of human homologs located on chromosome 10 disclosed herein, most preferably, the polypeptides encoded by SEQ ID NO: 15, SEQ ID NO: 17 or SEQ ID NO 53, i.e. the curated noc A sequences, or the polypeptide encoded by SEQ ID NO: 35, i.e. the EGR2 sequence, or the polypeptides encoded by SEQ ID NO: 41, or SEQ ID NO: 43, the ankyrin-related sequences.

Detection of a mutated form of a gene encoding a genetic modifier identified according to the methods of the present invention which is associated with a dysfunction will provide a diagnostic tool that can add to, or define, a diagnosis of a disease, or susceptibility to a disease, which results from under-expression, over-expression or altered spatial or temporal expression of the gene. Said diseases may include, but are not limited to, Alzheimer's Disease or other conditions characterized by errors in the regulation of the APP pathway. Individuals carrying mutations in said genes may be detected at the DNA level by a variety of techniques.

Nucleic acids, in particular mRNA, for diagnosis may be obtained from a subject's cells, such as from blood, urine, saliva, tissue biopsy or autopsy material. The genomic DNA may be used directly for detection or may be amplified enzymatically by using PCR or other amplification techniques prior to analysis. RNA or cDNA may also be used in similar fashion. Deletions and insertions can be detected by a change in size of the amplified product in comparison to the normal genotype. Hybridizing amplified DNA to labeled nucleotide sequences encoding the human homolog of a genetic modifier polypeptide of the present invention can identify point mutations. Perfectly matched sequences can be distinguished from mismatched duplexes by RNase digestion or by differences in melting temperatures. DNA sequence differences may also be detected by alterations in electrophoretic mobility of DNA fragments in gels, with or without denaturing agents, or by direct DNA sequencing (e.g., Myers et al., Science (1985) 230:1242). Sequence changes at specific locations may also be revealed by nuclease protection assays, such as RNase and S1 protection or the chemical cleavage method (see Cotton et al., Proc Natl Acad Sci USA (1985) 85: 4397–4401). In another embodiment, an array of oligonucleotides probes comprising nucleotide sequence encoding a genetic modifier polypeptide of the present invention or fragments of such a nucleotide sequence can be constructed to conduct efficient screening of e.g., genetic mutations. Array technology methods are well known and have general applicability and can be used to address a variety of questions in molecular genetics including gene expression, genetic linkage, and genetic variability (see for example: M. Chee et al., Science, Vol 274, pp 610–613 (1996)).

The diagnostic assays offer a process for diagnosing or determining a susceptibility to disease through detection of mutation in a human homolog of a modifier gene by the methods described. In addition, such diseases may be diagnosed by methods comprising determining from a sample derived from a subject an abnormally decreased or increased level of polypeptide or mRNA. Decreased or increased expression can be measured at the RNA level using any of the methods well known in the art for the quantitation of polynucleotides, such as, for example, nucleic acid amplification, for instance PCR, RT-PCR, RNase protection, Northern blotting and other hybridization methods. Assay techniques that can be used to determine levels of a protein, such as a polypeptide of the present invention, in a sample derived from a host are well known to those of skill in the art. Such assay methods include radioimmunoassays, competitive-binding assays, Western Blot analysis and ELISA assays.

Such hybridization conditions may be highly stringent or less highly stringent, as described above. In instances wherein the nucleic acid molecules are deoxyoligonucleotides ("oligos"), highly stringent conditions may refer, e.g., to washing in 6×SSC/0.05% sodium pyrophosphate at 37° C. (for 14-base oligos), 48° C. (for 17-base oligos), 55° C. (for 20-base oligos), and 60° C. (for 23-base oligos). Suitable ranges of such stringency conditions for nucleic acids of varying compositions are described in Krause and Aaronson (1991), Methods in Enzymology, 200:546–556 in addition to Maniatis et al., cited above.

Thus in another aspect, the present invention relates to a diagnostic kit which comprises:

(a) a polynucleotide of a human homolog of a genetic modifier identified according to the methods of the present invention, preferably, a polypeptide of a human homolog located on chromosome 10 disclosed herein, or a fragment thereof, (b) a nucleotide sequence complementary to that of (a);

(c) a polypeptide of a genetic modifier of the present invention, preferably the polypeptide of a human homolog of the genetic modifiers identified in Table 1, preferably, the polypeptide of a human homolog located on chromosome 10 disclosed herein, or a fragment thereof, or (d) an antibody to a genetic modifier polypeptide of the present invention, preferably to the polypeptide of a human homolog of the genetic modifiers identified in Table 1, preferably, the polypeptide of a human homolog located on chromosome 10 disclosed herein.

It will be appreciated that in any such kit, (a), (b), (c) or (d) may comprise a substantial component. It is also contemplated that such a kit may comprise components directed to one or more of said human homologs. Such a kit will be of use in diagnosing a disease or susceptibility to a disease, particularly to a disease or condition associated with errors in the regulation of the APP pathway including, but not limited to, Alzheimer's Disease.

The nucleotide sequences of the human homologs of genetic modifiers of the present invention can also be used for genetic linkage analysis. Since the complete human genome sequence is known, the nucleotide sequence of interest can be specifically mapped to a particular location on an individual human chromosome. The mapping of relevant sequences to chromosomes according to the present invention is an important first step in correlating those sequences with gene associated disease. Once a sequence has been mapped to a precise chromosomal location, the physical position of the sequence on the chromosome can be correlated with genetic map data. Such data are found in, for example, V. McKusick, Mendelian Inheritance in Man (available on-line through Johns Hopkins University Welch Medical Library). The relationship between genes and diseases that have been mapped to the same chromosomal region are then identified through linkage analysis (coinheritance of physically adjacent genes). Recent data indicate that there is a region on human chromosome 10 linked to Alzheimer's Disease (Bertram et a.l, Ertekin-Taner et a.l, Myers et al., *Science* 290, 2302–2305, 2000), thus, human homologs of genetic modifiers identified according to the methods of the present invention may be subjected to chromosomal mapping analysis using conventional techniques.

The invention includes an isolated nucleic acid molecule, preferably a DNA molecule, wherein the nucleic acid molecule is the curated sequences of the human nocA homolog set forth in SEQ ID NO: 15, SEQ ID NO:17 or SEQ ID NO 53. Likewise preferred is an isolated nucleic acid molecule, preferrably a DNA molecule, encoding a polypeptide comprising the amino acid sequence encoded by the sequence of EGR2, set forth in SEQ ID NO:35. Likewise preferred is an isolated nucleic acid molecule, preferably a DNA molecule, encoding a polypeptide consisting of the amino acid sequences encoded by any of the sequences of the ankyrin-repeat proteins, set forth in SEQ ID NO:41, or SEQ ID NO: 43.

Using conventional techniques, antisense molecules, double stranded RNA, triple helix DNA and ribozymes, directed to an appropriate nucleotide sequence of a genetic modifier, may be created. Modifications of gene expression can be obtained by designing antisense molecules, DNA, or RNA, to the control regions of the genes listed in Table 1, i.e. the promoters, enhancers, and introns. Oligonucleotides derived from the transcription initiation site, e.g., between positions −10 and +10 from the transcription start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules.

Recent therapeutic advances using triplex DNA have been described in the literature (Gee, J. E. et al. (1994) In: Huber, B. E. and B. I. Carr, *Molecular and Immunologic Approaches,* Futura Publishing Co., Mt. Kisco, N.Y.). The antisense molecules may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding the gene products of Table 1.

Specific ribozyme cleavage sites within any potential RNA target are initially identified by scanning the target molecule for ribozyme cleavage sites which include the following sequences: GUA, GUU and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Antisense molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding the genes of Table 1. Such DNA sequences may be incorporated into a wide variety of vectors with suitable RNA polymerase promoters such as T7 or SP6. Alternatively, these cDNA constructs that synthesize antisense RNA constitutively or inducibly can be introduced into cell lines, cells, or tissues.

Vectors may be introduced into cells or tissues by many available means, and may be used in vivo, in vitro or ex vivo. For ex vivo therapy, vectors may be introduced into stem cells taken from the patient and clonally propagated for autologous transplant back into that same patient. Delivery by transfection and by liposome injections may be achieved using methods which are well known in the art.

Gene specific inhibition of gene expression may also be achieved using conventional double stranded RNA technologies. A description of such technology may be found in WO 99/32619 which is hereby incorporated by reference in its entirety.

Still further, such molecules may be used as components of diagnostic methods and kits whereby the presence of an allele causing diseases associated with abnormalities in the APP pathway and/or Alzheimer's Disease may be detected.

Other objects, features, advantages and aspects of the present invention will become apparent to those of skill from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

EXAMPLES

The following procedures are performed to conduct the examples:

Transgenic Flies

Methods for the creation of transgenic *Drosophia melanogaster* flies are well known to one of skill in the art. Any conventional method can be employed, for example, the basic laboratory techniques that are involved in the creation of the flies of the present invention are described in Spradling, above. As contemplated herein, transgenic flies may be created by direct fusion of DNA sequences of interest with expression control sequences as described below. For example, transformed strains are generated using the constructs discussed above according to conventional methods. Several independent insertions may be obtained for the constructs, UAS-Abeta40, UAS-Abeta42, UAS-C99 wt, UAS-C99V7171(London mutation) and pGMR-Abeta42.

Fly Stocks

Gal4 lines that may be used to drive expression of the transgenes in the transgenic flies of the present invention include, but are not limited to, apterous-Gal4 and 7B-Gal4. Descriptions of the Gal4 lines mentioned and notes about their specific expression patterns can be found in Flybase (http://flybase.bio.indiana.edu). New transgenic strains generated in house include strains carrying UAS Abeta$_{40}$ and Abeta$_{42}$, UAS C99 wild type and UAS C99 London (carrying the London FAD Alzheimer's-associated mutation) and GMR Abeta$_{42}$ transgenes.

The yw; BcElp/CyOHop strain, expressing transposase, and the strains yw; Gla/SM6a and yw; Dr/TM3 Sb Ser were obtained from R. Padgett, Waksman Institute, Rutgers University. $w^{1118}$ flies and GMR-GAL4 flies were from the Bloomington stock center. The pGMR-1 strain is a publicly available stock and was obtained from G. Rubin's lab at UC Berkeley.

DNA Constructs and Molecular Techniques

A DNA fragment coding for the Aβ 42 peptide and fused to the human pre-proenkephalin signal peptide is PCR amplified and cloned into the Bgl II site of the *Drosophila* eye-specific P element transformation vector, pGMR (Hay et al., 1994 Development 120:2121–2129) and the insert is sequenced by automated fluorescence sequencing (ACGT Inc.). The human pre-proenkephalin signal peptide has been shown to successfully drive secretion of Aβ 42 from transfected mammalian cells. GMR is composed of five tandem copies of a response element derived from the rhodopsin-1 gene promoter, a binding site for the eye-specific transcription factor GLASS (Ellis et al., Development 119(3):855–65 (1993). Thus, Abeta expression is driven in the pattern of the GLASS transcriptional activator in the eye. The above DNA fragment is subsequently cloned into a P-element containing vector that facilitates the insertion of the transgene into the *Drosophia* genome. All molecular manipulations are done according to standard protocols. (See, for example, Sambrook, Fritsch and Maniatis, "Molecular Cloning A Laboratory Manual, $2^{nd}$ Edition, Cold Spring Harbor Laboratory Press, 1989).

A DNA fragment coding for the C99 peptide and fused to the human pre-proenkephalin signal peptide is PCR amplified and cloned into the pUAST transformation vector as described in Brand and Perimmon.

The constructs UAS-Abeta40, UAS-Abeta42, UAS-C99 wt and UAS-C99V7171 contain the pre-proenkephaline gene signal peptide followed by fragments of human Abeta (40 or 42) or C99 (wild type or with the London mutation). The human fragments are cloned into the pUAST vector as described in Brand and Perrimon, above. Cloning into this vector places the UAS sequence upstream of the transcribed region of the inserted gene and also allows integration into the fly genome through P-element recombination.

Genetic Crosses, Analysis and Visualization of Phenotypes

Flies are crossed according to conventional methods except that all crosses are kept at 29° C. for maximal expression of phenotypes. In the binary Gal4 expression system, this temperature maximizes activity of the Gal4 protein. In the case of pGMR-Abeta42, it is observed that the phenotype is stronger at 29° C., so these flies are kept at this temperature as well.

Western Analysis

Ectopic gene expression can be assayed by performing Western analysis according to conventional methods. Antibodies that may be used include the human 6E10 monoclonal antibody raised against the beta amyloid portion of the APP gene and which also recognizes the C99 portion of APP (Senetek PLC, Napa, Calif.).

Western Protocol

To detect expression of the Aβ 42 peptide, flies of genotypes K18.1/K18.1, K18.3/K18.3, K18.1/K18.1; K18.3/K18.3, KJ103/TM3Sb Ser, KJ103/KJ103, KJ54/CyO; KJ54/TM2 Ubx and pGMR-1 (flies carrying pGMR vector without insert) are reared at 29° C. 80–90 *Drosophia* heads from each of the above strains are collected, placed in an eppendorf tube on dry ice containing 100 μl of 2% SDS, 30% sucrose, 0.718 M Bistris, 0.318 M and Bicine, with "Complete" protease inhibitors (Boehringer Mannheim) and are ground using a mechanical homogenizer. Samples are heated for 5 min at 95° C., spun down for 5 min at 12,000 rpm, and supernatants are transferred into a fresh eppendorf tube. 5% β-mercaptoethanol and 0.01% bromphenol blue are added and samples are boiled prior to loading. Approximately 200 ng of total protein extract is loaded for each sample, on a 15% Tricine/Tris SDS PAGE gel containing 8M Urea. The Aβ 1–42 peptide control is human β-amyloid [1–42] (BIOSOURCE International, # 03-111). Samples are run at 40V in the stacking gel, and at 120V in the separating gel. Samples are transferred to PVDF membranes (BIO-RAD, # 162-0174) for 1 hr @100V, and the membranes are subsequently boiled in PBS for 3 min. Antibody hybridization is as follows: the primary Ab 6E10 (SENETECK PLC, #300-02), which recognizes the first 19 amino acids of the Aβ peptide, is used for probing (at a concentration of 1:2000) in 5% non-fat milk, 1×PBS containing 0.1% Tween 20, for 90 min @ RT. Samples are washed 3 times for 5 min., 15 min. and 15 min. each, in IX PBS-0.1% Tween-20. The secondary Ab is anti-mouse-HRP (Amersham Pharmacia Biotech, # NA 931) and is used at 1:2000 in 5% non-fat milk, 1×PBS containing 0.1% Tween 20, for 90 min at RT. Samples are washed 3 times for 5 min., 15 min. and 15 min. each, in 1×PBS-0.1% Tween-20. ECL (ECL Western Blotting Detection Reagents, Amersham Pharmacia Biotech, # RPN 2209) is used for detection.

Histology

Plastic sections of fly heads are performed according to conventional methods, for example, as according to the protocols described in: *Drosophia* Protocols, page 236. Eds. W. Sullivan, M. Ashburner, S. Hawley, CSHL Press 2000

Cryosections

Adult eyes are cryosectioned according to Wolff, in *Drosophia Protocols*, CSHL Press, 2000, sections 13.1 and 13.2. The primary antibody is the monoclonal 6E10 (Senetek), recognizing the human Aβ 42 peptide, used at a dilution of 1:3000. The detection system is the Vectastain ABC Kit (with biotinylated anti-mouse IgG secondary, and Horseradish peroxidase H) (Vector Laboratories). The following modifications are made to the protocol by Wolff: prior to incubation with the 6E10 primary antibody, cryosections are blocked in blocking solution containing normal horse serum, according to the Vectastain ABC Kit protocol. Incubation with the secondary (preadsorbed with pGMR-1 eye tissue) is done in PBS/1% BSA containing 1–2% normal horse serum, also according to the Vectastain ABC Kit protocol. The procedure for the ABC Kit is followed; incubations with the ABC reagent are done in PBS/0.1% saponin, followed by 4×10 min. washes in PBS/0.1% saponin. Sections are then incubated in 0.5 ml per slide of the Horseradish Peroxidase H substrate solution, 400 ug/ml 3,3'-diaminobenzidene (DAB), 0.006% $H_2O_2$ in PBS/0.1% saponin, and the reaction is stopped after 3 min. with 0.02% sodium azide in PBS. Sections are rinsed several times in PBS and dehydrated through an ethanol series before mounting in DPX (Fluka).

RNA Profile Characterization for Compound Screening

RNA profiles may be assayed according to known methodology, including use of traditional Northern blot analysis as well as microarray chip technology (Incyte Pharmaceuticals, Palo Alto, Calif.; Affymetrix, Santa Clara, Calif.).

Example 1

The Rough Eye Phenotype Induced by Ectopic Expression of Aβ 42

In order to elucidate the largely unknown pathways and mechanism(s) by which Aβ 42 causes neurodegeneration, the *Drosophia* eye, a neural tissue, is used as a model. In an effort to mimic the disease-specific Aβ 42 overexpression, transgenic flies whose genome comprises the GMR-Abeta42 amyloid transgene are created using the GMR fusion expression system disclosed above in order to ectopically express the transgene in the developing *Drosophia* eye.

I. Aβ 42 Overexpression Causes Rough Eye Phenotypes

In order to express the Aβ 42 peptide in the *Drosophia* eye, the Aβ 42 sequence is cloned into the pGMR vector. The pGMR (Glass Multimer Reporter) vector contains a pentamer of truncated binding sites for the Glass transcription factor. Glass is expressed widely during eye development, starting in the eye discs, the precursors of adult *Drosophila* eyes, where it is detected in differentiating photoreceptor neurons. It continues being expressed specifically in the eye during pupal and adult development (Moses et al, 1989 Nature 340 (6234):531–536; Moses and Rubin, 1991 Genes Dev. 5:583–593). GMR-element expression in ~2 week-old flies is examined using a reporter gene and good expression detected, suggesting that GMR element is active well into adulthood. Thus, GMR-regulated expression is directed to the eye tissue throughout the development of the eye, as well as during adulthood, making it a suitable system for expression of Aβ 42.

Two independent transgenic lines are originally established with the pGMR-Aβ 42 construct, K18.1 and K18.3. In addition, another transgenic line, pGMR-1, expressing the same vector without an insert, is examined as a negative control. Control flies with the pGMR-1 transgene and flies carrying one copy of either the K18.3 or the K18.1 transgene do not show a rough eye. Similarly, flies carrying one copy each of both of the above transgenes (K18.3 and K18.1) or two copies of the K18.1 transgene also have wild type eyes. In contrast, flies with two copies of K18.3 have a mild rough eye phenotype; examination of fly eyes under light microscopy indicate that ectopic overexpression of Aβ 42 disrupts the regular trapezoidal arrangement of the photoreceptor cells of the ommatidia (identical single units, forming the *Drosophia* compound eye. The above observations suggest that there might be a dose response of the rough eye phenotype to the copy number of transgenes present in the fly genome. To further examine this hypothesis, the number of transgenes is increased to three (2 copies of K18.1 with one copy of K18.3 or one copy of K18.1 with two copies of K18.3). These strains also showed rough eyes. Finally, when four copies of the transgene were present (2 copies of K18.1 with 2 copies of K18.3), flies showed a much more severe rough eye phenotype confirming the dose response hypothesis. The penetrance of the rough eye phenotypes is 100% in all genetic combinations. It must also be noted that a more severe phenotype is observed when flies are reared at 29° C. A temperature requirement for expressivity of eye phenotypes has been described previously (Karim and Rubin, 1998 Development 125(1):1–9) and may be specific for the eye, even though it is not restricted to GMR-containing expression systems. Such dependence could be attributed to higher transcriptional and/or metabolic rates, or altered protein conformation at the higher temperature.

II. Aβ 42 transgenics display rough eye phenotypes, the severity of which depends on transgene copy number.

It is well established that the expression level of transgenes in *Drosophila* depends on the chromosomal location of the specific insertions, a phenomenon known as "position effect" (Kellum, R. and Schedl, P. (1991). *Cell*. 64: 941–50). It is possible then, by generating additional independent insertions with the same transgene, to recover transgenic lines that express different levels of the transgenic protein. Thus, it might be possible to isolate transgenic lines that would express the Aβ 42 transgene at a high enough level to cause a phenotype at a lower temperature (25° C.), thus reflecting more physiological conditions. To test this hypothesis, new insertions of the pGMR-Aβ 42 transgene in the fly genome are generated, using "P-element hopping" (Robertson, H. M. et al. (1988). *Genetics* 118: 461–470).

A total of 19 independent lines of the pGMR-Aβ 42 construct in new chromosomal locations are established. The new strains are judged as carrying new insertions based on the chromosomal linkage or homozygous lethal condition of the transgene, as well as by differences in eye color (caused by differential expression levels of the white gene, used as a transformation marker). Young larvae of the above new strains are subsequently raised at 29° C. until eclosion and examined for the presence of an eye phenotype. Of the 19 new lines, 7 lines, or 38%, show a rough eye phenotype. The strains that display a rough eye phenotype are subsequently raised at 25° C. and scored for an eye phenotype.

The new transgenic lines show varying degrees of phenotypic severity, some of them displaying a more severe phenotype than what was originally observed in the K18.1 and K18.3 line. One such example is the KJ.103 line, in which one copy of the transgene renders the adult eyes mildly rough, characterized by the presence of interspersed darker "spots" (corresponding to deeper-red pigmented ommatidia) on the ventral side of the eye, while two copies of the transgene cause extensive disorganization of photoreceptors. More importantly, this specific line displays the rough eye phenotype even when the flies are raised at 25° C. When KJ.103 flies are raised at 29° C., the severity of phenotype caused by either one or two copies of the transgene is increased dramatically.

In summary, rough eye phenotypes caused by the Aβ 42 peptide show a range of severity. The very mild lines typically display numerous dark/black "spots" on the ventral side of the eye, while mild lines have a more rough, disorganized appearance covering the ventral portion of the eye. Moderate lines show greater roughness over the entire eye, while in more severe lines the entire eye seems to have lost/fused many of the ommatidia and interommatidial bristles, and the entire eye has a smooth, glossy appearance. Interestingly, the size of the eye is only moderately affected in flies with the highest level of the Aβ 42 expression (strain KJ54). This is consistent with observations in flies expressing human α-synuclein (Feany, M. B. and Bender, W. W. (2000) Nature 404:394–398. In flies expressing polyglutamine expanded human huntingtin, a very slight reduction of eye size is observed, in the strongest-expressing transgenic lines (Warrick, J. M., et al (1998). *Cell* 93: 939–949). The above results suggest that neurodegeneration induced by over-expression of human disease genes differs from the phenotypes caused by overexpression of genes acting in apoptotic pathways (Grether, M. E. et al. (1995). *Genes Dev.* 9, 1694–1708), in which the size of the eye is primarily affected.

Based on the above results, it is hypothesized that the severity of the rough eye phenotype depends on the amount of Abeta protein present. As a consequence of this hypothesis, it should be expected that the KJ.103 transgene displays a higher level of protein expression than the K18.3 transgene (see below).

III. Expressivity of the Rough Eye Phenotype Correlates with Aβ42 Protein Levels To determine if the severity of the rough eye phenotype correlates with expression levels of the Aβ 42 peptide, Western blot analysis of protein extracts from *Drosophila* heads are performed (strains used are described in methods above). Results indicate that animals with two copies of the transgene have roughly twice the amount of Aβ 42 peptide than animals with one transgene copy. Interestingly, even though flies with two copies of K18.1 express the Aβ 42 peptide in detectable quantities, they have no visible adult eye phenotype. Flies with two copies of the higher-expressing K18.3 transgene, expressing overall larger quantities of Aβ 42 peptide do show the rough eye phenotype. This is also true for flies expressing two copies of the K18.1 and two copies of the K18.3 transgenes. Flies expressing only one copy of the KJ103 transgene have roughly equal amounts of protein as flies expressing two copies of the K18.3 transgene, confirming the hypothesis that the KJ103 transgene shows higher levels of relative protein expression.

The above results indicate that there is a requirement for a certain level of Aβ42 protein in order to generate a visible phenotype. It is still possible that lower amounts of Aβ 42 expression cause minor disruptions that would only be visible at the ultrastructural level. To test this, thin sections (1.5 μm) from adult fly heads are examined. These data indicate that, compared to eyes from a fly carrying the empty pGMR vector, in which the tolouidine-blue staining photoreceptors are regularly arrayed, flies carrying one copy of the moderately expressing K18.3 transgene have small abnormalities—some photoreceptors are missing, blue-staining masses are forming around the ommatidia and some gaps are appearing in the tissue. These eyes appear normal macroscopically.

Sections from eyes expressing two copies of the K18.3 transgene, in agreement with observations at the macroscopic level, display variable disorganization. As the phenotype gets worse, the concentration of dense, staining masses around the ommatidia increases, as do the gaps in the tissue. The ommatidia look smaller and are missing photoreceptors. Two copies of the higher expressing KJ103 transgene show a phenotype similar in severity. Finally, eyes from *Drosophia* expressing four copies of the strong expressing KJ54 transgene show an almost complete loss of photoreceptors. Additionally, these eyes show an abundance of dense, staining masses and of tissue gaps. Even though it is not clear at this point whether the dense, staining masses that surround the ommatidia are abnormal/dying cells or whether they contain aggregating Abeta peptide, it is clear that their accumulation is coincident with observed overall eye degeneration.

In order to visualize the expression of beta-amyloid on the eye tissue, sections of Aβ expressing eyes are stained with an antibody recognizing the human Aβ peptide. Transverse sections of eye tissue show a punctate staining that is absent in controls. It is hypothesized that this punctate staining corresponds to small aggregates/deposits of beta amyloid. Cellular localization of this staining as well as the exact nature of the aggregate/deposit, using known Aβ staining dyes is under investigation.

In summary, it is disclosed herein that introduction of more copies of the Aβ 42 transgene in the *Drosophia* eye, reflected by increased levels of Aβ protein, has an additive affect on the rough eye phenotype. It is possible that a certain concentration of the Aβ 42 peptide is needed to affect its aggregation/conformation state. Alternatively, saturating levels of the peptide might be needed for manifestation of the toxic effect. The fact that Aβ exerts neurotoxic effects in several signaling pathways, (intracellular calcium levels, oxidative stress, inflammatory response, muscarinic and nicotinic receptor signaling, reviewed in Fraser, S. P., et al (1997). *Trends Neurosci.* 20: 67–72; Mattson, M. P. (1997). *Physiol. Rev.* 77: 1081–1132; and Coughlan, C. M. and Breen, K. C. (2000). *Pharmacol. and Ther.* 86: 111–144; Hellström-Lindahl and Court, 2000 Behav Brain Res. 113 (1–2):159–168), might indicate the need for saturating levels in order to cause disruptions. It is clear however, that expressing moderate amounts of the peptide seem to have no consequence for the structure of the adult eye at the gross morphological level.

IV. Rough Eye Phenotype Induced by Aβ 42 Peptide Worsens with Age

It is well established that in Alzheimer's patients, chronic accumulation of Aβ peptide leads to initial manifestation of the disease and to progressive worsening of the symptoms. In order to test whether one could mimic this aspect of the disease in the *Drosophila* model, the degree of roughness of the eye phenotype in aged flies is recorded.

Two strains of flies, expressing pGMR1 (as a negative control) and K18.3 are examined. K18.3 flies are used because in this transgenic strain there is a range of phenotypic severity and thus it is easier to record changes. Flies from the two strains are raised at 25° C. and 0–2days after eclosion they are transferred to 29° C., to induce higher expression of the transgene. Flies are scored for eye phenotype approximately every week, for a total of one month, thereafter. The K18.3 flies are classified into three different groups (moderate, mild, intermediate), according to the observed severity of the eye phenotype. As mentioned previously, pGMR1 expressing flies did not show any eye phenotype.

Data indicates a shift in the phenotypic severity of the Abeta expressing flies as they age: when flies first eclose, no eyes with an intermediate phenotype are observed, whereas 15% of the population at seven days has an intermediate phenotype. Also by seven days, all of the progeny show a degree of rough eye phenotype, whereas 42% do not show any phenotype upon eclosion. By 32 days, even though a large number of flies have died, the overall ratio of flies with mild versus intermediate phenotype is not significantly changed, suggesting that the maximum effect of Abeta expression has been reached.

The *Drosophia* model disclosed herein appears to be mimicking the progressive and age-associated worsening of the Alzheimer's disease symptoms, an important aspect of the disease. The observed increase in the severity of the eye phenotype as flies age could be attributed to increased sensitivity of neuronal cells to the levels of Aβ peptide. Indeed, as mentioned above, AP peptide is being produced throughout the adult stage of *Drosophila*. It is thus possible that increased levels of Aβ cannot be effectively turned over, resulting in accumulation of the peptide in the *Drosophia* cells. Alternatively, it is possible that aged cells are more vulnerable to the presence of Aβ peptide.

V. The Rough Eye Phenotype and the Degree of Apoptotic Cells in Larval Eye Imaginal Discs and Adult Eyes As mentioned earlier, the Aβ 42 peptide has known toxic effects and it is suggested that it plays a role in apoptosis. Based on this, third instar larval eye imaginal discs, the precursors of the adult eye, are examined for evidence of apoptosis, or programmed cell death. Dissected eye imaginal discs from K18.1/K18.1; K18.3/K18.3 larvae, raised at 29° C., are stained with acridine orange according to conventional methods, which causes fluorescence of apoptotic cells. As controls, the following strains, none of which shows any eye abnormalities, are used: $w^{1118}$ (a wild-type control) and pGMR-1 (carrying the "empty" pGMR vector) grown at 29° C. and GMR-GAL4 (expressing Gal4 under the control of the GMR element), raised at 18° C.

Results indicate that little or no cell death is seen in the wild-type control, $w^{1118}$. In contrast, some amount of cell death can be detected in the K18.1/K18.1; K18.3/K18.3 line. When the controls that carry the pGMR vector but do not display any eye phenotype pGMR-1 and GMR-GAL4), are examined, some cell death is also observed, comparable in extent to that observed in the experimental flies, K18.1/K18.1; K18.3/K18.3. Therefore, it seems likely that a certain amount of cell death is tolerated during eye development and does not cause any adult eye defects, at least at the gross morphological level. In addition, it is suggested herein that if apoptosis has any involvement in the generation of the rough eye phenotype, it is not manifested during the early development of the eye.

To test whether the observed rough eye phenotype is caused by apoptosis during the adult stages of Drosophila, the apoptosis inhibitor DIAP1 is co-expressed in the *Drosophila* eye. Co-expression of DIAP1 in eyes expressing Abeta would be expected to suppress, at least partially, the rough eye phenotype (data not shown). Since no suppression with two different DIAP-expressing strains is observed, it may be that the observed rough eye phenotype is not caused by ectopically induced apoptotic cell death. The same results were obtained when the antiapoptotic baculoviral P35 gene was used. These results suggest that the effects caused by the Aβ 42 peptide in the *Drosophia* eye might be mediated by cellular pathways that do not result in apoptosis.

The actions of Aβ 42 are quite complex and could affect other proteins known to be factors in AD development. It has been shown that PS1 and PS 2 co-immunoprecipitate with APP (Xia et al., 1997 PNAS USA 94 (15):8208–13) and that Aβ 42 can directly bind PS 2 in vitro (Czech et al., 1999 Society for Neuroscience 25:641.1). It is interesting to note that overexpression of wild type and mutant PS forms also results in enhanced susceptibility to apoptosis in several experimental systems, including the *Drosophila* eye (Ye, Y. and Fortini, M. (1999). *J. Cell Biol.* 146: 1351–1364). In these studies, it is suggested that *Drosophia presenilin* (Dps) exerts a dominant negative effect when expressed at high levels. It is unclear how Dps causes apoptosis of cells, but the mechanism could involve the dysregulation of the Notch and/or Wnt developmental signaling pathways (reviewed in Anderton et al., 2000 Mol. Med. Today 6:54–59). It is unclear whether Aβ 42 overexpression in the system disclosed herein could be affecting Dps function by possibly interfering with one or more of these signaling pathways. Interestingly, overexpression of Aβ 40 or Aβ 42 enhances a Dps (*Drosophila presenilin*) induced phenotype in the same tissue (data not shown), suggesting involvement of the two proteins in the same pathway.

Example 2

Concave Wing Phenotype Induced by Ectopic Expression of C99

Transgenic *Drosophia* that carry a copy of pUAS—C99 (either wild type or with the London mutation) and a copy of apterous-Gal4 are created using standard methods and as discussed above. Data indicate that these flies exhibit a malformation of their wings in that the wing blade is curved in a concave manner. These effects are confirmed with multiple independent insertions of the C99 transgene. Western analysis confirms expression of this transgene. Protein extracts from whole larvae expressing the C99 (either wild type or with the London mutation) under the control of daughterless-Gal4 (a ubiquitously expressed Gal4 driver) show a protein band of the expected size for C99, which immunoreacts with the 6E10 antibody (raised against the first 16 amino-acids of C99). Data exists that when the portion of the human APP gene referred to as C100 was inserted into the genome of *Drosophia* and expressed in the wing disc, it did not generate any visible phenotype (Fossgfreen et al., PNAS 95:13703–13708 (1998)). In contrast, data reported herein indicate that flies transgenic with the equivalent C100 region of human APP (called here C99), fused to a different signal peptide, display a wing malformation.

Example 3

Cognitive Defects Induced by Ectopic Expression of C99

Transgenic *Drosophia* that carry a copy of UAS—C99 (either wild type or with the London mutation) and a copy of 7B-Gal4 (which allows expression in the mushroom body of the brain) are created using standard techniques. Cognitive defects of these flies can be examined by conducting olfactory, locomotion or learning and memory assays according to conventional methods. For example, altered locomotory behavior is observed in the above flies, tested using the "dark reactivity" set-up, described by Benzer, S. *PNAS* 58:1112–1119 (1967). Specifically, flies containing a copy of UAS—C99 and a copy of 7B-Gal4 do not respond to mechanical agitation as well as wild type flies, walking less quickly than wild type flies after being tapped to the bottom of the assay apparatus. The "dark reactivity" test for locomotion is also described in "Behaviour, Learning and Memory" In: *Drosophila*, A Practical Approach. Ed. D. B. Roberts (1998) Oxford University Press Inc. New York page 273.

Example 4

Genes that Modify *Drosophila* Phenotypes as Targets for Alzheimer Disease Therapeutics As disclosed in detail below, genetic screens were set up in order to identify genetic modifiers of the concave wing phenotype described in Example 2. Candidate modifiers tested included known modifiers of two *Drosophia* phenotypes induced by ectopic expression of *Drosophia presenilin* (Dps) in the wing and scutellum (G. Boulianne, Hospital for Sick Children, Toronto, Canada, personal communication), as well as mutations in other candidate genes. Based on the recent discovery of a chromosome 10 AD gene "hot spot", chromosomal mapping of the human homologs of the above mentioned *Drosophia* genetic modifiers was performed. Data disclosed below indicate that the human homologs of several of the genetic modifiers disclosed herein are also located on chromosome 10 and it is contemplated herein that these genes are relevant targets for the development of pharmaceuticals useful for the treatment of Alzheimer's Disease as well as other conditions associated with errors in the regulation of the APP pathway.

A total of 93 mutations were screened in order to identify genetic modifiers of the concave wing phenotype induced by ectopic expression of C99 in the wing of *Drosophila*. The screen is based on measuring the change in the penetrance of the wing phenotype when the external mutation is present. More specifically, the number of flies with mutant wings compared to the number of flies with wild type wings are counted in the experimental group (flies expressing both C99 and mutation being tested) and the control group (flies expressing only C99). The significance of the change in penetrance of the mutant phenotype is evaluated by measuring the P value by a T test, in the above mentioned four groups. Mutations were considered to significantly modify the C99 phenotype when P<0.05.

A list of genetic modifiers that affect the C99-overexpression phenotype and the *Drosophila* genes associated with these genetic modifiers are provided in Table 1.

All of the mutations identified as modifiers of presenilin and C99 overexpression phenotypes were insertional mutations (mediated by insertion into the *Drosophila* genome of the P-retroviral like transposable element). The exact chromosomal location of each of these insertions has been previously determined (*Drosophila* Genome Project BDGP, http://www.fruitfly.org). In order to identify the transcript(s) affected by each of these insertions, we scanned a 10 kB genomic area to the right and to the left of each insertion for known or predicted *Drosophia* transcripts. The following criteria were adopted for selection of the most likely transcript affected by a given insertion:

a) distance of transcripts from the site of insertion, and b) orientation of a transcript relative to the insertion.

If a genomic area contained more than one candidate transcripts with the same orientation as the insertion, all those closest to the insertion were selected for further analysis. The translated protein sequences of the *Drosophia* transcripts from the above analysis form "Set A".

The presence of human homologs of the above *Drosophia* proteins (in "Set A") in an AD-linked area of human chromosome 10 was examined. Two candidate regions around Sequence Tagged Site (STS) markers on human chromosome 10 have been identified (Bertram et al., Ertekin-Taner et al., Myers et al., *Science* 290, 2302–2305, 2000) by linkage analysis. We mapped STS marker sequences used in these linkage analysis studies or STS sequences adjacent to these markers to the Celera genome data by blastn (Altschul et al., 1997) sequence comparisons. Based on this mapping information a subset of human chromosome 10 was defined that included the two candidate regions showing significant linkage (Bertram et al., 2000; Ertekin-Taner et al., 2000; Myers et al., 2000) and the region in between. The DNA sequence (Celera contigs) and the corresponding list of Celera protein translations were retrieved for the subset defined and put into blast format databases. The DNA sequence and the list of Celera protein translations for the above described genomic regions form "Set B" and "Set C", respectively.

A tblastn search with "Set A" against "Set B" and a blastp search with "Set A" against "Set C" were then performed. Initially tblastn and blastp hits with E-values lower than $10^{-5}$ were selected. Then the best match of each fly protein from these searches was chosen and the corresponding fly genes/transcripts were checked for their association with genetic modifiers of the Dps and C99 phenotype. The resulting fourteen pairs of fly and human transcripts/proteins form "Set D".

The fourteen protein pairs in "Set D" were tested for stringent or putative orthology. This was accomplished by blastp comparisons to a combined database of all human and all fly Celera proteins. First, the fly proteins in "Set D" were compared to each protein in this database. Then the resulting best human matches for each of the fly proteins were again compared to the combined human/fly protein database. A human match was classified as a stringent ortholog if all of the following four criteria were fulfilled:

1. fly protein X has best match with human protein Y
2. fly protein X does not have a better match with another fly protein than with human protein Y
3. human protein Y has best match with fly protein X
4. human protein Y has no better match with another human protein than with fly protein X If only criteria 1) and 3) are fulfilled, a human match is classified as a putative ortholog regardless of whether fly protein X had a better match with another fly protein, human protein Y had a better match with another human protein or both. All other human matches are deemed homologs. After the orthology test, candidate human genes are prioritized according to the following:

a) human gene is homolog of fly gene affected by *Drosophia* genetic modifier, identified in genetic screen b) degree of sequence similarity of the human protein (encoded by the human gene in a) to the *Drosophia* protein (encoded by the *Drosophia* gene in a)
c) human protein is stringent or putative ortholog of fly protein
d) chromosomal location of the human gene with respect to STS markers, other candidate genes or known AD genes
e) putative function of the human protein and/or the homologous *Drosophia* protein
f) evidence that the predicted human gene is expressed
g) existence of validated or predicted coding and/or non-coding SNPs in the coding region of the human gene.

To check whether the human homolog gene is expressed, the Incyte LifeSeq EST database was searched with the corresponding predicted human transcripts identified from the Celera database using blastn.

Based on these criteria, it is contemplated herein that 4 different human genes are AD related genes located on human chromosome 10. Below are listed the putative proteins, encoded by these proposed human genes.
(1) hCP50765 (EGR2) SEQ ID NO: 35
(2) hCP41313 (homologous to the fly gene nocA) SEQ ID: 15, SEQ ID NO: 17 or SEQ ID NO 53
(3) hCP33787 (ankyrin-related protein) SEQ ID NO: 41
(4) hCP51594 (ankyrin-3) SEQ ID NO: 43

The Celera predicted transcript hCT15097 was manually curated to produce two putative forms of the protein hCP41313. Curation was performed by identifying ESTs corresponding to this locus by blastn searches of the Incyte LifeSeq and public EST databases and aligning the identified ESTs with the Celera predicted transcript sequence. The curation produced slight changes in the C-terminal amino-acid sequence and putative additional residues at the N-terminus of the predicted amino-acid sequence. The changes in the C-terminal part of the human protein sequence lead to an improved alignment with the fly nocA in this region. Because of the additional residues at the N-terminus Met 64 and Met 100 in the Celera protein sequence (hCP41313) correspond to Met 114 and Met 150 in the translation of the complete curated nocA a homolog transcript sequence respectively. We have subsequently analyzed and compared cDNA sequences from the Novartis FGA cDNA collection and the Incyte cDNA collection. Based on these analyses we have cloned and sequenced a cDNA clone corresponding to the human nocA gene on chromosome 10. The 5' end of this cDNA clone consists of cDNA obtained from proprietary Novaitis clone fga94341 and the 3' end of this clone consists of cDNA obtained from Incyte clone 242278.1 (SEQ ID NO: 52, SEQ ID NO. 53).

EGR2 is a putative ortholog of Celera predicted fly transcript CT23724 (see Table 1), which corresponds to the *Drosophia* stripe gene. The fly mutation P1505 (see Table 1), which affects the stripe gene, modifies only the presenilin phenotype.

Human nocA is a putative ortholog of Celera predicted fly transcript CT14619 (see Table 1), which corresponds to the *Drosophia* nocA gene. The fly mutation EP2173 (see Table 1), which affects the nocA gene, modifies both the presenilin and C99 overexpression phenotypes.

EGR2 is a C2H2 type zinc finger transcription factor regulating PNS myelination. In mice it has been shown to be important for hindbrain development (Schneider-Maunoury et al., *Cell* 75, 1199–1214, 1993; Swiatek & Gridley, *Genes Dev.* 7, 2071–2084, 1993). Four mutations in EGR2 have been described to be associated with inherited peripheral neuropathies (Warner et al., *Nature Genet* 18, 382–384, 1998; Timmerman et al., *Neurology* 52, 1827–1832, 1999).

The nocA human homologue is a putative transcription factor with a C2H2 type zinc finger domain. While its exact function has yet to be determined, according to data disclosed herein, it may play a significant role in the pathology of Alzheimer's Disease. The *Drosophia* protein encoded by the nocA gene is a transcription factor involved in the development of the embryonic brain and the adult ocellar structures.

Ankyrin-3 exists in two brain specific isoforms of 480 and 270 kDa (Kordeli et al., *J Biol Chem* 270, 2352–2359, 1995). Neural-specific Ankyrin-3 polypeptides are candidates to participate in the maintenance and targeting of ion channels and cell adhesion molecules to nodes of Ranvier and axonal initial segments. Ankyrin-3 has been shown to associate with the voltage dependent sodium channel in vitro and to co-localize with this molecule at nodes of Ranvier, axonal initial segments, and the neuromuscular junction (Srinivasan et al., *Nature* 333, 177–180, 1988; Kordeli et al., *J Cell Biol* 110, 1341–1352, 1990; Kordeli & Bennett, *J Cell Biol* 114, 1243–1259, 1991; Flucher & Daniles, *Neuron* 3, 163–175, 1989).

The second human homologue of fly transcript CT18415 belongs to the family of ankyrin-related proteins (hCP33787). The corresponding gene is located 469 kbp from insulin-degrading enzyme (IDE). In addition to ankyrin-repeats, hCP33787 contains a sterile alpha motif (SAM) domain. The SAM domain has been suggested to be involved in the regulation of developmental processes (Shultz et al., *Protein Sci* 6, 249–253, 1997), has been described as mediating specific protein-protein interactions, and has been suggested to form extended polymeric structures (Thanos et al., *Science* 283, 833–836). The SAM domain is included in the alignment between fly transcript CT18415 and hCP33787. We speculate that it might play a role in the aggregation of β-amyloid.

It has been hypothesized that γ-synuclein might be involved in AD (Luedecking et al., *Neuroscience Letters* 261, 186–188, 1999). We postulate that γ-synuclein might interact with the ankyrin repeat-containing protein hCP33787. In support of this, a protein-protein interaction between synphilin, an ankyrin repeat-related protein, and α-synuclein has been shown (Engelender et al., *Nature Gen* 22, 110–114, 1999). It is also known that members of the synuclein family share a high degree of sequence similarity (64% sequence identity between α-synuclein and γ-synuclein, Lavedan, *Genome Res* 8, 871–880, 1998). Since the fold of an ankyrin-repeat unit is conserved, the above arguments add support to a putative protein-protein interaction between hCP33783 or hCP51594 and γ-synuclein. It is of interest to note that a coding SNP (E→K) is predicted for hCP33787 at sequence position 48, which corresponds to the start of the ankyrin-repeat region. This sequence variation could be relevant in the context of a putative γ-synuclein-ankyrin interaction because it involves oppositely charged amino acid side chains. The predicted SNP in the ankyrin-related protein is particularly interesting as γ-synuclein has a validated coding SNP (V→E) at position 110 (Ninkina et al., *Hum Mol Genet* 7, 1417–1424, 1998), that codes for the exchange of a neutral by a negatively charged amino acid side chain. We postulate that these polymorphisms might be relevant to a putative interaction of γ-synuclein with either hCP33783 or hCP51594.

TABLE 1

| modifier | flyCT | Start | End | hCG | hCT | hCP | Start | End | E-value | gene name/protein family | comments | SEQ ID NO (hCT/hCP) |
|---|---|---|---|---|---|---|---|---|---|---|---|---|
| EP(2)2107 | CT25384 | 94 | 183 | hCG37225 | hCT28457 | hCP47994 | 96 | 185 | 4.00E-32 | TG-interacting factor/TALE/KNOX homeobox protein | modifier of Dps and C99 | 6/7 |
| EP(2)2122 | CT11970 | 54 | 411 | hCG22190 | hCT13283 | hCP39677 | 12 | 348 | 4.00E-75 | n/a | modifier of Dps and C99 | 8/9 |
| EP(2)2151 | CT3996 | 27 | 392 | hCG22926 | hCT14025 | hCP40373 | 39 | 415 | 1.00E-109 | NAP1/aspartyl protease-related | modifier of C99 | 10/11 |
| EP(2)2162 | CT7676 | 15 | 374 | hCG30594 | hCT21765 | hCP44907 | 13 | 373 | 3.00E-97 | n/a | modifier of Dps and C99, lethal over C99 | 12/13 |
| EP(2)2173 | CT14619 | 10 | 531 | hCG23983 | hCT15097 | hCP41313 | 100 | 564 | 1.00E-25 | Drosophila nocA Zn finger transcription factor ortholog | modifier of Dps and C99, human ortholog on 10q | 14/15, 16/17, 52/53 |
| EP(2)2205 | CT9828 | 93 | 619 | hCG41821 | hCT33094 | hCP51674 | 668 | 1180 | 4.00E-66 | angiotensin I converting enzyme (peptidyl-dipeptidase A) 1 (ACE) | modifier of Dps and C99, metalloprotease | 18/19 |
| EP(2)2511 | CT11457 | 6 | 258 | hCG20663 | hCT11743 | hCP38288 | 28 | 2.76E+02 | 2.00E-65 | copper chaperone for superoxide dismutase/ superoxide dismutase [CU—ZN] | modifier of Dps and C99 | 20/21 |
| EP(2)2554 | CT10410 | 6 | 192 | hCG39955 | hCT31207 | hCP49745 | 5 | 198 | 2.00E-16 | glutathione S-transferase theta 1 | modifier of Dps and C99 | 22/23 |
| EP(2)2554 | CT10310 | 15 | 661 | hCG40293 | hCT31548 | hCP50060 | 18 | 617 | 2.00E-90 | intersectin-related | modifier of Dps and C99 | 24/25 |
| EP(3)3041 | CT5336 | 14 | 227 | hCG42003 | hCT33279 | hCP51813 | 29 | 246 | 1.00E-39 | HSA011916 | modifier of Dps and C99 | 26/27 |
| EP(X)1526 | CT10709 | 7 | 597 | hCG37950 | hCT29186 | hCP47880 | 6 | 519 | 1.00E-168 | protein kinase inhibitor P58-related | modifier of Dps and C99 | 28/29 |
| P1396 = l(2)05206 | CT13013 | 316 | 655 | hCG20435 | hCT11514 | hCP38090 | 106 | 404 | 2.00E-72 | cyclin | modifier of Dps and C99 | 30/31 |
| P1486 = l(3)00090 | CT22943 | 1818 | 2491 | hCG32338 | hCT23526 | hCP46544 | 663 | 1248 | 2.00E-84 | retinoblastoma binding protein-related | modifier of Dps and C99 | 32/33 |
| P1505 = l(3)00643 | CT23724 | 760 | 1123 | hCG40234 | hCT31488 | hCP50765 | 131 | 439 | 3.00E-63 | early growth response 2 (Krox-20 (Drosophila) homolog) | modifier of Dps, human ortholog on 10q | 34/35 |
| P1548 = l(3)01814 | CT24038 | 75 | 167 | hCG18539 | hCT9598 | hCP36359 | 1 | 93 | 1.00E-31 | n/a | modifier of Dps and C99 | 36/37 |
| P2093 = l(3)j5C8 | CT18339 | 218 | 438 | hCG14845 | hCT5866 | hCP35211 | 38 | 278 | 6.00E-31 | baculoviral IAP repeat-containing 4/ apoptosis inhibitor related | modifier of Dps and C99 | 38/39 |
| P2093 = l(3)j5C8 | CT18415 | 62 | 293 | hCG17907 | hCT8961 | hCP33787 | 353 | 569 | 2.00E-18 | ankyrin-related | modifier of Dps, human homolog on 10q | 40/41 |
| P2093 = l(3)j5C8 | CT18415 | 50 | 349 | hCG41783 | hCT33056 | hCP51594 | 7 | 307 | 2.00E-23 | ankyrin-3, ankyrin-G | modifier of Dps, human homolog on 10q | 42/43 |
| P2104 = l(3)13B3 | CT13750 | 372 | 733 | hCG201263 | hCT201265 | hCP201588 | 61 | 432 | 1.00E-111 | ubiquitin carboxyl-terminal hydrolase | modifier of Dps and C99 | 44/45 |
| P2121 = l(3)j4E1 | CT23760 | 87 | 283 | hCG25031 | hCT16153 | hCP41935 | 239 | 437 | 2.00E-37 | dual specificity protein phosphatase | modifier of Dps and C99 | 46/47 |
| P2122 = l(3)rL074 | CT23073 | 5 | 879 | hCG39269 | hCT30519 | hCP50592 | 21 | 902 | 0 | minichromosome maintenance deficient (S. cerevisiae) 2 (mitotin)/DNA replication licensing factor MCM | modifier of Dps and C99 | 48/49 |
| P2319 = l(2)06694 | CT13966 | 1 | 932 | hCG21123 | hCT12209 | hCP38695 | 18 | 937 | 0 | alpha-adaptin | modifier of C99 | 50/51 |

We claim:

1. A transgenic fly whose genome comprises a DNA sequence encoding a polypeptide comprising an Abeta portion of human amyloid precursor protein (APP) wherein said DNA sequence encodes Abeta42 (SEQ ID NO:2), fused to a sequence, said DNA sequence being operably linked to an eye-specific promoter sequence, wherein expression of said DNA sequence results in said fly displaying a "rough eye" phenotype.

2. The transgenic fly of claim 1 wherein the eye-specific promoter sequence is the Glass Multimer Reporter (GMR) promoter.

3. A method to identify compounds useful for the treatment, or amelioration of conditions associated with abnormal regulation of the APP pathway comprising assaying for compounds that can modify the "rough eye" phenotypes induced by expression of Abeta42 said method comprising:

(a) providing a transgenic fly whose genome comprises a DNA sequence encoding a polypeptide comprising an Abeta portion of human APP wherein said DNA sequence encodes Abeta42 (SEQ ID NO: 2), fused to a sequence, said DNA sequence being operably linked to an eye-specific promoter sequence, wherein expression of said DNA sequence results in said fly displaying a "rough eye" phenotype;

(b) administering to said fly a candidate compound; and (c) assaying for changes in the phenotype of said fly of step (a) as compared to the phenotype of a fly of step (a) not administered the candidate compound.

4. The method of claim 3 wherein said condition is Alzheimer's Disease.

5. The method of claim 3 wherein the eye-specific promoter sequence is the GMR promoter.

* * * * *